US012703726B2

(12) United States Patent
McCray, Jr. et al.

(10) Patent No.: US 12,703,726 B2
(45) Date of Patent: Aug. 11, 2026

(54) COMPOSITIONS AND METHODS FOR THE TREATMENT OF CYSTIC FIBROSIS

(71) Applicant: University of Iowa Research Foundation, Iowa City, IA (US)

(72) Inventors: Paul B. McCray, Jr., Iowa City, IA (US); Patrick Sinn, Iowa City, IA (US); Laura Marquez Loza, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 821 days.

(21) Appl. No.: 17/921,510

(22) PCT Filed: Apr. 27, 2021

(86) PCT No.: PCT/US2021/029365

§ 371 (c)(1),
(2) Date: Oct. 26, 2022

(87) PCT Pub. No.: WO2021/222222

PCT Pub. Date: Nov. 4, 2021

(65) Prior Publication Data

US 2023/0174600 A1 Jun. 8, 2023

Related U.S. Application Data

(60) Provisional application No. 63/134,810, filed on Jan. 7, 2021, provisional application No. 63/015,958, filed on Apr. 27, 2020.

(51) Int. Cl.

| | |
|---|---|
| ***C07K 14/47*** | (2006.01) |
| ***A61K 9/00*** | (2006.01) |
| ***A61K 45/06*** | (2006.01) |
| ***A61K 48/00*** | (2006.01) |
| ***C12N 15/86*** | (2006.01) |

(52) U.S. Cl.

CPC ........ *C07K 14/4712* (2013.01); *A61K 9/0078* (2013.01); *A61K 45/06* (2013.01); *A61K 48/0058* (2013.01); *C12N 15/86* (2013.01); *C12N 2740/15043* (2013.01); *C12N 2800/22* (2013.01)

(58) Field of Classification Search

CPC ............................ C12N 15/86; C12N 2800/22
See application file for complete search history.

(56) References Cited

U.S. PATENT DOCUMENTS

| | | | | |
|---|---|---|---|---|
| 9,181,321 | B2 * | 11/2015 | Heartlein | A61K 9/0078 |
| 2010/0292307 | A1 | 11/2010 | Hyde et al. | |
| 2015/0038556 | A1 | 2/2015 | Heartlein et al. | |
| 2017/0096684 | A1 | 4/2017 | Alton et al. | |
| 2017/0326256 | A1 | 11/2017 | Doering et al. | |
| 2018/0015116 | A1 | 1/2018 | Heartlein et al. | |
| 2018/0256741 | A1 | 9/2018 | Dias et al. | |
| 2018/0333457 | A1 | 11/2018 | Heartlein et al. | |

FOREIGN PATENT DOCUMENTS

| | | | | |
|---|---|---|---|---|
| CN | 105142676 | | 12/2015 | |
| CN | 116096430 | | 5/2023 | |
| EP | 2007895 | B1 | 11/2014 | |
| JP | 2016517437 | A | 6/2016 | |
| JP | 2016535738 | A | 11/2016 | |
| JP | 2017521049 | A | 8/2017 | |
| JP | 2023515711 | | 4/2023 | |
| RU | 2658213 | C1 | 6/2018 | |
| RU | 2017143997 | A | 6/2019 | |
| WO | WO-2007110628 | A2 | 10/2007 | |
| WO | WO-2013119880 | A1 | 8/2013 | |
| WO | WO-2015012924 | A2 | 1/2015 | |
| WO | WO-2018157154 | A2 * | 8/2018 | A61K 31/7105 |
| WO | WO-2021222222 | A1 | 11/2021 | |

OTHER PUBLICATIONS

Romero, Zulema, et al. “The human ankyrin 1 promoter insulator sustains gene expression in a β-globin lentiviral vector in hematopoietic stem cells.” Molecular Therapy Methods & Clinical Development 2 (2015). (Year: 2015).*

Agent, Penny, and Helen Parrott. “Inhaled therapy in cystic fibrosis: agents, devices and regimens.” Breathe 11.2 (2015): 110-118. (Year: 2015).*

Lazrak, Ahmed, et al. “The silent codon change I507-ATC→ ATT contributes to the severity of the ΔF508 CFTR channel dysfunction.” The FASEB Journal 27.11 (2013): 4630. (Year: 2013).*

Sakuma, Toshie, Michael A. Barry, and Yasuhiro Ikeda. “Lentiviral vectors: basic to translational.” Biochemical Journal 443.3 (2012) : 603-618. (Year: 2012).*

Baser, Bahar, et al. “A method for specifically targeting two independent genomic integration sites for co-expression of genes in CHO cells.” Methods 95 (2016): 3-12. (Year: 2016).*

Wakabayashi-Ito, Noriko, and Shigekazu Nagata. “Characterization of the regulatory elements in the promoter of the human elongation factor-1 alpha gene.” Journal of Biological Chemistry 269.47 (1994): 29831-29837. (Year: 1994).*

Graham, Ian R., and Alistair Chambers. “Constitutive expression vectors: PGK.” Recombinant gene expression protocols. Totowa, NJ: Humana Press, 1997. 159-169. (Year: 1997).*

Bolognesi, Benedetta, et al. “Single point mutations induce a switch in the molecular mechanism of the aggregation of the Alzheimer’s disease associated Aβ42 peptide.” ACS Chemical Biology 9.2 (2014): 378-382. (Year: 2014).*

Wang, Xiaoling, et al. “Potential aggregation prone regions in biotherapeutics: a survey of commercial monoclonal antibodies.” MAbs. vol. 1. No. 3. Taylor & Francis, 2009. (Year: 2009).*

(Continued)

*Primary Examiner* — Lianko G Garyu
*Assistant Examiner* — David Paul Bowles
(74) *Attorney, Agent, or Firm* — Schwegman Lundberg & Woessner, P.A.

(57) ABSTRACT

Provided herein are polynucleotides, lentiviral vectors, pharmaceutical compositions, and methods of making and using the same, e.g., for treatment of cystic fibrosis (CF).

14 Claims, 13 Drawing Sheets

Specification includes a Sequence Listing.

(56) References Cited

OTHER PUBLICATIONS

Sawai, Monali V., et al. "Impact of single-residue mutations on the structure and function of ovispirin/novispirin antimicrobial peptides." Protein engineering 15.3 (2002): 225-232. (Year: 2002).*
Davis, Richard P., et al. "Targeting a GFP reporter gene to the MIXL1 locus of human embryonic stem cells identifies human primitive streak-like cells and enables isolation of primitive hematopoietic precursors." Blood, The Journal of the American Society of Hematology 111.4 (2008): 1876-1884. (Year: 2008).*
"International Application Serial No. PCT/US2021/029365, International Search Report mailed Sep. 7, 2021", 6 pgs.
"International Application Serial No. PCT/US2021/029365, Written Opinion mailed Sep. 7, 2021", 5 pgs.
Marquez Loza, Laura I., et al., "Increased CFTR expression and function from an optimized lentiviral vector for cystic fibrosis gene therapy", Molecular Therapy: Methods & Clinical Development vol. 21, (Jun. 2021), 94-106.
"Australian Application Serial No. 2021264465, First Examination Report mailed Apr. 29, 2024", 4 pgs.
"Chinese Application Serial No. 202180047309.4, Office Action mailed Feb. 13, 2025", w English translation, 28 pgs.
Kalpit, Shah, "Synonymous Codon Usage Affects the Expression of Wild Type and F508del CFTR", J Mol Biol., vol. 427, Issue 600, (Mar. 27, 2015), 1464-1479.
"International Application Serial No. PCT US2021 029365, International Preliminary Report on Patentability mailed Nov. 10, 2022", 7 pgs.
"Chinese Application Serial No. 202180047309.4, Notification to Make Rectification mailed Feb. 23, 2023", with machine translation, 2 pgs.
"Singaporean Application Serial No. 11202254416W, Voluntary Amendment Filed Apr. 8, 2023", W English Claims, 9 pgs.
"Russian Application Serial No. 2022130588, Office Action mailed Jun. 2, 2023", w English translation, 17 pgs.
"Israeli Application Serial No. 297562, Notification Prior to Examination mailed Jun. 15, 2023", with English Translation, 9 pgs.
"European Application Serial No. 21730320.5, Response filed Sep. 8, 2023 to Communication Pursuant to Rule 112(1) EPC mailed Jul. 7, 2023", 16 pgs.
"Israeli Application Serial No. 297562, Response Filed Oct. 23, 2023 to Notification Prior to Examination mailed Jun. 15, 2023", with machine translation, 26 pgs.
"Japanese Application Serial No. 2022-565627, Notification of Reasons for Rejection mailed Nov. 28, 2023", with machine translation, 14 pgs.
"Russian Application Serial No. 2022130588, Office Action mailed Oct. 23, 2023", w/ English Translation, 18 pgs.
Soo, Jung Kim, et al., "Supplementary Material for Translational tuning optimizes nascent protein folding in cells", Science, vol. 348, No. 6233, (2015), 28 pgs.

* cited by examiner

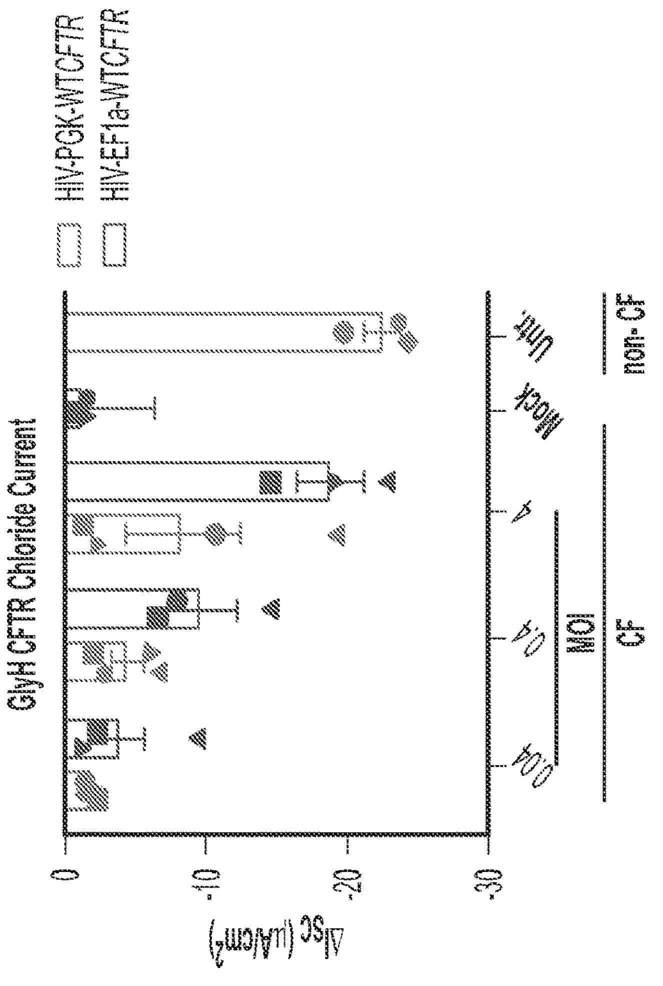
FIG. 4E
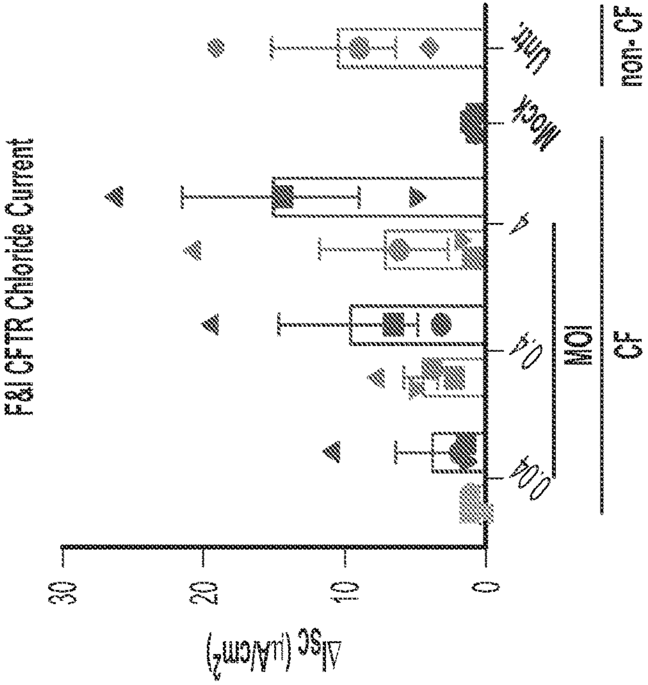

FIG. 5A

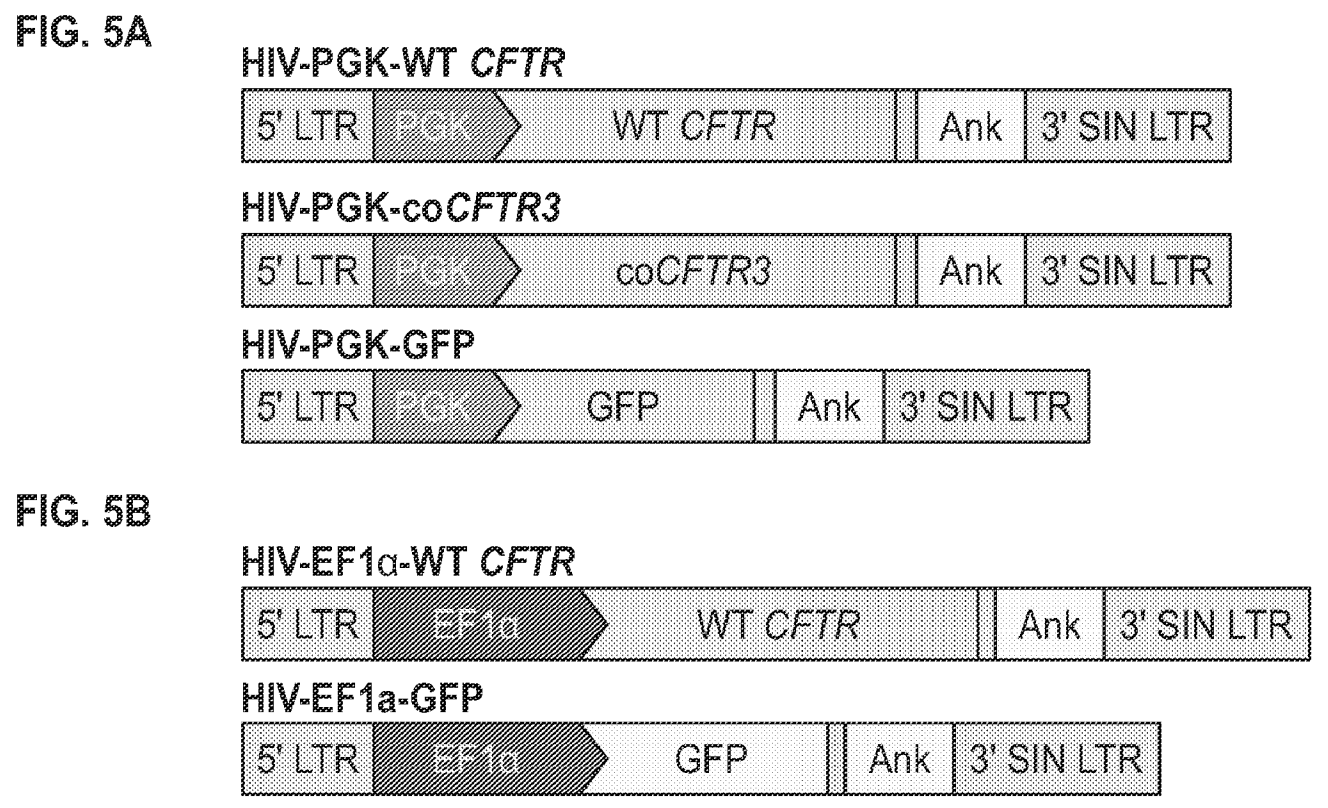

HIV-PGK-WT *CFTR*

5' LTR | PGK | WT *CFTR* | Ank | 3' SIN LTR

HIV-PGK-co*CFTR3*

5' LTR | PGK | co*CFTR3* | Ank | 3' SIN LTR

HIV-PGK-GFP

5' LTR | PGK | GFP | Ank | 3' SIN LTR

FIG. 5B

HIV-EF1α-WT *CFTR*

5' LTR | EF1α | WT *CFTR* | Ank | 3' SIN LTR

HIV-EF1a-GFP

5' LTR | EF1α | GFP | Ank | 3' SIN LTR

SEQUENCE LISTING

<160> NUMBER OF SEQ ID NOS: 13

<210> SEQ ID NO 1
<211> LENGTH: 4443
<212> TYPE: DNA
<213> ORGANISM: Artificial Sequence
<220> FEATURE:
<223> OTHER INFORMATION: A synthetic sequence

<400> SEQUENCE: 1
atgcagcgta gtcctcttga gaaagccagc gtggtgagta aactgttttt ctcatggaca 60
aggcccatcc tgcggaaagg gtatcgtcag aggctcgagc tcagcgacat ctatcagata 120
ccctccgttg actctgccga taacttgagt gaaaaactgg agcgagagtg ggatcgggaa 180
ctggcatcta agaagaatcc caagctcatc aacgccctga gaagatgctt cttttggaga 240
ttcatgtttt atgggatttt cctgtacctc ggcgaggtga ccaaggcagt gcagcctctt 300
cttctgggcc ggataattgc tagttacgac ccagacaaca aggaggagcg gtctatagcc 360
atctacctgg gcattgggct ctgtctcctg tttatcgtgc gtacccttct gctgcaccct 420
gctattttcg gcctgcatca catcgggatg cagatgcgaa tcgcaatgtt cagcctaatc 480
tacaagaaaa cactgaagct atcatccaga gtgttggata agatcagtat cgggcagctc 540
gtatccttgt tgtctaataa ccttaataag ttcgatgagg gcttagcact cgcacacttt 600
gtatggatcg caccactcca ggtggcgctg ctaatgggct tgatatggga acttctccag 660
gcttcagcat tttgtggcct gggtttctta atcgtgctgg ccttgtttca agctggcttg 720
ggcagaatga tgatgaaata cagagaccag agagccggga aaatcagcga gaggctggtc 780
atcacatcag aaatgatcga aaatatccaa tcggtaaagg cctactgctg ggaggaggct 840
atggagaaga tgattgagaa cctcagacaa accgaactga agctaacccg gaaggccgca 900
tacgtccgct atttcaactc aagtgccttc ttcttctccg gcttctttgt cgttttcctg 960
tctgttcttc cttacgcatt aatcaaaggt attatactca ggaagatttt tacaaccatt 1020
tctttttgta ttgtcttgag gatggccgta acacgacaat tcccttgggc tgtccagact 1080
tggtacgact ccctgggtgc cattaacaag atccaggact tccttcagaa gcaggagtac 1140
aaaaccctgg aatacaatct tacgaccaca gaggtggtca tggaaaatgt taccgctttc 1200
tgggaggagg gttttggcga attatttgag aaagctaaac agaacaacaa taatcgcaag 1260
actagcaatg gcgatgacag ccttttcttc tcaaacttct cattgctggg cactccggtc 1320
ctgaaggaca tcaactttaa gattgagcgt ggtcagctat tggccgttgc cggaagcacc 1380
ggagcgggca agactagcct gctcatgatg ataatgggcg agctcgaacc ctcagaggga 1440
aaaattaagc attccggacg cattagcttt tgttcccaat tctcgtggat tatgcccggc 1500
acgatcaaag agaacatcat attcggagtc tcttacgacg agtacaggta ccggtctgta 1560
attaaggctt gtcagcttga ggaggacatt tctaaattcg ccgagaagga taatattgtg 1620
ttaggagaag gggggataac cctgagtggg ggccagagag ccagaataag tctcgcacgc 1680
gctgtgtaca aagacgctga cctctacctg ttagactccc cttttggata cctggacgtc 1740

-continued

```
ttgaccgaaa aggagatttt cgagtcttgc gtttgcaaac tcatggccaa caaaacccgg   1800
atactggtga ctagcaaaat ggagcacctg aagaaggcag ataagatcct gatccttcac   1860
gagggcagct cttatttcta cggcacgttt tctgaactac agaacctgca gccagacttc   1920
agttcaaagc tgatgggttg tgattccttt gaccagtttt cagcagaacg gagaaacagt   1980
attctcacag aaactctcca caggttctcc ttagaggggg acgccccggt gagctggacc   2040
gaaactaaaa aacaatcatt caagcagact ggcgagttcg gtgagaagag aaagaactcc   2100
attctgaacc cgatcaactc aatccgaaaa ttctctattg tgcagaagac ccctttgcag   2160
atgaacggca tagaagaaga tagcgatgag ccattggagc gcagactatc tctggtgccc   2220
gattccgagc agggtgaagc tattttgccg agaatcagcg tgattagtac cggtccaaca   2280
ctccaggcca ggcggcgcca gtctgtgctg aatctgatga cacacagcgt caatcagggt   2340
caaaacatcc acagaaagac cacagcctcc actagaaagg ttagtttagc gcctcaagct   2400
aacctcacag agctcgatat ctactcaaga cgcctgagtc aagaaacggg attggagatc   2460
agcgaggaaa ttaatgagga ggacttgaag gagtgccttt tcgatgacat ggaaagtatc   2520
cccgccgtga ccacatggaa tacatatctg cggtatatca ctgtgcacaa atctttgatc   2580
ttcgtgctga tctggtgtct ggttatcttt ttggccgagg tcgccgcttc actggtggtt   2640
ctttggttgc tcggcaatac ccccctgcag gataaaggga actcaactca ctcaagaaac   2700
aatagttatg ccgtgataat tacaagcact tcgtcttatt acgtgttcta catctatgtg   2760
ggtgtggccg acactctact tgctatggga tttttccgtg ggctgcccct tgtgcacaca   2820
ttgattaccg taagcaaaat cctccaccat aaaatgctgc actcagtgct gcaggctcca   2880
atgagcactc tcaacacttt gaaggccgga ggaatcctta ataggttttc taaggacatt   2940
gccattttgg atgatctgct cccactgacc attttcgatt tcattcaact cctcctgatc   3000
gtgattggcg caattgccgt ggttgctgtg ttacagccct atattttcgt ggcgacagtg   3060
cccgttattg tggctttcat catgctgcgt gcctacttcc ttcagaccag tcaacaactc   3120
aagcagcttg agtcagaggg ccgctccccg attttcaccc atctggtcac gtctcttaaa   3180
ggcctgtgga ccctgagggc ctttgggagg cagccctatt ttgaaaccct ctttcacaag   3240
gctctgaatt tgcacactgc caattggttc ctctacttgt caactctcag gtggttccag   3300
atgagaatcg aaatgatctt tgtgatcttt ttcatcgcag tcacttttat aagcatcctg   3360
accaccggcg aaggggaggg gcgggtcgga atcatcttaa ctctggccat gaatattatg   3420
agcactctac aatgggccgt gaatagctca attgatgtgg actcgctgat gagaagcgtg   3480
agccgcgtct ttaaattcat tgacatgcca actgaaggca agccaacgaa gagtactaag   3540
ccttataaaa acggccaact gtcaaaggtc atgattatcg aaaattccca tgtgaagaaa   3600
gacgacattt ggccctctgg aggacagatg accgtcaagg atctcaccgc aaaatatact   3660
gagggcggga acgccatttt ggaaaacatc tcgttttcta tcagccccgg tcagagagtc   3720
ggtctgctcg gcaggactgg atctgggaaa tccactttgt tatccgcttt cctccgcctt   3780
ctgaacaccg agggggagat ccagattgat ggagtgagct gggattcgat cactctgcag   3840
cagtggcgga aggcctttgg cgtgatccct cagaaagtgt ttatcttttc cgggaccttt   3900
cgaaagaatc tcgatcctta cgagcagtgg tctgaccaag aaatctggaa agtcgctgac   3960
gaggtggggc tgaggtctgt aatcgagcag ttccctggga aactcgattt tgtgcttgtg   4020
gacggcggat gtgtactgtc tcatggacac aagcaattga tgtgcctggc acgcagcgtg   4080
ctctcgaagg ctaagatact tctgctggac gaaccatcag cacacttaga tccagtgaca   4140
```

```
tatcaaatca tcaggcgaac cctgaaacaa gcattcgcag attgtaccgt gatcctgtgt   4200

gaacatcgga ttgaggccat gctggagtgc cagcagtttc tggtcattga ggaaaacaag   4260

gttcgccagt acgattcgat ccaaaaatta ctgaatgaga gatcactgtt taggcaggcc   4320

atttcaccca gcgaccgtgt aaagttgttt cctcaccgaa actcgagtaa atgcaaatct   4380

aagccacaga ttgcagccct gaaagaggag acagaggagg aggtgcaaga caccaggttg   4440

tag                                                                 4443
```

<210> SEQ ID NO 2
<211> LENGTH: 4443
<212> TYPE: DNA
<213> ORGANISM: Artificial Sequence
<220> FEATURE:
<223> OTHER INFORMATION: A synthetic sequence

<400> SEQUENCE: 2

```
atgcagcgca gcccccctgga gaaggccagc gtggtgagca agctgttctt cagctggacc     60

cgccccatcc tgcgcaaggg ctaccgccag cgcctggagc tgagcgacat ctaccagatc    120

cccagcgtgg acagcgccga caacctgagc gagaagctgg agcgcgagtg ggaccgcgag    180

ctggccagca agaagaaccc caagctgatc aacgccctgc gccgctgctt cttctggcgc    240

ttcatgttct acggcatctt cctgtacctg ggcgaggtga ccaaggccgt gcagcccctg    300

ctgctgggcc gcatcatcgc cagctacgac cccgacaaca aggaggagcg cagcatcgcc    360

atctacctgg gcatcggcct gtgcctgctg ttcatcgtgc gcaccctgct gctgcacccc    420

gccatcttcg gcctgcacca catcggcatg cagatgcgca tcgccatgtt cagcctgatc    480

tacaagaaga ccctgaagct gagcagccgc gtgctggaca agatcagcat cggccagctg    540

gtgagcctgc tgagcaacaa cctgaacaag ttcgacgagg gcctggccct ggcccacttc    600

gtgtggatcg ccccctgca ggtggccctg ctgatgggcc tgatctggga gctgctgcag     660

gccagcgcct tctgcggcct gggcttcctg atcgtgctgg ccctgttcca ggccggcctg    720

ggccgcatga tgatgaagta ccgcgaccag cgcgccggca agatcagcga gcgcctggtg    780

atcaccagcg agatgatcga gaacatccag agcgtgaagg cctactgctg ggaggaggcc    840

atggagaaga tgatcgagaa cctgcgccag accgagctga agctgacccg caaggccgcc    900

tacgtgcgct acttcaacag cagcgccttc ttcttcagcg gcttcttcgt ggtgttcctg    960

agcgtgctgc cctacgccct gatcaagggc atcatcctgc gcaagatctt caccaccatc   1020

agcttctgca tcgtgctgcg catggccgtg acccgccagt tcccctgggc cgtgcagacc   1080

tggtacgaca gcctgggcgc catcaacaag atccaggact tcctgcagaa gcaggagtac   1140

aagaccctgg agtacaacct gaccaccacc gaggtggtga tggagaacgt gaccgccttc   1200

tgggaggagg gcttcggcga gctgttcgag aaggccaagc agaacaacaa caaccgcaag   1260

accagcaacg gcgacgacag cctgttcttc agcaacttca gcctgctggg cacccccgtg   1320

ctgaaggaca tcaacttcaa gatcgagcgc ggccagctgc tggccgtggc cggcagcacc   1380

ggcgccggca agaccagcct gctgatgatg atcatgggcg agctggagcc cagcgagggc   1440

aagatcaagc acagcggccg catcagcttc tgcagccagt tcagctggat catgcccggc   1500

accatcaagg agaacatcat cttcggcgtg agctacgacg agtaccgcta ccgcagcgtg   1560

atcaaggcct gccagctgga ggaggacatc agcaagttcg ccgagaagga caacatcgtg   1620

ctgggcgagg gcggcatcac cctgagcggc ggccagcgcg cccgcatcag cctggcccgc   1680
```

```
gccgtgtaca aggacgccga cctgtacctg ctggacagcc ccttcggcta cctggacgtg   1740
ctgaccgaga aggagatctt cgagagctgc gtgtgcaagc tgatggccaa caagacccgc   1800
atcctggtga ccagcaagat ggagcacctg aagaaggccg acaagatcct gatcctgcac   1860
gagggcagca gctacttcta cggcaccttc agcgagctgc agaacctgca gcccgacttc   1920
agcagcaagc tgatgggctg cgacagcttc gaccagttca gcgccgagcg ccgcaacagc   1980
atcctgaccg agaccctgca ccgcttcagc ctggagggcg acgcccccgt gagctggacc   2040
gagaccaaga agcagagctt caagcagacc ggcgagttcg gcgagaagcg caagaacagc   2100
atcctgaacc ccatcaacag catccgcaag ttcagcatcg tgcagaagac cccccctgcag   2160
atgaacggca tcgaggagga cagcgacgag cccctggagc gccgcctgag cctggtgccc   2220
gacagcgagc agggcgaggc catcctgccc cgcatcagcg tgatcagcac cggccccacc   2280
ctgcaggccc gccgccgcca gagcgtgctg aacctgatga cccacagcgt gaaccagggc   2340
cagaacatcc accgcaagac caccgccagc acccgcaagg tgagcctggc cccccaggcc   2400
aacctgaccg agctggacat ctacagccgc cgcctgagcc aggagaccgg cctggagatc   2460
agcgaggaga tcaacgagga ggacctgaag gagtgcttct tcgacgacat ggagagcatc   2520
cccgccgtga ccacctggaa cacctacctg cgctacatca ccgtgcacaa gagcctgatc   2580
ttcgtgctga tctggtgcct ggtgatcttc ctggccgagg tggccgccag cctggtggtg   2640
ctgtggctgc tgggcaacac cccccctgcag gacaagggca acagcaccca cagccgcaac   2700
aacagctacg ccgtgatcat caccagcacc agcagctact acgtgttcta catctacgtg   2760
ggcgtggccg acaccctgct ggccatgggc ttcttccgcg gcctgcccct ggtgcacacc   2820
ctgatcaccg tgagcaagat cctgcaccac aagatgctgc acagcgtgct gcaggccccc   2880
atgagcaccc tgaacaccct gaaggccggc ggcatcctga accgcttcag caaggacatc   2940
gccatcctgg acgacctgct gcccctgacc atcttcgact tcatccagct gctgctgatc   3000
gtgatcggcg ccatcgccgt ggtggccgtg ctgcagccct acatcttcgt ggccaccgtg   3060
cccgtgatcg tggccttcat catgctgcgc gcctacttcc tgcagaccag ccagcagctg   3120
aagcagctgg agagcgaggg ccgcagcccc atcttcaccc acctggtgac cagcctgaag   3180
ggcctgtgga ccctgcgcgc cttcggccgc cagccctact tcgagaccct gttccacaag   3240
gccctgaacc tgcacaccgc caactggttc ctgtacctga gcaccctgcg ctggttccag   3300
atgcgcatcg agatgatctt cgtgatcttc ttcatcgccg tgaccttcat cagcatcctg   3360
accaccggcg agggcgaggg ccgcgtgggc atcatcctga ccctggccat gaacatcatg   3420
agcaccctgc agtgggccgt gaacagcagc atcgacgtgg acagcctgat gcgcagcgtg   3480
agccgcgtgt tcaagttcat cgacatgccc accgagggca agcccaccaa gagcaccaag   3540
ccctacaaga acggccagct gagcaaggtg atgatcatcg agaacagcca cgtgaagaag   3600
gacgacatct ggcccagcgg cggccagatg accgtgaagg acctgaccgc caagtacacc   3660
gagggcggca acgccatcct ggagaacatc agcttcagca tcagccccgg ccagcgcgtg   3720
ggcctgctgg gccgcaccgg cagcggcaag agcaccctgc tgagcgcctt cctgcgcctg   3780
ctgaacaccg agggcgagat ccagatcgac ggcgtgagct gggacagcat caccctgcag   3840
cagtggcgca aggccttcgg cgtgatcccc cagaaggtgt tcatcttcag cggcaccttc   3900
cgcaagaacc tggaccccta cgagcagtgg agcgaccagg agatctggaa ggtggccgac   3960
gaggtgggcc tgcgcagcgt gatcgagcag ttccccggca agctggactt cgtgctggtg   4020
gacggcggct gcgtgctgag ccacggccac aagcagctga tgtgcctggc ccgcagcgtg   4080
```

```
ctgagcaagg ccaagatcct gctgctggac gagcccagcg cccacctgga ccccgtgacc   4140

taccagatca tccgccgcac cctgaagcag gccttcgccg actgcaccgt gatcctgtgc   4200

gagcaccgca tcgaggccat gctggagtgc cagcagttcc tggtgatcga ggagaacaag   4260

gtgcgccagt acgacagcat ccagaagctg ctgaacgagc gcagcctgtt ccgccaggcc   4320

atcagcccca gcgaccgcgt gaagctgttc ccccaccgca acagcagcaa gtgcaagagc   4380

aagccccaga tcgccgccct gaaggaggag accgaggagg aggtgcagga cacccgcctg   4440

taa                                                                 4443


<210> SEQ ID NO 3
<211> LENGTH: 4443
<212> TYPE: DNA
<213> ORGANISM: Artificial Sequence
<220> FEATURE:
<223> OTHER INFORMATION: A synthetic sequence

<400> SEQUENCE: 3

atgcagcgga gccctcttga gaaagccagc gtggtgtcca agctgttctt cagctggacc     60

cggcctatcc tgagaaaggg ctacagacag agactggaac tgagcgacat ctatcagatc    120

cccagcgtgg acagcgccga caatctgagc gagaagctgg aaagagagtg ggacagagag    180

ctggcctcca agaagaaccc caagctgatc aacgccctgc ggagatgctt cttctggcgg    240

tttatgttct acggcatctt cctgtacctg ggcgaagtga caaaagccgt gcagcctctg    300

ctgctgggca gaatcattgc cagctacgac cccgacaaca aagaggaacg gtctatcgcc    360

atctacctcg gcatcggcct gtgcctgctg tttattgtca gaaccctgct gctgcacccc    420

gccatctttg gactgcacca catcggcatg cagatgcgga tcgccatgtt cagcctgatc    480

tacaagaaaa ccctgaagct gtccagccga gtgctggaca agatctctat cggacagctg    540

gtgtccctgc tgagcaacaa cctgaacaag ttcgacgaag gcctggctct ggcccacttt    600

gtgtggattg ctcctctgca agtggccctg ctgatgggac tgatttggga actgctgcag    660

gccagcgcct ttgtgggcct gggatttctg atcgtgctgg ccctgtttca ggccggactg    720

ggaagaatga tgatgaagta cagggaccag agagccggca agatcagcga gagactggtc    780

atcaccagcg agatgatcga gaacatccag agcgtgaagg cctactgctg ggaagaggcc    840

atggaaaaga tgattgagaa tctgcggcag accgagctga agctgacaag aaaggccgcc    900

tacgtgcggt acttcaacag cagcgccttc ttcttctccg gcttcttcgt ggtgttcctg    960

agcgtgctgc cctacgctct gatcaagggc atcatcctgc ggaagatctt tacgacaatc   1020

agcttctgca ttgtgctgcg gatggccgtg accagacagt ttccttgggc tgtgcagact   1080

tggtacgata gcctgggcgc catcaacaag atccaggact tcctgcagaa gcaagagtac   1140

aagaccctcg agtacaacct gaccaccacc gaggtggtca tggaaaacgt gaccgccttc   1200

tgggaggaag gcttcggcga gctgtttgag aaggccaagc agaacaacaa caaccgcaag   1260

accagcaacg gcgacgacag cctgttcttc tccaatttct ctctgctggg gacccctgtg   1320

ctgaaggaca tcaacttcaa gatcgagcgg ggacagctgc tggccgttgc aggatctaca   1380

ggcgccggaa agacaagtct gctgatgatg atcatgggcg agctggaacc cagcgaggga   1440

aagatcaagc acagcggccg gattagcttc tgtagccagt tctcctggat catgcccggc   1500

accatcaaag agaacatcat cttcggcgtg tcctacgacg agtacagata cagaagcgtg   1560

atcaaggcct gccagctgga agaggacatc agcaagttcg ccgagaagga caacatcgtg   1620
```

```
ctcggcgaag gcggaatcac actgtctggc ggccagaggg ctagaatctc tctggctaga   1680
gccgtgtaca aggacgccga tctgtacctg ctggatagcc cctttggcta cctggacgtg   1740
ctgaccgaga aagagatctt cgagagctgc gtgtgcaagc tgatggccaa caagaccaga   1800
atcctcgtga ccagcaagat ggaacacctg aagaaggccg acaagatcct gatcctgcac   1860
gagggcagca gctactttta cggcaccttc agcgaactgc agaacctgca gcctgacttc   1920
agcagcaaac tgatgggctg cgactccttc gatcagttca gcgccgagcg gagaaacagc   1980
atcctgacag agacactgca cagattcagc ctggaaggcg acgcccctgt gtcttggacc   2040
gagacaaaga agcagagctt caagcagacc ggcgagtttg gcgagaagag aaagaacagc   2100
attctgaacc ccatcaactc catccggaag ttcagcatcg tgcagaaaac ccctctgcag   2160
atgaacggca tcgaagagga tagcgacgag cccctggaaa gacgactgag cctggtgcct   2220
gattctgagc agggcgaagc catcctgcct agaatttccg tgatcagcac tggccccaca   2280
ctgcaggctc gaagaaggca gtctgtcctg aacctgatga cccacagcgt gaaccaggga   2340
cagaatatcc acagaaagac caccgccagc acacggaaag tttctctggc acctcaggcc   2400
aacctgactg agctggacat ctacagcaga cggctgagcc aagagacagg cctggaaatc   2460
agcgaggaaa tcaacgaaga ggacctgaaa gagtgcttct tcgacgacat ggaatctatc   2520
cccgccgtga caacctggaa cacatacctg cggtacatca ccgtgcacaa gtccctgatc   2580
ttcgtgctga tctggtgcct cgtgatcttt ctggccgaag tggctgcttc tctggtggtt   2640
ctgtggctgc tcggaaacac ccccactgcag gataagggca acagcaccca cagcagaaac   2700
aacagctacg ccgtgatcat cacctccacc agctcctact acgtgttcta catctacgtc   2760
ggcgtggccg acacactgct ggccatgggc ttttttagag gactgcctct ggtgcacacc   2820
ctgatcaccg tgtccaagat tctgcaccat aagatgctgc acagcgtcct gcaggcccct   2880
atgagcacac tgaatactct gaaggctggc ggcatcctga acaggttcag caaggacatt   2940
gccatcctgg acgacctgct gcctctgacc atcttcgact tcatccagct gctgctgatc   3000
gtgatcggag ccattgctgt ggtggccgtg ctgcagcctt atatctttgt ggccaccgtg   3060
cctgtgatcg tggccttcat tatgctgcgg gcctactttc tgcagacctc tcagcagctg   3120
aagcagctcg agtctgaggg cagaagccct atctttaccc acctggtcac cagcctgaaa   3180
ggcctgtgga cactgagagc cttcggcagg cagccttact tcgagacact gttccacaag   3240
gccctgaatc tgcacaccgc caactggttc ctctacctga gcaccctgcg gtggttccag   3300
atgagaatcg agatgatttt cgtcatcttc tttatcgccg tgaccttcat ctccattctg   3360
accactggcg aaggcgaggg cagagtggga attatcctga cactggccat gaacatcatg   3420
tctaccctcc agtgggccgt gaacagcagc atcgatgtgg acagcctgat gcggagcgtg   3480
tcccgggtgt tcaagttcat cgatatgccc accgagggca agcccaccaa gagcaccaag   3540
ccttacaaga atggccagct gagcaaagtg atgattatcg agaactccca cgtgaagaag   3600
gacgatatct ggcccagcgg cggacagatg accgtgaaag atctgaccgc caagtacacc   3660
gaaggcggca acgccattct ggaaaacatc agctttagca tcagccctgg ccagagagtc   3720
ggactgcttg gcagaacagg cagcggaaag tctaccctgc tgtccgcctt cctgagactg   3780
ctgaataccg agggcgagat ccagatcgat ggggtgtcct gggatagcat cacactccaa   3840
cagtggcgga aggcctttgg cgtgatccct cagaaggtgt tcattttcag cggcaccttt   3900
cggaagaatc tggaccccta cgagcagtgg tccgaccaag agatttggaa ggtggccgac   3960
gaagtgggcc tgagatctgt gatcgagcag tttcccggca agctggattt cgtgctggtg   4020
```

```
gatggcggat gtgtgctgtc tcacggacac aagcagctga tgtgcctggc tagaagcgtg   4080

ctgtctaagg ccaagatcct cctgctggac gagccctctg cacatctgga tcctgtgacc   4140

taccagatca tccggcggac actgaagcag gcctttgccg attgcaccgt gatcctgtgc   4200

gagcacagaa tcgaggccat gctggaatgc cagcagtttc tcgtgatcga agagaacaaa   4260

gtgcggcagt acgacagcat ccagaagctg ctgaacgagc ggagcctgtt cagacaggcc   4320

atctctccca gcgacagagt gaagctgttc cctcaccgga acagctccaa gtgcaagagc   4380

aagcctcaga tcgccgctct gaaagaagaa accgaggaag aggtgcagga caccagactc   4440

tga                                                                 4443
```

<210> SEQ ID NO 4
<211> LENGTH: 523
<212> TYPE: DNA
<213> ORGANISM: Homo sapiens

<400> SEQUENCE: 4

```
tcgaattccc acggggttgg ggttgcgcct tttccaaggc agccctgggt ttgcgcaggg     60

acgcggctgc tctgggcgtg gttccgggaa acgcagcggc gccgaccctg ggtctcgcac    120

attcttcacg tccgttcgca gcgtcacccg gatcttcgcc gctacccttg tgggcccccc    180

ggcgacgctt cctgctccgc ccctaagtcg ggaaggttcc ttgcggttcg cggcgtgccg    240

gacgtgacaa acggaagccg cacgtctcac tagtaccctc gcagacggac agcgccaggg    300

agcaatggca gcgcgccgac cgcgatgggc tgtggccaat agcggctgct cagcggggcg    360

cgccgagagc agcggccggg aaggggcggt gcgggaggcg gggtgtgggg cggtagtgtg    420

ggccctgttc ctgcccgcgc ggtgttccgc attctgcaag cctccggagc gcacgtcggc    480

agtcggctcc ctcgttgacc gaatcaccga cctctctccc cag                      523
```

<210> SEQ ID NO 5
<211> LENGTH: 1184
<212> TYPE: DNA
<213> ORGANISM: Homo sapiens

<400> SEQUENCE: 5

```
atatcggctc cggtgcccgt cagtgggcag agcgcacatc gcccacagtc cccgagaagt     60

tggggggagg ggtcggcaat tgaaccggtg cctagagaag gtggcgcggg gtaaactggg    120

aaagtgatgt cgtgtactgg ctccgccttt ttcccgaggg tgggggagaa ccgtatataa    180

gtgcagtagt cgccgtgaac gttctttttc gcaacgggtt tgccgccaga acacaggtaa    240

gtgccgtgtg tggttcccgc gggcctggcc tctttacggg ttatggccct tgcgtgcctt    300

gaattacttc cacgcccctg gctgcagtac gtgattcttg atcccgagct tcgggttgga    360

agtgggtggg agagttcgag gccttgcgct taaggagccc cttcgcctcg tgcttgagtt    420

gaggcctggc ctgggcgctg gggccgccgc gtgcgaatct ggtggcacct tcgcgcctgt    480

ctcgctgctt tcgataagtc tctagccatt taaaattttt gatgacctgc tgcgacgctt    540

tttttctggc aagatagtct tgtaaatgcg ggccaagatc tgcacactgg tatttcggtt    600

tttggggccg cgggcggcga cggggcccgt gcgtcccagc gcacatgttc ggcgaggcgg    660

ggcctgcgag cgcggccacc gagaatcgga cgggggtagt ctcaagctgg ccggcctgct    720

ctggtgcctg gcctcgcgcc gccgtgtatc gccccgccct gggcggcaag gctggcccgg    780

tcggcaccag ttgcgtgagc ggaaagatgg ccgcttcccg gccctgctgc agggagctca    840
```

-continued

```
aaatggagga cgcggcgctc gggagagcgg gcgggtgagt cacccacaca aaggaaaagg    900

gcctttccgt cctcagccgt cgcttcatgt gactccacgg agtaccgggc gccgtccagg    960

cacctcgatt agttctcgag cttttggagt acgtcgtctt taggttgggg ggaggggttt   1020

tatgcgatgg agtttcccca cactgagtgg gtggagactg aagttaggcc agcttggcac   1080

ttgatgtaat tctccttgga atttgccctt tttgagtttg gatcttggtt cattctcaag   1140

cctcagacag tggttcaaag tttttttctt ccatttcagg tgtc                    1184


<210> SEQ ID NO 6
<211> LENGTH: 21
<212> TYPE: DNA
<213> ORGANISM: Artificial Sequence
<220> FEATURE:
<223> OTHER INFORMATION: A synthetic sequence

<400> SEQUENCE: 6

ctcgactgtg ccttctagtt g                                               21


<210> SEQ ID NO 7
<211> LENGTH: 18
<212> TYPE: DNA
<213> ORGANISM: Artificial Sequence
<220> FEATURE:
<223> OTHER INFORMATION: A synthetic sequence

<400> SEQUENCE: 7

gcaccttcca gggtcaag                                                   18


<210> SEQ ID NO 8
<211> LENGTH: 18
<212> TYPE: DNA
<213> ORGANISM: Artificial Sequence
<220> FEATURE:
<223> OTHER INFORMATION: A synthetic sequence

<400> SEQUENCE: 8

ggatttggtc gtattggg                                                   18


<210> SEQ ID NO 9
<211> LENGTH: 18
<212> TYPE: DNA
<213> ORGANISM: Artificial Sequence
<220> FEATURE:
<223> OTHER INFORMATION: A synthetic sequence

<400> SEQUENCE: 9

ggatttggtc gtattggg                                                   18


<210> SEQ ID NO 10
<211> LENGTH: 20
<212> TYPE: DNA
<213> ORGANISM: Artificial Sequence
<220> FEATURE:
<223> OTHER INFORMATION: A synthetic sequence

<400> SEQUENCE: 10

cgactggtga gtacgccaaa                                                 20


<210> SEQ ID NO 11
<211> LENGTH: 21
<212> TYPE: DNA
<213> ORGANISM: Artificial Sequence
<220> FEATURE:
<223> OTHER INFORMATION: A synthetic sequence
```

```
<400> SEQUENCE: 11

cgcacccatc tctctccttc t                                              21


<210> SEQ ID NO 12
<211> LENGTH: 18
<212> TYPE: DNA
<213> ORGANISM: Artificial Sequence
<220> FEATURE:
<223> OTHER INFORMATION: A synthetic sequence

<400> SEQUENCE: 12

attttgacta gcggaggc                                                  18


<210> SEQ ID NO 13
<211> LENGTH: 486
<212> TYPE: DNA
<213> ORGANISM: Homo sapiens

<400> SEQUENCE: 13

tttaagacca atgacttaca aggcagctgt agatcttagc cactttttaa aagaaaaggg     60

gggactggaa gggctaattc actcccaacg aagacaagat ctgctttttg ctgtgcgggc    120

caggcccccg agggccttat cggccccaga ggcgcttgct gtcgggccgg gcgctcccgg    180

cacgggcggg cggaggggtg gcgcccgcct ggggaccgca gattacaaga gcacctcctc    240

ccccaacccc aggaggcccc gctccccagg cctcggccgg cgcggacccc tggttgcccc    300

ggactgggtc tctctggtta gaccagatct gagcctggga gctctctggc taactaggga    360

acccactgct taagcctcaa taaagcttgc cttgagtgct tcaagtagtg tgtgcccgtc    420

tgttgtgtga ctctggtaac tagagatccc tcagaccctt ttagtcagtg tggaaaatct    480

ctagca                                                              486
```

COMPOSITIONS AND METHODS FOR THE TREATMENT OF CYSTIC FIBROSIS

CROSS REFERENCE TO RELATED APPLICATIONS

This application is a U.S. National Stage Filing under 35 U.S.C. 371 from International Application No. PCT/US2021/029365, filed on Apr. 27, 2021, and published as WO 2021/222222 on Nov. 4, 2021, which application claims the benefit of the filing date of U.S. application No. 63/015,958, filed on Apr. 27, 2020 and U.S. application No. 63/134,810, filed on Jan. 7, 2021, the disclosures of which are incorporated by reference herein.

STATEMENT OF GOVERNMENT RIGHTS

This invention was made with government support under HL051670 awarded by the National Institutes of Health. The government has certain rights in the invention.

BACKGROUND

Cystic fibrosis (CF) is a lethal, autosomal-recessive disorder that affects at least 30,000 people in the U.S. alone and at least 70,000 people worldwide. The average survival age for CF patients is about 40 years. CF is caused by mutations in the gene encoding the cystic fibrosis transmembrane conductance regulator (CFTR), a channel that conducts chloride and bicarbonate ions across epithelial cell membranes. Impaired CFTR function leads to inflammation of the airways and progressive bronchiectasis. Because of the single-gene etiology of CF and the various CFTR mutations in the patient population, gene therapy potentially provides a universal cure for CF.

Recent studies suggest that gene therapy may offer great benefits to CF patients even if only partial correction of CFTR gene function is achieved. However, there remains a need in the art for improved compositions and methods for treatment of CF.

SUMMARY

The disclosure provides, inter alia, isolated polynucleotides, lentiviral vectors, virions, and pharmaceutical compositions, and methods of making and using the same, e.g., in the treatment of CF.

In one aspect, the disclosure provides an isolated polynucleotide comprising a nucleotide sequence having at least 95% sequence identity to the nucleotide sequence of SEQ ID NO:1. In some embodiments, the isolated polynucleotide comprises a nucleotide sequence having at least 96%, at least 97%, at least 98%, or at least 99% sequence identity to the nucleotide sequence of SEQ ID NO:1. In some embodiments, the isolated polynucleotide comprises the nucleotide sequence of SEQ ID NO:1.

In another aspect, the disclosure provides an isolated polynucleotide comprising the nucleotide sequence of SEQ ID NO:2.

In another aspect, the disclosure provides an isolated polynucleotide comprising a nucleotide sequence having at least 95% sequence identity to the nucleotide sequence of SEQ ID NO:3. In some embodiments, the isolated polynucleotide comprises a nucleotide sequence having at least 96%, at least 97%, at least 98%, or at least 99% sequence identity to the nucleotide sequence of SEQ ID NO:3. In some embodiments, the isolated polynucleotide comprises the nucleotide sequence of SEQ ID NO:3.

In another aspect, the disclosure provides a lentiviral transfer vector comprising a promoter operably linked to a codon-optimized human CFTR gene, wherein expression of the codon-optimized human CFTR gene in cystic fibrosis human airway epithelial cells results in an increase in transepithelial $Cl^-$ transport compared to wild-type human CFTR. In some embodiments, the lentiviral transfer vector comprises a promoter operably linked to any one of the polynucleotides described herein.

In another aspect, the disclosure provides a lentiviral transfer vector comprising a promoter operably linked to any one of the polynucleotides described herein. In some embodiments, the promoter is a human phosphoglycerate kinase promoter (PGK). In some embodiments, the PGK promoter has at least 95% (e.g., at least 96%, at least 97%, at least 98%, at least 99% sequence identity to the nucleotide sequence of SEQ ID NO:4. In some embodiments, the promoter is a human elongation factor 1-α (EF1α) promoter. In some embodiments, the EF1α promoter has at least 95% (e.g., at least 96%, at least 97%, at least 98%, or at least 99%) sequence identity to the nucleotide sequence of SEQ ID NO:5.

In another aspect, the disclosure provides a lentiviral transfer vector including an EF1α promoter operably linked to a human CFTR gene. In some embodiments, the EF1α promoter has at least 95% (e.g., at least 96%, at least 97%, at least 98%, or at least 99%) sequence identity to the nucleotide sequence of SEQ ID NO:5.

In another aspect, the disclosure provides a lentiviral transfer vector comprising a promoter operably linked to a polynucleotide comprising a nucleotide sequence having at least 95% (e.g., at least 96%, at least 97%, at least 98%, at least 99%) sequence identity to the nucleotide sequence of SEQ ID NO:2. In some embodiments, the polynucleotide comprises the nucleotide sequence of SEQ ID NO: 2.

In some embodiments of any of the preceding aspects, the lentiviral components of the lentiviral vector originate from HIV-1. In some embodiments, the lentiviral vector further comprises one or more of a 5' long terminal repeat (LTR), a 3' LTR, a packaging signal, a Rev response element (RRE), a central polypurine tract (cPPT) sequence, and/or a central termination sequence (CTS).

In some embodiments of any of the preceding aspects, the 3' LTR is a self-inactivating 3' LTR. In some embodiments, the 3' LTR comprises an insertion of a human ankyrin 1 element in the reverse orientation. In some embodiments, the 3' LTR comprises a polynucleotide sequence having at least 95% sequence identity to the nucleotide sequence of SEQ ID NO:13. In some embodiments, the 3' LTR comprises the polynucleotide sequence of SEQ ID NO:13.

In another aspect, the disclosure provides a virion comprising any one of the lentiviral vectors described herein.

In another aspect, the disclosure provides a pharmaceutical composition comprising a pharmaceutically acceptable carrier and any one of the isolated polynucleotides, the lentiviral vectors, or virions described herein.

In another aspect, the disclosure provides a method of treating, or preventing or inhibiting one or more symptoms of, cystic fibrosis comprising administering to a subject in need thereof a therapeutically effective amount of any one of the isolated polynucleotides, the lentiviral vectors, the virions, or the pharmaceutical compositions described herein. In some embodiments, the method further comprises administering one or more additional therapeutic agents to the subject. In some embodiments, the one or more additional therapeutic agents includes an antibiotic, a mucus thinner, a CFTR modulator, a mucolytic, normal saline, hypertonic saline, or a combination thereof. In some embodiments, the administering is by inhalation, nebulization, atomization or via atomizer, aerosolization, intranasally, intratracheally, intrabronchially, orally, intravenously, subcutaneously, or intramuscularly. In some embodiments, administering is by inhalation, nebulization, atomization or via atomizer, aerosolization, intranasally, intratracheally, and/or intrabronchially.

In another aspect, the disclosure provides any one of the polynucleotides, the lentiviral vectors, the virions, or the pharmaceutical compositions described herein for use in treating, or preventing or inhibiting one or more symptoms of, cystic fibrosis. In some embodiments, any one of the polynucleotides, the lentiviral vectors, the virions, or the pharmaceutical compositions described herein for use in treating cystic fibrosis is administered in combination with one or more additional therapeutic agents. In some embodiments, the one or more additional therapeutic agents includes an antibiotic, a mucus thinner, a CFTR modulator, a mucolytic, normal saline, hypertonic saline, or a combination thereof. In some embodiments, any one of the polynucleotides, the lentiviral vectors, the virion, or the pharmaceutical composition described herein is to be administered by inhalation, nebulization, atomization or via atomizer, aerosolization, intranasally, intratracheally, intrabronchially, orally, intravenously, subcutaneously, or intramuscularly. In some embodiments, any one of the polynucleotides, the lentiviral vectors, the virions, or the pharmaceutical compositions described herein is to be administered by inhalation, nebulization, atomization or via atomizer, aerosolization, intranasally, intratracheally, and/or intrabronchially.

In another aspect, the disclosure provides an atomizer sprayer or nebulizer comprising any one of the isolated polynucleotides, the lentiviral vectors, the virions, or the pharmaceutical compositions described herein.

BRIEF DESCRIPTION OF THE DRAWINGS

FIG. 1B also shows codon usage by CFTR domain for coCFTR2 (SEQ ID NO: 1) and coCFTR3 (SEQ ID NO: 2).

FIG. 4E shows the short-circuit current change (Alsc) in response to F&I and GlyH that was calculated and showed no significant difference between the two vectors observed at any dose. The points on the graph represent the average of 1-3 epithella. Each donor is represented by a unique symbol and the mean #SE are shown.

FIG. 5A is a schematic representation of three versions of vectors used including the promoter human phosphoglycerate kinase (PGK) to drive transgene expression, a human ankyrin 1 (Ank) insulator element in the reverse orientation present within the self-inactivating (SIN) 3' LTR, and a transgene of wildtype (WT) CFTR, codon optimized CFTR version 3 (coCFTR3), or GFP. The vectors shown are not to scale.

FIG. 5B is a schematic representation of two versions of vectors used including the promoter human elongation factor 1-α (EF1α) to drive transgene expression, an Ank insulator element in the reverse orientation present within the SIN 3' LTR, and a transgene of WT CFTR, coCFTR3, or GFP. The vectors shown are not to scale.

(FIG. 6A) Three days post transfection, cell lysate was collected and CFTR was quantified by western blot. The same representative blot is shown with normal exposure (top) and with overexposure of the CFTR channel (bottom) to visualize WT CFTR. Similarly, FRT cells were electroporated with the same plasmids, seeded on semipermeable membranes and allowed to form an epithelial layer under air-liquid interface culture conditions. (FIG. 6B) Epithella were mounted in Ussing chambers and changes in transepithelial Cl— current (DIT) in response to an apical low CI-gradient, CFTR activation by F&I, and CFTR inhibition by GlyH were calculated. (FIG. 6C) The baseline transepithelial electrical resistance (TEER) was quantified. No significant differences in TEER were observed between any of the treatment groups. Mean±SE are shown.

(FIG. 7A) After four weeks of differentiation under air-liquid interface culture conditions, pseudostratified ciliated columnar epithelia were observed. Scale bars represent 20 μm. (FIG. 7B) The baseline transepithelial electrical resistance (TEER) of epithelia studied in Ussing chambers was quantified and no significant differences were observed between any of the treatment groups. Mean #SE are shown.

DETAILED DESCRIPTION

Definitions

Figures 1A, 1B, 1C, 1D:
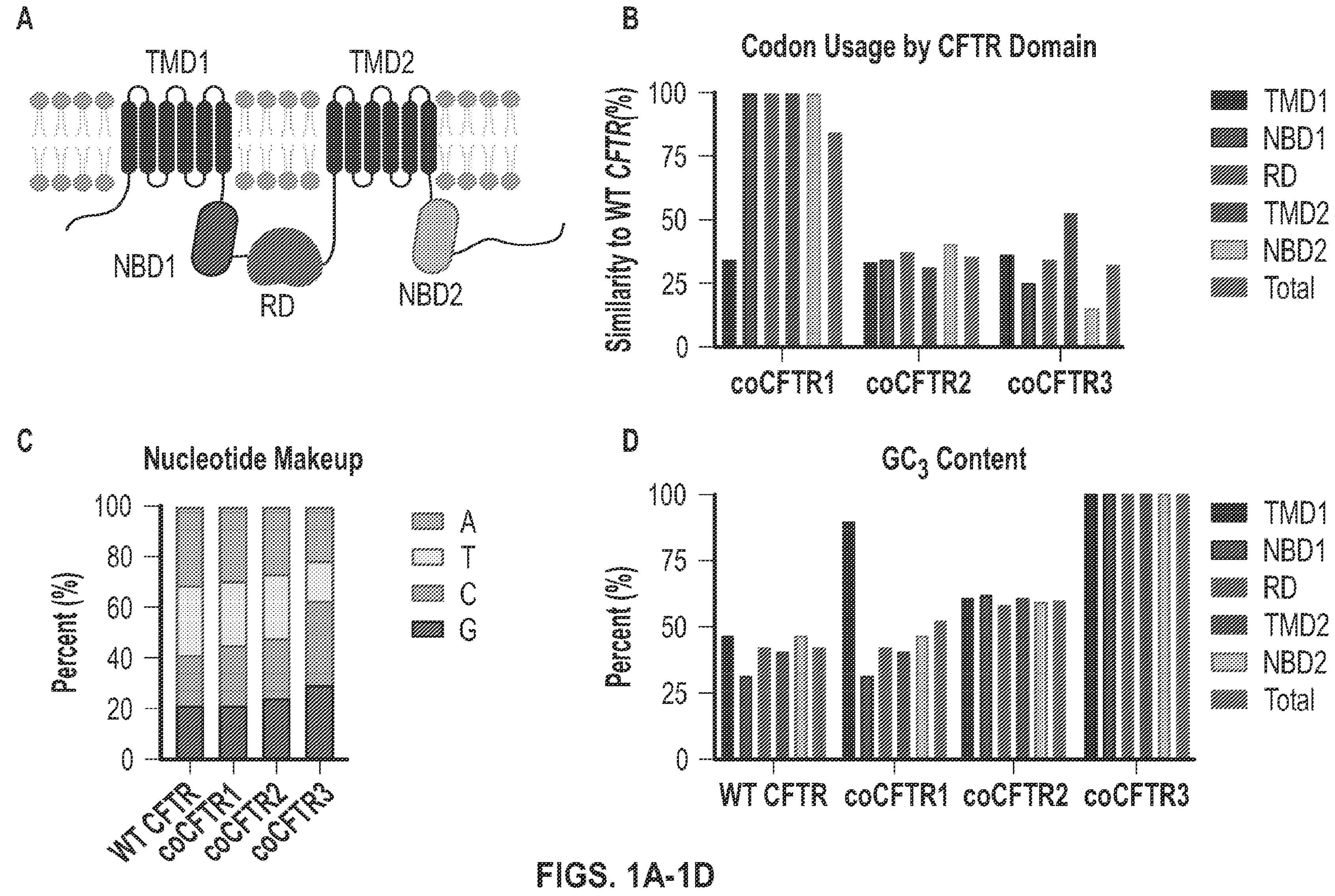
FIG. 1A is a schematic diagram showing the five distinct protein domains of CFTR including two transmembrane domains (TMD1 and TMD2), two nucleotide binding domains (NBD1 and NBD2), and a regulatory domain (RD).
FIG. 1B is a graph showing codon optimization of the transmembrane domain 1 (TMD1) of coCFTR1. The remaining domains, including nucleotide binding domains 1 and 2 (NBD1/2), regulatory domain (RD), and transmembrane domain 2 (TMD2), retained the wildtype (WT) sequence.
FIG. 1C is a graph showing the percentage of nucleotides that are C, G. A, and T in WTCFTR, coCFTR1, coCFTR2 (SEQ ID NO: 1), and coCFTR3 (SEQ ID NO: 2).
FIG. 1D is a graph showing the percent of $GC_3$ content for WTCFTR, coCFTR1, coCFTR2 (SEQ ID NO: 1), and coCFTR3 (SEQ ID NO: 2) in the TMD1, NBD1, RD, NBD2, and TMD2 domains.

As used herein, a "5' LTR" refers to a long terminal repeat (LTR) sequence that is located in a 5' relationship to a transgene. The 5' LTR and 3' LTR facilitate integration of lentiviral transfer vector sequences into a host genome. Typically, the sequences between and including the LTRs are integrated into the host genome upon viral transduction. The 5' LTR of a wild-type HIV-1 virus includes, from 5'-to-3', a U3 region, an R region, and a U5 region. A wild-type, HIV-1 5' LTR can act as a relatively weak, Tat-dependent promoter if a separate transgene promoter is not provided. A 5' LTR may lack a U3 region (e.g., the U3 region may be deleted). For example, a chimeric 5' LTR that is fused to a heterologous promoter (e.g., a viral promoter such as a CMV promoter or an RSV promoter) can be used. The heterologous promoter may replace the U3 region of the 5' LTR.

The term "about" is used herein to mean a value that is ±10% of the recited value.

As used herein, by "administering" is meant a method of giving a dosage of a composition described herein (e.g., a polynucleotide, a lentiviral vector, virion, or a pharmaceutical composition thereof) to a subject. The compositions utilized in the methods described herein can be administered by any suitable route, including, for example, by inhalation, nebulization, aerosolization, intranasally, intratracheally, intrabronchially, orally, parenterally (e.g., intravenously, subcutaneously, or intramuscularly), orally, nasally, rectally, topically, or buccally. A composition described herein may be administered in aerosolized particles intratracheally and/or intrabronchially using an atomizer sprayer (e.g., with a MADgic® laryngo-tracheal mucosal atomization device) or a nebulizer. The compositions utilized in the methods described herein can also be administered locally or systemically. In one embodiment, the method of administration may vary depending on various factors (e.g., the components of the composition being administered, and the severity of the condition being treated).

The term "codon optimization" refers to modifying a nucleic acid sequence to change individual nucleic acids (e.g., relative to wildtype or another reference sequence) without any resulting change in the sequence of the encoded amino acid. The resulting nucleic acid sequence may be referred to as a "codon optimized" sequence. This process may be performed on any of the sequences described herein to enhance expression or stability. Codon optimization may be performed using any suitable approach, e.g., any approach described in, e.g., U.S. Pat. Nos. 7,561,972, 7,561,973, and 7,888,112, each of which is incorporated herein by reference in its entirety. Computer algorithms for codon optimizing a particular sequence for expression in a particular host cell are also available, such as Gene Forge (Aptagen; Jacobus, PA), JCat (jcat.de), or Benchling (Broad Institute). Alternative algorithms for codon optimization are available from IDT, Genscript, GeneArt, and Twist Bioscience.

A "control element" or "control sequence" is a nucleotide sequence involved in an interaction of molecules that contributes to the functional regulation of a polynucleotide, including replication, duplication, transcription, splicing, translation, or degradation of the polynucleotide. Regulation by the control element may affect the frequency, speed, or specificity of the process, and may be enhancing or inhibitory in nature. Control elements known in the art include, for example, transcriptional regulatory sequences such as promoters and enhancers. A promoter is a DNA region capable, under certain conditions, of binding RNA polymerase and initiating transcription of a coding region usually located downstream (in the 3' direction) from the promoter.

A "detectable marker gene" is a gene that allows cells carrying the gene to be specifically detected (e.g., distinguished from cells which do not carry the marker gene). A large variety of such marker genes are known in the art (e.g., lacZ, luciferase, chloramphenicol acetyltransferase, and a fluorescent protein (e.g., green fluorescent protein (GFP), red fluorescent protein (RFP), mCherry, dsRed, cyan fluorescent protein (CFP), yellow fluorescent protein (YFP), or any other fluorescent protein known in the art).

An "expression vector" is a vector comprising a region which encodes a polypeptide or RNA of interest and is used for affecting the expression of the protein or RNA in an intended target cell. An expression vector also has control elements operatively linked to the encoding region to facilitate expression of the product in the target cell. The combination of control elements and a gene, or genes, to which they are operably linked for expression is sometimes referred to as an "expression cassette," a large number of which are known and available in the art or can be readily constructed from components that are available in the art.

A "gene" refers to a polynucleotide containing at least one open reading frame that is capable of encoding a particular protein after being transcribed and translated.

The terms "gene delivery" and "gene transfer" refer to the introduction of an exogenous polynucleotide into a cell which may encompass targeting, binding, uptake, transport, localization, replicon integration, and/or expression of the gene.

The term "gene expression" or "expression" refers to the process of gene transcription, translation, and/or post-translational modification.

"Heterologous" means derived from an entity that is genotypically distinct from the rest of the entity to which it is compared. For example, a polynucleotide introduced by genetic engineering techniques into a different cell type is a heterologous polynucleotide, and, when expressed, can encode a heterologous polypeptide.

"Host cells," "cell lines," "cell cultures," "packaging cell line," and other such terms denote eukaryotic cells, e.g., mammalian cells, such as human cells, useful in the present disclosure that are used as recipients for recombinant vectors, viruses, or other transfer polynucleotides, and include the progeny of the original cell that was transduced. It is understood that the progeny of a single cell may not necessarily be completely identical (in morphology or in genomic complement) to the original parent cell.

An "isolated" plasmid, virus, or other substance refers to a preparation of the substance devoid of at least some of the other components that may be present where the substance of a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering, substance present in the source mixture.

As used herein, the term "lentivirus" refers to a genus of the Retroviridae family of viruses that typically gives rise to a slowly developing disease. Viruses included within this group include HIV (human immunodeficiency virus; including HIV type 1 and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which causes immune deficiency and encephalopathy in sub-human primates. Diseases caused by these viruses are typically characterized by a long incubation period and protracted course. Usually, the viruses latently infect monocytes and macrophages from which they spread to other cells. HIV, FIV, and SIV also readily infect T lymphocytes (i.e., T-cells).

The term "lentiviral vector" refers to a vector including one or more nucleic acid sequences that are derived from at least a portion of a lentivirus genome. A lentiviral vector may contain non-coding sequences of one or more proteins from a lentivirus (e.g., HIV-1).

A "lentiviral transfer vector" is a lentiviral vector that includes a heterologous nucleic acid sequence to be transferred into a cell, (e.g., a transgene, including a therapeutic transgene, e.g., a CFTR gene, including a human CFTR gene, which may be a codon optimized CFTR gene), as well as, one or more lentiviral genes, or portions thereof. The term encompasses any type of lentiviral transfer vector, including, without limitation, second generation lentiviral transfer vectors (in which transgene expression is driven by the 5' LTR in a Tat-dependent manner) and third generation lentiviral transfer vectors (in which transgene expression is driven by a chimeric 5' LTR fused to a heterologous promoter on the transfer plasmid), as well as any modified versions of such lentiviral transfer vectors.

A "lentiviral packaging vector" is a lentiviral vector which includes one or more genes encoding the lentiviral proteins Gag, Pol, or Rev, or portions thereof. For example, in second generation lentiviral packaging systems, the lentiviral packaging vector includes genes encoding the lentiviral proteins Gag, Pol, Rev, and Tat, or portions thereof, on a single plasmid. In third generation lentiviral packaging systems, the genes encoding the Gag and Pol lentiviral proteins, or portions thereof, are included on a single plasmid, while the gene encoding the lentiviral protein Rev, or a portion thereof, is included on a separate plasmid, and the gene encoding the lentiviral protein Tat is eliminated. Transfection of host cells with a transfer vector and one or more packaging vectors can be carried out in order to produce a virus, which can be used to infect target cells thus leading to expression of one or more transgenes.

As used herein, the term "operable linkage" or "operably linked" refers to a physical or functional juxtaposition of the components so described as to permit them to function in their intended manner. More specifically, for example, two DNA sequences operably linked means that the two DNAs are arranged (cis or trans) in such a relationship that at least one of the DNA sequences is able to exert a physiological effect upon the other sequence. For example, an enhancer and/or a promoter can be operably linked with a transgene (e.g., a therapeutic transgene, such as a CFTR gene, or a codon optimized version thereof).

"Packaging" as used herein refers to a series of subcellular events that result in the assembly and encapsidation of a viral vector, particularly a lentiviral vector. Thus, when a suitable vector is introduced into a packaging cell line under appropriate conditions, it can be assembled into a viral particle (also referred to herein as a "virion"). Functions associated with packaging of viral vectors, particularly lentiviral vectors, are described herein and in the art.

"Percent (%) sequence identity," with respect to a reference polynucleotide or polypeptide sequence, is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction X/Y)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

The terms "polynucleotide" and "nucleic acid" are used interchangeably to refer to a polymeric form of nucleotides of any length, including deoxyribonucleotides, ribonucleotides, or analogs thereof. A polynucleotide may include modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the disclosure described herein that is a double-stranded polynucleotide encompasses both the double-stranded form and each of the two complementary single-stranded forms known or predicted to make up the double-stranded form.

The terms "polypeptide" and "protein" are used interchangeably herein to refer to polymers of amino acids of any length. The terms also encompass an amino acid polymer that has been modified; for example, by disulfide bond formation, glycosylation, acetylation, phosphorylation, lipidation, or conjugation with a labeling component. Polypeptides such as "CFTR" and the like, when discussed in the context of gene therapy and compositions therefor, refer to the respective intact polypeptide, or any fragment or genetically engineered derivative thereof that retains the desired biochemical function of the intact protein. Similarly, references to CFTR, and other such genes for use in gene therapy (typically referred to as "transgenes" to be delivered to a recipient cell), include polynucleotides encoding the intact polypeptide or any fragment or genetically engineered derivative possessing the desired biochemical function.

By "pharmaceutical composition" is meant any composition that contains a therapeutically or biologically active agent (e.g., a polynucleotide comprising a transgene (e.g., a CFTR gene, such as a codon optimized CFTR gene)), either incorporated into a viral vector (e.g., a recombinant lentiviral vector) or independent of a viral vector (e.g., incorporated into a liposome, microparticle, or nanoparticle) that is suitable for administration to a subject. Any of these formulations can be prepared by well-known and accepted methods in the art. See, for example, Remington: The Science and Practice of Pharmacy (21st ed.), ed. A.R. Gennaro, Lippincott Williams & Wilkins, 2005, and Encyclopedia of Pharmaceutical Technology, ed. J. Swarbrick, Informa Healthcare, 2006, each of which is hereby incorporated by reference.

By "pharmaceutically acceptable diluent, excipient, carrier, or adjuvant" is meant a diluent, excipient, carrier, or adjuvant which is physiologically acceptable to the subject while retaining the therapeutic properties of the pharmaceutical composition with which it is administered.

As used herein, an "R region" refers to a region within a long terminal repeat (LTR) located between the U3 and U5 regions, which includes repeat sequences from the viral RNA genome (e.g., HIV-1 genome). The length of the R region varies significantly among retroviruses, ranging from 16 nucleotides to 228 nucleotides. The R region in lentiviruses is typically between about 100 and 200 nucleotides in length. In wild-type lentiviruses, the 5' end of the R region on the 5' LTR is the site of transcript initiation of the provirus, which is then terminated at the 3' end of the R region on the 3' LTR, and, as a result, the R region may be required for transcription in the context of wild-type lentiviruses. Second-generation lentiviral vectors may include a 5' LTR R region that includes a Trans-activating response element (TAR) that acts as a binding site for Tat.

"Recombinant," as applied to a polynucleotide, means that the polynucleotide is the product of various combinations of cloning, restriction, and/or ligation steps, and/or other procedures that result in a construct that is distinct from a polynucleotide found in nature (e.g., gene synthesis). A recombinant virus is a viral particle comprising a recombinant polynucleotide. The terms respectively include replicates of the original polynucleotide construct and progeny of the original virus construct.

By "recombinant lentivirus" or "recombinant lentiviral vector" is meant a recombinantly produced lentivirus or lentiviral particle that comprises a polynucleotide sequence not of lentiviral origin (e.g., a polynucleotide comprising a transgene, which may be operably linked to one or more enhancer and/or promoters) such vectors may be delivered into a cell, either in vivo, ex vivo, or in vitro. The recombinant lentivirus may use naturally occurring capsid proteins from any lentiviral serotype. In some embodiments, the lentivirus is pseudotyped.

By "reference" is meant any sample, standard, or level that is used for comparison purposes. A "normal reference sample" or a "wild-type reference sample" can be, for example, a sample from a subject not having the disorder (e.g., cystic fibrosis). A "positive reference" sample, standard, or value is a sample, standard, value, or number derived from a subject that is known to have a disorder (e.g., cystic fibrosis), which may be matched to a sample of a subject by at least one of the following criteria: age, weight, disease stage, and overall health. A "reference sequence" may be any sequence used for comparison purposes, e.g., a wild-type sequence (e.g., a wild-type CFTR sequence).

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. A variety of positive and negative selectable markers are known in the art.

The terms "subject" and "patient" are used interchangeably herein to refer to any mammal (e.g., a human, a primate, a cat, a dog, a ferret, a cow, a horse, a pig, a goat, a rat, or a mouse). In one embodiment, the subject is a human.

A "terminator" refers to a polynucleotide sequence that tends to diminish or prevent read-through transcription (i.e., it diminishes or prevents transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences" are specific sequences that tend to disrupt read-through transcription by RNA polymerase, presumably by causing the RNA polymerase molecule to stop and/or disengage from the DNA being transcribed. Typical example of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators) and may be comprised of sequence-specific termination sequences or sequence-non-specific terminators or both. A variety of such terminator sequences are known in the art; and illustrative uses of such sequences within the context of the present disclosure are provided below.

As used herein, the term "U3 region" refers to the 5' region of a long terminal repeat (LTR) sequence and includes a core enhancer, a long modulatory region, which may influence viral gene expression, and a basal promoter, which has the TATA box located about 25 nucleotides from the beginning of the R region. These components found in the U3 region make it essential for viral replication.

As used herein, the term "U5 region" refers to the 3' region of a long terminal repeat (LTR) sequence, following the U3 region and the R region; it is derived from the 5' terminus of the viral RNA genome (e.g., HIV-1). The U5 region contains a U5-IR stem-loop structure which interacts with the IRNA replication primer to control initiation of the minus-strand. Additionally, the U5 region plays a role in terminating transcription.

As used herein, a "self-inactivating 3' LTR" refers to a 3' LTR which lacks LTR promoter activity, and, as a result, a viral plasmid containing a self-inactivating LTR is not capable of undergoing replication. The self-inactivating 3' LTR can be generated by deleting the U3 region of the 3' LTR to remove the TATA box, thus preventing the initiation of transcription. In some embodiments, the 3' LTR comprises an insertion of a human ankyrin 1 element, e.g., in the reverse orientation.

A "therapeutic gene," "prophylactic gene," "target polynucleotide," "transgene," "gene of interest," and the like generally refer to a heterologous gene, or genes, that is transferred into a target cell, for example, using a lentiviral transfer vector of the disclosure. Typically, in the context of the present disclosure, such genes are located within the recombinant lentiviral transfer and are flanked by long terminal repeat (LTR) regions, and thus can be replicated and encapsidated into lentiviral particles. Exemplary transgenes include, without limitation, a codon optimized cystic fibrosis transmembrane conductance regulator (CFTR), or derivatives or fragments thereof possessing the desired biochemical function. To effect expression of the transgene in a recipient host cell, it may be operably linked to a promoter, either its own or a heterologous promoter (e.g., a PGK promoter or an EF1α promoter). A large number of suitable promoters are known in the art, the choice of which depends on the desired level of expression of the target polynucleotide, such as whether one desires constitutive expression, inducible expression, cell-specific or tissue-specific expression, etc. In addition to the coding region for the gene product, the transgene may include or be operably linked to one or more elements to facilitate or enhance expression, such as a promoter, enhancer(s), destabilizing domain(s), response element(s), reporter element(s), insulator element(s), polyadenylation signal(s), and/or other functional elements. Embodiments of the disclosure may utilize any known suitable promoter (e.g., a PGK promoter or an EF1α promoter), enhancer(s), destabilizing domain(s), response element(s), reporter element(s), insulator element(s), polyadenylation signal(s), and/or other functional elements.

By "therapeutically effective amount" is meant the amount of a composition administered to improve, inhibit, or ameliorate a condition of a subject, or a symptom of a disorder or disease, e.g., cystic fibrosis, in a clinically relevant manner. Any improvement in the subject is considered sufficient to achieve treatment. In one embodiment, an amount sufficient to treat is an amount that reduces, inhibits, or prevents the occurrence or one or more symptoms of the disease or disorder (e.g., cystic fibrosis) or is an amount that reduces the severity of, or the length of time during which a subject suffers from one or more symptoms of the disease or disorder, for example, cystic fibrosis, (e.g., by at least about 10%, about 20%, or about 30%, by at least about 50%, about 60%, or about 70%, or by at least about 80%, about 90%, about 95%, about 99%, or more, relative to a control subject that is not treated with a composition described herein). An effective amount of the pharmaceutical composition used to practice the methods described herein (e.g., the treatment of cystic fibrosis) varies depending upon the manner of administration and the age, body weight, and general health of the subject being treated. A physician or researcher can decide the appropriate amount and dosage regimen.

"Transduction" or "transducing" as used herein, are terms referring to a process for the introduction of an exogenous polynucleotide, e.g., a transgene in a recombinant lentiviral vector, into a host cell leading to expression of the polynucleotide, e.g., the transgene in the cell. The process generally includes 1) endocytosis of the lentiviral vector after it has bound to a cell surface receptor, 2) escape from endosomes or other intracellular compartments in the cytosol of a cell, 3) trafficking of the viral particle or viral genome to the nucleus, 4) uncoating of the virus particles, and generation of expressible double stranded lentiviral genome forms, including circular intermediates. The lentiviral vector in an expressible double stranded form may persist as a nuclear episome or may integrate into the host genome. The alteration of any or a combination of endocytosis of the lentiviral vector after it has bound to a cell surface receptor, escape from endosomes or other intracellular compartments to the cytosol of a cell, trafficking of the viral particle or viral genome to the nucleus, or uncoating of the virus particles, and generation of expressive double stranded lentiviral genome forms, including circular intermediates, may result in altered expression levels or persistence of expression, or altered trafficking to the nucleus, or altered types or relative numbers of host cells or a population of cells expressing the introduced polynucleotide. Altered expression or persistence of a polynucleotide introduced via a lentiviral vector can be determined by methods well known to the art including, but not limited to, protein expression, e.g., by ELISA, flow cytometry and Western blot, measurement of and DNA and RNA production by hybridization assays, e.g., Northern blots, Southern blots and gel shift mobility assays.

"Treatment" of an individual or a cell is any type of intervention in an attempt to alter the natural course of the individual or cell at the time the treatment is initiated, e.g., eliciting a prophylactic, curative or other beneficial effect in the individual. For example, treatment of an individual may be undertaken to decrease or limit the pathology caused by any pathological condition, including (but not limited to) an inherited or induced genetic deficiency (e.g., cystic fibrosis). Treatment includes (but is not limited to) administration of a composition, such as a pharmaceutical composition, and administration of compatible cells that have been treated with a composition. Treatment may be performed either prophylactically or therapeutically; that is, either prior or subsequent to the initiation of a pathologic event or contact with an etiologic agent. Treatment may reduce one or more symptoms of a pathological condition. For example, symptoms of cystic fibrosis are known in the art and include, e.g., persistent cough, wheezing, breathlessness, exercise intolerance, repeated lung infections, inflamed nasal passages or stuffy nose, foul-smelling or greasy stools, poor weight gain and growth, intestinal blockage, constipation, elevated salt concentrations in sweat, pancreatitis, and pneumonia. Detecting an improvement in, or the absence of, one or more symptoms of a disorder (e.g., cystic fibrosis), indicates successful treatment.

A "variant" refers to a polynucleotide or a polypeptide that is substantially homologous to a native or reference polynucleotide or polypeptide. For example, a variant polynucleotide is substantially homologous to a native or reference polynucleotide but has a polynucleotide sequence different from that of the native or reference polynucleotide because of one or a plurality of deletions, insertions, and/or substitutions. In another example, a variant polypeptide is substantially homologous to a native or reference polypeptide but has an amino acid sequence different from that of the native or reference polypeptide because of one or a plurality of deletions, insertions, and/or substitutions. Variant polypeptide sequences encoding polynucleotide sequences encompass sequences that comprise one or more additions, deletions, or substitutions of nucleotides when compared to a native or reference polynucleotide sequence, that encode a variant protein or fragment thereof that retains activity. A wide variety of mutagenesis approaches are known in the art and can be applied by a person of ordinary skill in the art. A variant polynucleotide or polypeptide sequence can be at least 80%, at least 85%, at least at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a variant sequence can be determined, for example, by comparing the two sequences using freely available computer programs commonly employed for this purpose on the world wide web (e.g., BLASTp or BLASTn with default settings).

A "vector" as used herein refers to a macromolecule or association of macromolecules that comprises or associates with a polynucleotide and which can be used to mediate delivery of the polynucleotide to a cell, either in vitro or in vivo. Illustrative vectors include, for example, plasmids, viral vectors, liposomes, and other gene delivery vehicles. The polynucleotide to be delivered may include a coding sequence of interest in gene therapy (such as a gene encoding a protein of therapeutic interest), a coding sequence of interest in vaccine development (such as a polynucleotide expressing a protein, polypeptide or peptide suitable for eliciting an immune response in a mammal), and/or a selectable or detectable marker.

Polynucleotides

The disclosure provides polynucleotides that include transgenes, which, for example, may be incorporated as transgenes into a viral vector (e.g., a lentiviral vector), or used in the preparation of a viral vector (e.g., a lentiviral vector). The transgene may be a therapeutic transgene. In some embodiments, the polynucleotide is a therapeutic transgene for the treatment of cystic fibrosis. In some embodiments, the polynucleotide is a codon-optimized transgene.

In one aspect, the disclosure provides an isolated polynucleotide that includes the sequence of SEQ ID NO: 1, or a sequence having at least 95%, 96%, 97%, 98%, or 99% sequence identity with the polynucleotide sequence of SEQ ID NO: 1.

In another aspect, the disclosure provides an isolated polynucleotide comprising the sequence of SEQ ID NO: 2, or a sequence having at least 95%, 96%, 97%, 98%, or 99% sequence identity with the polynucleotide sequence of SEQ ID NO: 2.

In another aspect, the disclosure provides an isolated polynucleotide that includes the sequence of SEQ ID NO: 3, or a sequence having at least 95%, 96%, 97%, 98%, or 99% sequence identity with the polynucleotide sequence of SEQ ID NO: 3.

Any of the polynucleotides described herein may be incorporated into a lentiviral vector. Any suitable lentiviral vector may be used. Any of the polynucleotides may contain a 5' LTR. Any suitable 5' LTR may be used. Any of the polynucleotides may contain a 3' LTR. Any suitable 3' LTR may be used. In some embodiments, the 3' LTR is a self-inactivating 3' LTR. In some embodiments, the 3' LTR comprises an insertion of a human ankyrin 1 element in the reverse orientation. In some embodiments, the 3' LTR comprises a polynucleotide sequence having at least 95%, 96%, 97%, 98%, or 99% sequence identity to the nucleotide sequence of SEQ ID NO:13. In some embodiments, the 3' LTR comprises the polynucleotide sequence of SEQ ID NO:13.

Any of the polynucleotides may contain an enhancer or a post-transcriptional regulatory element (e.g., WPRE or HPRE). Any of the polynucleotides may contain a promoter (e.g., a human PGK-1 promoter, a CMV promoter, an RSV promoter, an EF1α promoter). Any suitable promoter may be used. In some embodiments, the promoter may be a human PGK-1 promoter. In particular embodiments, the promoter may be an EF1α promoter.

Any of the polynucleotides may contain a polyadenylation site (e.g., a bGH polyA site, a SV40 polyA site). Any suitable polyadenylation site may be used. The polynucleotide may also contain one or more detectable markers. A variety of such markers are known, including, by way of illustration, the bacterial beta-galactosidase (lacZ) gene; the human placental alkaline phosphatase (AP) gene, and genes encoding various cellular surface markers which have been used as reporter molecules both in vitro and in vivo. The polynucleotide may also contain one or more selectable markers.

Further, the polynucleotides of the disclosure may include any one or more of these elements.

Lentivirus and Lentiviral Vector Systems

The disclosure provides polynucleotides which may be incorporated into lentiviral vectors as part of a lentiviral vector system. Lentiviruses are a subtype of the Retroviridae family, including human immunodeficiency virus (HIV), simian immunodeficiency virus (SIV), feline immunodeficiency virus (FIV), and equine infectious anemia virus (EIAV), that depend on several viral regulatory genes in addition to the simple structural gag-pol-env genes for efficient intracellular replication. Thus, lentiviruses use more complex strategies than classical retroviruses for gene regulation and viral replication, with packaging signals apparently spreading across the entire viral genome. These additional genes display a web of regulatory functions during the lentiviral life cycle. For example, upon HIV-1 infection, transcription is up-regulated by the expression of Tat through interaction with an RNA target (TAR) in the LTR. Expression of the full-length and spliced mRNAs is then regulated by the function of Rev, which interacts with RNA elements present in the gag region and in the env region at the Rev response element (RRE) (Schwartz et al., J. Virol., 66:150-159 (1992)). Nuclear export of gag-pol and env mRNAs is dependent on the Rev function. In addition to these two essential regulatory genes, Tat and Rev, a list of accessory genes, including vif, vpr, vpx, vpu, and nef, are also present in the viral genome and their effects on efficient virus production and infectivity have been demonstrated, although they are not absolutely required for virus replication (Wong-Staal et al., Microbial. Rev., 55:193-205 (1991); Subbramanian et al., J. Virol. 68:6831-6835 (1994); and Trone, Cell 82:189-192 (1995)). A detailed description of the structure of an exemplary lentivirus, HIV-1, is given in U.S. Pat. No. 6,531,123.

A vector used in the methods and compositions described herein may be a retroviral vector, such as a lentiviral vector. Lentiviruses have advantages as gene transfer vectors, as they can carry 7-8 kb, can infect cells, and have their genetic material stably integrated into the host cell with high efficiency (see, e.g., WO 95/30761 and WO 95/24929). In one embodiment, a lentiviral vector is replication-defective to prevent further generation of infectious lentiviral particles in the target tissue. Thus, the replication-defective virus becomes a captive transgene stably incorporated into the target cell genome. Replication-defective lentiviral vectors are commonly achieved by dividing the essential viral proteins for replication on to separate plasmids, including the ψ packaging signal only on the vector containing the transgene, and by deleting the majority of the viral genes, keeping only those that are necessary or advantageous. In place of the deleted viral genes, heterologous nucleic acids can be inserted. The heterologous genes may be under the control of an endogenous heterologous promoter, a different heterologous promoter active in the target cell, or the retroviral 5' LTR. In particular embodiments, the heterologous genes are under the control of an EF1α promoter. In certain embodiments, the heterologous genes are under the control of a human PGK-1 promoter.

Lentiviral vectors transduce a wide range of dividing and non-dividing cell types with high efficiency, conferring stable, long-term expression of the transgene. An overview of optimization strategies for packaging and transducing lentiviral vectors is provided in Delenda, The Journal of Gene Medicine 6: S125 (2004). The use of lentivirus-based gene transfer techniques typically involves in vitro production of recombinant lentiviral particles carrying an engineered viral genome in which the transgene of interest is introduced. In particular, the recombinant lentivirus can be recovered through the trans co-expression in a permissive cell line of (1) the packaging constructs, i.e., a vector expressing the Gag-Pol precursors and a vector expressing Rev; (2) a vector expressing an envelope protein, which may be a heterologous envelope protein; and (3) the transfer vector, lacking the viral cDNA for all or substantially all open reading frames, but maintaining the sequences for replication, encapsidation, and expression, along with the sequences to be expressed (e.g., a transgene such as CFTR gene, including a codon-optimized version thereof).

The present disclosure contemplates a polynucleotide incorporated as a transgene into a lentiviral gene amplification and transfer system comprising a transgene vector, one or more compatible packaging vectors, an envelope vector, and a suitable host cell. The vectors used may be derived from a lentivirus. Lentivirus vectors allow (1) transfection of the packaging vectors and envelope vectors into the host cell to form a packaging cell line that produces essentially packaging-vector-RNA-free viral particles, (2) transfection of the transgene vector into the packaging cell line, (3) the packaging of the transgene vector RNA by the packaging cell line into infectious viral particles, and (4) the administration of the particles to target cells so that such cells are transduced and subsequently express a transgene.

Recombinant retroviral (e.g., lentiviral) particles can be administered directly to the subject, in vivo, or the subject's cells may be removed, infected in vitro with the particles, and returned to the body of the subject. The packaging vectors and transgene vectors of the present disclosure will generate replication-incompetent viruses. The vectors chosen for incorporation into a given vector system of the present disclosure are such that it is not possible, without further mutation of the packaging vector(s) or transgene vector, for the co-transfected cells to generate a replication-competent virus by homologous recombination of the packaging vector(s) and transgene vector alone. The envelope protein used in the present system can be a retroviral envelope, a synthetic or chimeric envelope, or the envelope from a non-retroviral enveloped virus (e.g., *Autographa californica*). Methods for preparation and in vivo administration of lentiviruses are described in U.S. 20020037281.

Packaging Vectors

Any of the lentiviral transfer vectors provided herein may be co-transfected into a cell with one or more additional vectors. In some instances, the one or more additional vectors may include lentiviral packaging vectors. In certain instances, the one or more additional plasmids may include an envelope plasmid (e.g., an envelope plasmid encoding GP64). Generally, a packaging vector includes one or more polynucleotide sequences encoding lentiviral proteins (e.g., gag, pol, env, tat, rev, vif, vpu, vpr, and/or nef protein, or a derivative, combination, or portion thereof). A packaging vector to be co-transfected into a cell with a lentiviral transfer vector of the disclosure and includes sequence(s) encoding for one or more lentiviral proteins not encoded for by the lentiviral transfer vector. For example, a lentiviral transfer vector may be co-transfected with a first packaging vector encoding gag and pol and a second packaging vector encoding rev. Thus, co-transfection of a lentiviral transfer vector with such packaging vector(s) may result in the introduction of all genes for viral particle formation into the cell, thereby enabling the cell to produce viral particles that may be isolated. Appropriate packaging vectors for use in the disclosure can be selected by those of skill in the art. For examples of packaging vectors that can be used or adapted for use in the disclosure see, e.g., WO 03/064665, WO 2009/153563, U.S. Pat. No. 7,419,829, WO 2004/022761, U.S. Pat. No. 5,817,491, WO 99/41397, U.S. Pat. Nos. 6,924,123, 7,056,699, WO 99/32646, WO 98/51810, and WO 98/17815. In some instances, a packaging plasmid may encode a gag and/or pol protein, and may optionally include an RRE sequence (e.g., an pMDLgpRRE vector; see, e.g., Dull et al., J. Virol. 72 (11): 8463-8471, 1998). In certain instances, a packaging vector may encode a rev protein (e.g., a pRSV-Rev vector).

Any of the lentiviral vectors described herein may include one or more packaging signals. As used herein, the term "packaging signal" or "packaging sequence" refers to sequences located within the lentiviral genome or a vector that provides for, or at least facilitates, insertion of the viral or vector RNA into the viral capsid or particle. The term "packaging signal" is also used for convenience to refer to a vector DNA sequence that is transcribed into a functional packaging signal. Certain packaging signals may be part of a gene, but are recognized in the form of RNA, rather than as a peptide moiety of the encoded protein.

Envelope Proteins

Any suitable envelope protein may be used in the lentiviral vectors, virions, and other compositions (e.g., pharmaceutical compositions) described herein. An example of a non-lentiviral envelope protein of interest is the baculovirus *Autographa californica* multinuclear polyhedrosis virus (AcMNPV) envelope glycoprotein-64 (GP64). GP64 pseudotyped particles can be highly concentrated and, unlike the commonly used VSV-G envelope protein, are not cytotoxic to the cell. The vector containing an envelope protein that is different from the packaging virus genes is commonly referred to as an envelope pseudotyping vector.

The Env proteins of a lentivirus may be replaced with Env proteins from other retroviruses, nonretroviral viruses, or with chimeras of these proteins with other peptides or proteins, such as a vesicular stomatitis virus (VSV) G protein, a variant GP64 envelope protein, an Ebola virus envelope protein, a Marburg virus envelope protein, a Ross River Virus envelope protein, an influenza hemagglutinin envelope protein, a severe acute respiratory syndrome (SARS) S envelope protein, a Middle East Respiratory Syndrome (MERS) S envelope protein, or a Baboon endogenous envelope protein. These envelope proteins may increase the range of cells which can be transduced with lentiviral derived vectors.

A chimera may be constructed of an Env protein and of a ligand that binds to a specific cell surface receptor in order to target the vector to cells expressing that receptor. Exemplary chimeras may include FLA16 (a 6 amino acid peptide that binds integrin receptors), erythropoietin (which binds the erythropoietin receptor), and human heregulin (which binds the EGF and related receptors). Alternatively, the chimera may include an antibody variable light or heavy domain, or both domains joined by a suitable peptide linker (a so-called single chain antibody). Such an antibody domain could target any desired cell surface molecule, such as a tumor antigen, the human low-density lipoprotein receptor, or a determinant on human MHC Class I molecules.

Virions may be chemically, enzymatically, or physically modified after production in order to alter their cell specificity. Examples of modifications include chemical or enzymatic addition of a ligand that would be recognized by a cell surface receptor (e.g., addition of lactose so that the virions will transduce human hepatoma cells which express asialoglycoprotein receptors), or incubation of the virus with a biotinylated antibody directed against the vector's Env protein, followed by addition of a streptavidin-linked ligand recognized by the cell-surface receptor. A heterobispecific antibody also can be used to link the virion's Env protein to such a ligand.

Lentiviral Transfer Vectors

The present disclosure provides lentiviral transfer vectors useful for delivery of one or more transgenes (e.g., a CFTR gene, e.g., a human CFTR gene, e.g., a codon-optimized human CFTR gene) to a cell (e.g., a lung epithelial cell), tissue, or organ (e.g., a lung), e.g., of a patient suffering from a disorder (e.g., cystic fibrosis).

For example, provided herein is a lentiviral vector having a promoter operably linked to a codon optimized human CFTR gene.

In some embodiments, the lentiviral vector includes a promoter operably linked to a polynucleotide having at least 95%, 96%, 97%, 98%, or 99% sequence identity to the sequence of SEQ ID NO: 1. In some embodiments, the lentiviral vector includes a promoter operably linked to a polynucleotide having a sequence of SEQ ID NO: 1.

In some embodiments, the lentiviral vector includes a promoter operably linked to a polynucleotide having at least 95%, 96%, 97%, 98%, or 99% sequence identity to the sequence of SEQ ID NO: 2. In some embodiments, the lentiviral vector includes a promoter operably linked to a polynucleotide having a sequence of SEQ ID NO: 2.

In some embodiments, the lentiviral vector includes a promoter operably linked to a polynucleotide having at least 95%, 96%, 97%, 98%, or 99% sequence identity to the sequence of SEQ ID NO: 3. In some embodiments, the lentiviral vector includes a promoter operably linked to a polynucleotide having a sequence of SEQ ID NO: 3.

In another embodiment, provided herein is a lentiviral transfer vector comprising a promoter (e.g., an EF1α promoter or a PGK promoter) operably linked to a codon-optimized human CFTR gene, wherein expression of the codon-optimized human CFTR gene in cystic fibrosis human airway epithelial cells results in an increase in transepithelial Cl— transport compared to wildtype human CFTR. In some embodiments, the lentiviral transfer vector includes a PGK promoter operably linked to a human CFTR gene. The PGK promoter may have at least 95% (e.g., at least 96%, at least 97%, at least 98%, at least 99%) sequence identity to the nucleotide sequence of SEQ ID NO:4. In some embodiments, the lentiviral transfer vector includes a PGK promoter having a nucleotide sequence of SEQ ID NO:4 that is operably linked to a human CFTR gene. In some embodiments, the lentiviral transfer vector includes an EF1α promoter operably linked to a human CFTR gene. The EF1α promoter may have at least 95% (e.g., at least 96%, at least 97%, at least 98%, at least 99%) sequence identity to the nucleotide sequence of SEQ ID NO:5. In some embodiments, the lentiviral transfer vector includes an EF1α promoter having a nucleotide sequence of SEQ ID NO:5 that is operably linked to a human CFTR gene.

The lentiviral components of the lentiviral vector may originate from any suitable lentivirus, e.g., HIV-1, FIV, or other lentiviruses. For example, in some embodiments, the lentiviral components of the lentiviral vector originate from HIV-1.

In some embodiments, the lentiviral vector further includes one or more of a 5' LTR, a 3' LTR, a packaging signal, a Rev response element (RRE), a central polypurine tract (cPPT) sequence, and/or a central terminal (CTS). Any suitable 5' LTR may be used. The 5' LTR may be a wild-type 5' LTR or a non-naturally occurring 5' LTR, e.g., a chimeric 5' LTR. The 5' LTR may include an R and a U5 region. The 5' LTR may lack a U3 region. The 5' LTR may be a chimeric 5' LTR in which the U3 region may be replaced with a promoter (e.g., a viral promoter). The 5' LTR may include any suitable viral promoter.

Any suitable 3' LTR may be used. The 5' LTR may be a wild-type 3' LTR or a non-naturally occurring 3' LTR, e.g., a self-inactivating 3' LTR. The 3' LTR may be a self-inactivating 3' LTR. In some embodiments, the self-inactivating LTR includes an insertion of an insulator. Any suitable insulator(s) may be used, e.g., ankyrin. In some embodiments, the 3' LTR comprises an insertion of a human ankyrin 1 element, e.g., in the reverse orientation. In some embodiments, the 3' LTR comprises a polynucleotide sequence having at least 95%, 96%, 97%, 98%, or 99% sequence identity to the nucleotide sequence of SEQ ID NO:13. In some embodiments, the 3' LTR comprises the polynucleotide sequence of SEQ ID NO:13.

Also provided herein is a virion that includes any of the lentiviral vectors described herein.

The virion may include any suitable envelope protein. In some embodiments, the virion is pseudotyped. For example, the virion may be pseudotyped with a wild-type GP64 envelope protein, a variant GP64 envelope protein, an influenza hemagglutinin envelope protein, an Ebola envelope protein, a Marburg virus envelope protein, a Ross River Virus envelope protein, a severe acute respiratory syndrome (SARS) S envelope protein, a Middle East Respiratory Syndrome (MERS) S envelope protein, or a Baboon endogenous retrovirus envelope protein.

Regulatory Elements

Regulatory elements may be used to control the expression of the nucleic acids, e.g., transgene(s) of the lentiviral transfer vector, the marker(s) and viral genes or replacements of the packaging and transfer vectors, and the glycoprotein genes of the envelope vector. Regulatory elements refer to genetic elements that control some aspect of the expression of a nucleic acid sequence and include, without limitation, promoters, enhancers, splicing signals, polyadenylation signals, termination signals, insulators, and the like.

Promoters and Enhancers

Exemplary transcriptional control signals in eukaryotes include promoter and enhancer elements. Promoter and enhancer elements have been isolated from a variety of prokaryotic and eukaryotic sources including yeast, insect, and mammalian cells, and also from viruses. The selection of a particular promoter and enhancer depends on what cell type is to be used to express the protein of interest. Some eukaryotic promoters and enhancers have a broad host range while others are functional in only a subset of cell types (for a review, see, e.g., Voss et al., Trends Biochem. Sci., 11:287 (1986) and Maniatis et al., supra (1987)). For example, the SV40 early gene enhancer is very active in a wide variety of cell types from many mammalian species and has been widely used for the expression of proteins in mammalian cells (Dijkema et al., EMBO J. 4:761 (1985)). Two other examples of promoter/enhancer elements active in a broad range of mammalian cell types are those from the human elongation factor 1α (EF1α) gene. (Uetsuki et al., J. Biol. Chem., 264:5791 (1989); Kim et al., Gene 91:217 (1990); and Mizushima et al., Nuc. Acids. Res., 18:5322 (1990)) and the long terminal repeats of the Rous sarcoma virus (RSV) (Gorman et al., Proc. Natl. Acad. Sci. USA79: 6777 (1982)) and the human cytomegalovirus (CMV) (Boshart et al., Cell 41:521 (1985)).

In some embodiments, the lentiviral vector may include a promoter, e.g., to facilitate the initiation of transcription of an operably linked coding region. Any suitable promoter(s) may be used. The promoter(s) used may be constitutive, regulatable, inducible, or repressible. A constitutive promoter is one that is always active at essentially a constant level. Examples of constitutive promoters include the CAG promoter, the cytomegalovirus (CMV) promoter, the smCBA promoter, the EF1α promoter, and the SV40 promoter. A regulatable promoter is one whose level of activity is subject to regulation by a regulatory molecule. An inducible promoter is one that is normally substantially inactive but is activated by the binding of an inducer to an operator site of the promoter. A repressible promoter is one that is normally active but is substantially inactivated by the binding of a repressor to an operator site of the promoter.

A viral promoter (e.g., an RSV promoter or a CMV promoter) may be operably linked to the R and U5 regions of a truncated 5' long terminal repeat (LTR), resulting in a chimeric or hybrid 5' LTR.

A promoter, such as a human PGK-1 promoter, may also be operably linked to a transgene to regulate expression of the transgene. In some embodiments, the lentiviral vector includes a human PGK-1 promoter operably linked to a transgene (e.g., a CFTR gene, e.g., a codon optimized CFTR). In some embodiments of the disclosure, a lentiviral vector may include a human PGK-1 promoter comprising a nucleotide sequence having at least 90% (at least 91%, at least 92%, at least 93%, at least 94%, at least 95%, at least 96%, at least 97%, at least 98%, or at least 99%) sequence identity to the nucleotide sequence of SEQ ID NO:4. In some embodiments, the lentiviral vector includes a human PGK-1 promoter comprising the nucleotide sequence of SEQ ID NO:4.

A promoter, such as a human EF1α promoter, may also be operably linked to a transgene to regulate expression of the transgene. In some embodiments, the lentiviral vector includes a human EF1α promoter operably linked to a transgene (e.g., a CFTR gene, e.g., a codon optimized CFTR). In some embodiments of the disclosure, a lentiviral vector may include a human EF1α promoter comprising a nucleotide sequence having at least 90% (at least 91%, at least 92%, at least 93%, at least 94%, at least 95%, at least 96%, at least 97%, at least 98%, or at least 99%) sequence identity to the nucleotide sequence of SEQ ID NO:4. In some embodiments, the lentiviral vector includes a human EF1α promoter comprising the nucleotide sequence of SEQ ID NO:5.

A promoter/enhancer is a segment of DNA that contains sequences capable of providing both promoter and enhancer functions (i.e., the functions provided by a promoter element and an enhancer element). For example, the LTRs of retroviruses can contain both promoter and enhancer functions. The promoter/enhancer may be endogenous, exogenous, or heterologous. An endogenous promoter/enhancer is one that is naturally linked with a given gene in an existing, wild-type genome. An exogenous or heterologous promoter/enhancer is one that is linked to a gene by means of genetic manipulation (e.g., molecular biological techniques, including cloning and gene synthesis) such that transcription of that gene is directed by the linked promoter/enhancer.

The activity of a promoter and/or enhancer can be measured by detecting directly or indirectly, the level of transcription arising from the element(s). A strong promoter with high activity or a weak promoter with low activity may be used to drive transgene expression. Direct detection may involve quantitating the level of the RNA transcripts produced from that promoter and/or enhancer. Indirect detection may involve quantitation of the level of a protein produced from RNA transcribed from the promoter and/or enhancer. A commonly employed assay for promoter or enhancer activity utilizes a reporter gene (e.g., the chloramphenicol acetyltransferase (CAT) gene, luciferase, green fluorescent protein (GFP), or other reporter proteins known in the art). A promoter and/or enhancer is inserted upstream from the coding region for the reporter gene (e.g., a CAT gene), which may be located on a plasmid; which may be introduced into a cell line. The levels of the reporter gene are measured. For embodiments utilizing a CAT reporter gene, the level of enzymatic activity is proportional to the amount of CAT RNA transcribed by the cell line. Such reporter assays therefore allow a comparison to be made of the relative strength of different promoters or enhancers in a given cell line Promoters and enhancers may be naturally occurring sequences, or functional mutants thereof, including chimeras of natural sequences and mutants thereof. For example, a tissue-specific, development-specific, or otherwise regulatable element of one promoter may be introduced into another promoter.

Enhancer elements can be used to increase expression of modified DNA molecules or increase the lentiviral integration efficiency. In some embodiments, a lentiviral vector used in the methods and compositions described herein may include a nef sequence. In some embodiments, a lentiviral vector used in the methods and compositions described herein may include a central polypurine tract (cPPT) and central termination sequence (CTS) which enhance vector integration. The cPPT acts as a second origin of the (+)-strand DNA synthesis and introduces a partial strand overlap in the middle of the native HIV genome, while the CTS marks the termination of strand synthesis. The introduction of the cPPT sequence into a transfer vector backbone may increase the nuclear transport and the total amount of the genome integrated into the DNA of target cells. A lentiviral vector used in the methods and compositions described herein may include a Rev response element (RRE), which promotes the export of any unspliced, viral genomic RNA from the nucleus and may result in increased titers.

Any of the vectors described herein may include an element that permits expression of multiple polypeptides from a single nucleic acid molecule. For example, any of the vectors disclosed herein may include an internal ribosome entry site (IRES) sequence that permits the expression of multiple polypeptides from a single promoter. In addition to IRES sequences, other elements which permit expression of multiple polypeptides are known in the art. Any of the vectors disclosed herein may include multiple promoters that permit expression of more than one polypeptide. The vector used in the methods and compositions described herein may include a protein cleavage site that allows expression of more than one polypeptide. Examples of protein cleavage sites that allow expression of more than one polypeptide are described in Klump et al., Gene Ther.; 8:811 (2001), Osborn et al., Molecular Therapy 12:569 (2005), Szymczak and Vignali, Expert Opin Biol Ther. 5:627 (2005), and Szymczak et al., Nat Biotechnol. 22:589 (2004). It will be readily apparent to one skilled in the art that other elements that permit expression of multiple polypeptides identified in the future are useful and may be utilized in the vectors suitable for use with the compositions and methods described herein.

The vector used in the methods and compositions described herein may be a clinical grade vector or a current good manufacturing practice (CGMP) vector.

Post-Transcriptional Regulatory Elements

A lentiviral transfer vector of the disclosure may include a post-transcriptional regulatory element (PRE). PREs are nucleic acid sequences that contribute to regulation of expression of a DNA sequence within which the PRE is located. For example, a PRE may be transcribed along with the rest of the DNA sequence. The portion of the resulting mRNA molecule transcribed from the PRE may form a tertiary structure that enhances expression of the gene product. A PRE may include, in some instances, three components (alpha, beta, and gamma). The activity of the PRE may depend on how many of the components are present. For example, a full tripartite PRE may be more active than the alpha component alone. PREs suitable for inclusion in the lentiviral transfer vectors of the disclosure include, for example, woodchuck hepatitis B virus PRE (WPRE) and/or human hepatitis B virus PRE (HPRE).

Polyadenylation Signals

A lentiviral transfer vector of the disclosure may include a polyadenylation signal. Efficient expression of recombinant DNA sequences in eukaryotic cells may be improved by signals that direct efficient termination and polyadenylation of the resulting transcript. Transcription termination signals are generally found downstream of a polyadenylation signal and are a few hundred nucleotides in length. A polyadenylation (also referred to as "polyA") signal or a polyA sequence denotes a DNA sequence that directs both the termination and polyadenylation of the nascent RNA transcript. Efficient polyadenylation of the recombinant transcript may be desirable as transcripts lacking a polyA tail are generally unstable and rapidly degraded. Any suitable polyA signal may be utilized in the vectors disclosed herein. The polyA signal utilized in a vector may be heterologous or endogenous. An endogenous polyA signal is one that is found naturally at the 3' end of the coding region of a given gene in the genome. A heterologous polyA signal is one that is isolated from one gene and placed at the 3' end of another gene. Commonly used polyA signals for mammalian gene expression include SV40 polyA, human growth hormone (hGH) polyA, and rabbit beta-globin (rbGlob) polyA.

Insulators

Any of the lentiviral vectors disclosed herein may include one or more insulators. Insulators are commonly used to protect transgenes from silencing and/or positional effects, resulting in improved efficiency and increased stability of the transgene. In this way, insulators may act in the lentiviral system to protect the delivery of the transgene (e.g., CFTR, e.g., codon-optimized CFTR) while also increasing the efficiency of transcription of the transgene. In some embodiments, an insulator, such as a chicken hypersensitivity site 4 (HS4) insulator, a human hypersensitivity site 5 (HS5) insulator, or a fragment of any one of these insulators may be inserted in the lentiviral transfer vector to protect the delivery of the transgene (e.g. CTFR) and/or to increase the expression of the transgene in the target cells.

Host Cells for Lentivirus Production

A lentiviral transfer vector of the disclosure may be introduced into a host cell (packaging cell). The lentiviral transfer vector is generally co-transfected into the host cell together with one or more additional vectors (e.g., one or more packaging vectors). The one or more additional vectors may encode viral proteins and/or regulatory proteins. Co-transfection of the lentiviral transfer vector and the one or more additional vectors enables the host cell to produce a lentivirus (e.g., a lentivirus encoding a heterologous nucleic acid sequence from the lentiviral transfer vector). Lentiviruses produced by a host cell as described herein may be used to infect another cell. The heterologous nucleic acid and/or one or more additional elements (e.g., promoters and viral elements) may be integrated into the genome of the infected cell, thereby permitting the cell and its progeny to express gene(s) originating from the lentiviral transfer vector.

A packaging cell suitable for transfection with the lentiviral transfer vector (and one or more packaging vectors) may be a eukaryotic cell, such as a mammalian cell. The host cell may originate from a cell line (e.g., an immortalized cell line).

A target cell is the cell which is infected (transduced) with the lentiviral vector (lentivirus) encoding the transgene of interest. After transduction, the transgene of interest is stably inserted into the target cell genome and can be detected by molecular biology methods such as PCR and Southern blot. A transgene can be expressed in a target cell and detected by flow cytometry or Western blot. In some instances, a target cell is a human cell. In certain instances, the host cell is a particular cell type of interest, e.g., a primary T cell, SupT1 cell, Jurkat cell, or 293T cell.

It is contemplated that packaging may be inducible, as well as non-inducible. In inducible packaging cells and packaging cell lines, lentiviral particles are produced in response to at least one inducer. In non-inducible packaging cell lines and packaging cells, no inducer is needed in order for lentiviral particle production to occur.

Methods of Producing Lentiviruses

The lentiviral transfer vectors of the disclosure may be useful for producing lentiviruses in cells (e.g., a host cell as described herein). A method of producing a lentivirus using a lentiviral transfer vector described herein will generally involve introducing the lentiviral transfer vector and one or more additional vectors (e.g., a lentiviral packaging vector) into the cell. The vectors may be introduced into the cell using transfection methods well known in the art. After transfection, the cell may be permitted to express viral proteins encoded by the lentiviral transfer vector and/or the one or more additional vectors (e.g., by incubating the cell under standard conditions known in the art for inducing viral gene expression). In some instances, the viral genes are expressed under the control of a constitutive or inducible promoter. In the latter case, viral gene expression may be selectively induced by incubating the cell under conditions suitable for activating the inducible promoter. Viral proteins produced by the cell may subsequently form a viral particle, which bud from the cell surface and can be isolated from the solution (e.g., according to methods well known in the art). During formation of the virus, a polynucleotide including the sequence of the heterologous nucleic acid may be incorporated into the viral particle. Thus, this process yields a lentivirus that includes the heterologous nucleic acid sequence originating from the lentiviral transfer vector.

Pharmaceutical Compositions

Provided herein are pharmaceutical compositions that include any of the polynucleotides, lentiviral vectors, or virions described herein. The pharmaceutical compositions may include one or more pharmaceutically acceptable carriers. The polynucleotides, vectors, and virions described herein may be incorporated into a vehicle for administration into a patient, such as a human patient suffering from cystic fibrosis, as described herein. Pharmaceutical compositions containing polynucleotides that encode a polypeptide described herein can be prepared using any methods known in the art. Pharmaceutical compositions containing vectors, such as lentiviral vectors, that contain a nucleic acid sequence encoding a polypeptide described herein can be prepared using methods known in the art. For example, such compositions can be prepared using physiologically acceptable carriers, excipients, or stabilizers (Remington's Pharmaceutical Sciences 16th edition, Osol, A. Ed. (1980); incorporated herein by reference), and in the form of lyophilized formulations or aqueous solutions.

Mixtures of the polynucleotides or vectors (e.g., lentiviral vectors) described herein may be prepared in water suitably mixed with one or more excipients, carriers, or diluents. Dispersions may also be prepared in glycerol, liquid polyethylene glycols, and mixtures thereof and in oils. In some embodiments, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (e.g., U.S. Pat. No. 5,466,468). In any case, the formulation may be sterile and may be fluid. Formulations may be stable under the conditions of manufacture and storage and may be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), methylcellulose, suitable mixtures thereof, and/or vegetable oils. Proper fluidity may be maintained, for example, by the use of a coating, such as lecithin; by the maintenance of particle size in the case of dispersion; and by the use of surfactants (e.g., a poloxamer such as PLURONIC®). The prevention of the action of microorganisms can be brought about by various antibacterial and antifungal agents, for example, parabens, chlorobutanol, phenol, sorbic acid, thimerosal, and the like. In many cases, it may include isotonic agents, for example, sugars or sodium chloride. Prolonged absorption of the injectable compositions can be brought about by the use in the compositions of agents delaying absorption, for example, aluminum monostearate and gelatin. In some embodiments, the composition includes methylcellulose. In some embodiments, the composition includes a surfactant (e.g., a poloxamer such as PLURONIC®).

For example, a solution containing a pharmaceutical composition described herein may be suitably buffered, if necessary, and the liquid diluent first rendered isotonic with sufficient saline or glucose. These particular aqueous solutions are especially suitable for intravenous, intramuscular, subcutaneous, and intraperitoneal administration. In these solutions, sterile aqueous media that can be employed will be known to those of skill in the art in light of the present disclosure. For example, one dosage may be dissolved in 1 mL of isotonic NaCl solution and either added to 1000 ml of hypodermoclysis fluid or injected at the proposed site of infusion. Some variation in dosage may occur depending on the condition of the subject being treated. The person responsible for administration will, in any event, determine the appropriate dose for the individual subject. Moreover, for human administration, preparations may meet sterility, pyrogenicity, general safety, and purity standards as required by FDA Office of Biologics standards.

The pharmaceutical compositions described herein may include any of the polynucleotides, lentiviral vectors, or virions described herein in combination with one or more additional therapeutic agents. Exemplary additional therapeutic agents include, without limitation, an antibiotic (e.g., azithromycin (ZITHROMAX®), amoxicillin and clavulanic acid (AUGMENTIN®), cloxacillin and dicloxacillin, ticarcillin and clavulanic acid (TIMENTIN®), cephalexin, cefdinir, cefprozil, cefaclor; sulfamethoxazole and trimethoprim (BACTRIM®), erythromycin/sulfisoxazole, erythromycin, clarithromycin, tetracycline, doxycycline, minocycline, tigecycline, vancomycin, imipenem, meripenem, Colistimethate/COLISTIN®, linezolid, ciprofloxacin, levofloxacin, or a combination thereof), a mucus thinner (e.g., hypertonic saline or dornase alfa (PULMOZYME®)), a CFTR modulator (e.g., ivacaftor (KALYDECO®), lumacaftor, lumacaftor/ivacaftor (ORKAMBI®), tezacaftor/ivacaftor (SYMDEKO®), or TRIKAFTA® (elexacaftor/ivacaftor/tezacaftor)), a mucolytic (e.g., acetylcysteine, ambroxol, bromhexine, carbocisteine, erdosteine, mecysteine, and dornase alfa), normal saline, hypertonic saline, or a combination thereof.

Typically, the viral vectors are in a pharmaceutically suitable pyrogen-free buffer such as Ringer's balanced salt solution (pH 7.4). Although not required, pharmaceutical compositions may optionally be supplied in unit dosage form suitable for administration of a precise amount. Pharmaceutical compositions are generally sterile.

Cystic Fibrosis

Cystic fibrosis is an autosomally recessive disease that leads to persistent lung infections and an increasingly limited ability to breathe as the disease progresses over time. Cystic fibrosis is caused by a mutation in the CFTR gene leading to a dysfunctional CFTR protein. Over 2,500 mutations in the CFTR protein leading to cystic fibrosis have been identified. These mutations have been divided into five classes based upon the problematic effect they cause, including Class I, protein production mutations; Class II, protein processing mutations; Class III, gating mutations; Class IV, conduction mutations; and Class V, insufficient protein mutations. However, 70% of patients with CF have the Class II, F508 deletion which affects one of the two nucleotide binding domains in the CFTR protein. Additionally, the G551D mutation is a Class III mutation that affects about 3% of CF patients and prevents ATP binding in one of the two ATP binding pockets of the CFTR protein, abolishing ATP dependent gating. The well-understood genetic basis for the disease and resulting dysfunctional CFTR makes CF an ideal candidate for gene therapy. The CFTR mutations associated with CF typically lead to a basic chloride flux defect in the respiratory ciliated epithelial cells, as the dysfunctional CFTR cannot transport chloride to the cell surface, leading to an insufficient amount of water at the cell surface, and thus causing a thick, sticky mucus at the cell surface. As a result, the CFTR dysfunction causes chronic infection and inflammation of the respiratory tract and leads to high morbidity and mortality in CF patients.

CFTR cDNA gene transfer by adenoviral vectors or liposomes has demonstrated partial correction of the defective CFTR channel activity in the nasal epithelium of CF patients. Recent studies suggest that gene therapy may offer great benefits to CF patients even if only partial correction of CFTR gene function is achieved. The target cells of CF patients may be undifferentiated, proliferating and differentiated, non-proliferating lung epithelial cells. For example, both the dividing and non-dividing lung epithelial cell types can be targeted by pseudotyped retroviral vectors carrying a wild-type CFTR cDNA.

Methods of Treating Cystic Fibrosis

The disclosure provides methods of treating and/or preventing CF. In one aspect, provided herein is a method of treating CF, the method including administering to a subject in need thereof a therapeutically effective amount of any of the polynucleotides, lentiviral vectors, virions, and compositions (e.g., pharmaceutical compositions) described herein. The recombinant lentiviral vector may include any of the polynucleotides described herein. The lentiviral vector may be part of a pharmaceutical composition, including a pharmaceutically acceptable carrier and any of the lentiviral vectors or virions described herein. The polynucleotide may be part of a pharmaceutical composition, including a pharmaceutically acceptable carrier and any of the polynucleotides described herein.

Compositions described herein (e.g., polynucleotides, lentiviral vectors, virions, or compositions (e.g., pharmaceutical compositions) thereof) may be used in vivo as well as ex vivo. In vivo gene therapy comprises administering the vectors of this disclosure directly to a subject. Pharmaceutical compositions can be supplied as liquid solutions or suspensions, as emulsions, or as solid forms suitable for dissolution or suspension in liquid prior to use.

A composition described herein (e.g., polynucleotides, lentiviral vectors, virions, or pharmaceutical compositions) can be administered by any suitable route, e.g., by inhalation, nebulization, aerosolization, intranasally, intratracheally, intrabronchially, orally, parenterally (e.g., intravenously, subcutaneously, or intramuscularly), orally, nasally, rectally, topically, or buccally. They can also be administered locally or systemically. For administration into the respiratory tract, one mode of administration is by aerosol, using a composition that provides either a solid or liquid aerosol when used with an appropriate aerosolubilizer device. Another mode of administration into the respiratory tract is using a flexible fiberoptic bronchoscope to instill the vectors. In some embodiments, a composition is administered in aerosolized particles intratracheally and/or intrabronchially using an atomizer sprayer (e.g., with a MADgic® laryngo-tracheal mucosal atomization device). In other embodiments, a composition is administered in aerosolized particles intratracheally and/or intrabronchially using a nebulizer. In some embodiments, the composition is administered parentally. In other embodiments, the composition is administered systemically. Vectors can also be introduced by way of bioprostheses, including, by way of illustration, vascular grafts (PTFE and dacron), heart valves, intravascular stents, intravascular paving as well as other non-vascular prostheses. General techniques regarding delivery, frequency, composition, and dosage ranges of vector solutions are within the skill of the art.

For administration to the upper (nasal) or lower respiratory tract by inhalation, the compositions described herein (e.g., polynucleotides, lentiviral vectors, virions, or pharmaceutical compositions) are conveniently delivered from an insufflator, nebulizer, or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Alternatively, for administration by inhalation or insufflation, the composition may take the form of a dry powder, for example, a powder mix of the agent and a suitable powder base such as lactose or starch. The powder composition may be presented in unit dosage form in, for example, capsules or cartridges, or gelatine or blister packs from which the powder may be administered with the aid of an inhalator, Insufflator, or a metered-dose inhaler. For intranasal administration, the agent may be administered via nose drops, a liquid spray, such as via a plastic bottle atomizer, or metered-dose inhaler. Typical of atomizers are the Mistometer (Wintrop) and the Medihaler (Riker).

Administration of the compositions described herein (e.g., lentiviral vectors, virions, or pharmaceutical compositions) may be continuous or intermittent, depending, for example, upon the recipient's physiological condition, whether the purpose of the administration is therapeutic or prophylactic, and other factors known to skilled practitioners. The compositions described herein can be administered once, or multiple times (e.g., 2, 3, 4, 5, 6, 7, 8, 9, 10, 20, or more times), at the same or at different sites. The administration of the agents of the disclosure may be essentially continuous over a preselected period of time or may be in a series of spaced doses.

The compositions described herein (e.g., polynucleotides, lentiviral vectors, virions, or pharmaceutical compositions) may be administered as a monotherapy. The compositions described herein (e.g., lentiviral vectors, virions, or pharmaceutical compositions) can also be administered in combination with one or more additional therapeutic agents. Any suitable additional therapeutic agent(s) may be used including standard of care therapies for CF. Additional therapeutic agents may include but are not limited to an antibiotic, a mucus thinner, a CFTR modulator, a mucolytic, normal saline, hypertonic saline, or a combination thereof. In some embodiments, the one or more additional therapeutic agents includes an antibiotic, such as azithromycin (ZITHROMAX®), amoxicillin and clavulanic acid (AUGMENTIN®), cloxacillin and dicloxacillin, ticarcillin and clavulanic acid (TIMENTIN®), cephalexin, cefdinir, cefprozil, cefaclor; sulfamethoxazole and trimethoprim (BACTRIM®), erythromycin/sulfisoxazole, erythromycin, clarithromycin, tetracycline, doxycycline, minocycline, tigecycline, vancomycin, imipenem, meripenem, Colistimethate/COLISTIN®, linezolid, ciprofloxacin, levofloxacin, or a combination thereof. In some embodiments, the additional therapeutic agent includes a mucus thinner, such as hypertonic saline or dornase alfa (PULMOZYME®). In some embodiments, the additional therapeutic agent includes a CFTR modulator, such as ivacaftor (KALYDECOR), lumacaftor, lumacaftor/ivacaftor (ORKAMBI®), TRIKAFTA® (elexacaftor/ivacaftor/tezacaftor), and tezacaftor/ivacaftor (SYMDEKO®). In some embodiments, the additional therapeutic agent includes a mucolytio, such as acetylcysteine, ambroxol, bromhexine, carbocisteine, erdosteine, mecysteine, and dornase alfa. In other embodiments, the additional therapeutic agents are normal saline, hypertonic saline, or a combination thereof.

The compositions described herein (e.g., polynucleotides, lentiviral vectors, virions, or pharmaceutical compositions) may be administered to a mammal alone or in combination with pharmaceutically acceptable carriers. As noted above, the relative proportions of active ingredient and carrier are determined by the solubility and chemical nature of the compound, chosen route of administration, and standard pharmaceutical practice.

The dosage of the present compositions will vary with the form of administration, the particular compound chosen, and the physiological characteristics of the particular patient under treatment. It is desirable that the lowest effective concentration of virus be utilized in order to reduce the risk of undesirable effects, such as toxicity.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Codon-Optimization of CFTR Gene

In order to advance lentiviral gene therapy and achieve full correction of CF phenotypes in the airways, we investigated the effects of CFTR codon optimization on transgene expression and function. Since airway epithelial cells are interconnected through gap junctions, we hypothesized that, without wishing to be bound by any one particular theory, a small number of cells expressing high levels of CFTR could perform sufficient anion transport to rescue CF phenotypes.

Materials and Methods

Plasmids

WT CFTR and coCFTR1 (GenBank MW222115) in the pcDNA3.1 (+) vector were used. Only the first 356 amino acids of coCFTR1 were codon optimized. coCFTR1 contains a valine for methionine substitution at position 1475 which does not affect protein function (see, Smit et al. (1993). *Proc Natl Acad Sci USA* 90:9963-9967). Codon optimization and synthesis of coCFTR2 (GenBank MW116826) was commercially performed by Genscript in the Bluescript plasmid. coCFTR2 contains the leucine for phenylalanine substitution at position 833 present in the originally reported CFTR sequence, which increases protein solubility but does not affect protein structure (see, Baker et al. (2007). *Nat Struct Mol Biol* 14:738-745). Codon optimization of coCFTR3 (GenBank MW116827) was performed using JCat, and was commercially synthesized by Genscript in the HIV-PGK-coCFTR3 vector. coCFTR2 and coCFTR3 were sub-cloned into pcDNA3.1 (+). HIV-PGK-WTCFTR and HIV-EF1α-GFP were synthesized by Genscript and used to clone HIV-PGK-GFP, HIV-PGK-coCFTR3 and HIV-EF1α-WTCFTR. The HIV-based vectors used are second generation, self-inactivating (SIN), and contain a human ankyrin 1 element in the reverse orientation within the 3' LTR that improves long-term expression by avoiding silencing.

Codon Optimized Sequence Comparisons

CFTR domains were defined by the following amino acid positions: TMD1 (1-356), NBD1 (357-678), RD (679-840), TMD2 (841-1156), NBD2 (1157-1481). Nucleotide content was determined using SeqBuilder Pro 17 (DNASTAR). Codon usage and $GC_3$ content was determined using Sequence Manipulation Suite.

Fischer Rat Thyroid (FRT) Electroporation and Epithella Formation

Codon optimized or wildtype versions of CFTR cDNAs were electroporated into FRT cells and seeded on filters in triplicate. FRT cells were cultured in Ham F-12 Coon's modified medium supplemented with 5% FBS and 1% penicillin/streptomycin at 37° C. in 5% $CO_2$ humidified environment. $1.2\times10^6$ FRT cells were electroporated with 4 μg of pcDNA3.1 (+) plasmid (Amaxa NUCLEOFECTOR™ 2b, NUCLEOFECTOR™ Kit L, Lonza). The GFP plasmid included in the electroporation kit was used to verify successful electroporation and these cells were used as negative controls in Ussing chamber experiments. Cells were resuspended in a total volume of 700 μl and 200 μl were seeded in each of three, collagen-coated polycarbonate membrane tissue culture inserts (Corning TRANSWELL™, 6.5 mm, 0.4 μm pore) with 400 μl media on the basolateral compartment. The next day, apical media was removed, and the basolateral media was replaced. Seven days later transepithelial CI-transport and mRNA expression were measured.

HEK293 Cell Transfection

HEK293 cells were cultured in 5% FBS and 1% penicillin/streptomycin at 37° C. in 5% $CO_2$ humidified environment. $1\times10^5$ cells per well were seeded on a 6-well plate. The next day, 2 μg of pcDNA3.1 (+) plasmid was transfected following manufacturer instructions for Lipofectamine 2000 (Invitrogen). When confluent, cells were harvested for mRNA or western blot analysis. A GFP control plasmid was used to verify successful transfection and to serve as a negative control in mRNA and western blot analyses.

Transduction and Differentiation of Primary Human Airway Basal Cells

All primary human airway epithelial cells were obtained from the University of Iowa In Vitro Models and Cell Culture Core under approval from the University of Iowa Institutional Review Board. De-identified cells isolated from donated non-CF lungs, or discarded CF lungs after transplant were provided. $8\times10^5$ freshly isolated primary basal cells from CF donors were seeded on collagen coated 10 cm plates in BRONCHIALIFE™ Epithelial Basal Medium (Lifeline). Once cells reached ~80% confluency, cells were dissociated using TRYPLE™ (Gibco) and $1\times10^5$ cells were seeded on collagen-coated polycarbonate membrane tissue culture inserts (Corning TRANSWELL™, 6.5 mm, 0.4 μm pore) along with the viral vector and polybrene (2 μg/ml) in a final volume of 200 μl. 400 μl defined culture media (ULTROSER™ G) was maintained in the basolateral compartment throughout the differentiation process. Cells were maintained under submerged culture conditions for 48-72 hours. Apical media was then removed, and cultures were maintained at air-liquid interface conditions for a minimum of four weeks. Once differentiated, cells were either mounted directly in Ussing chambers for electrophysiology analysis or dissociated for flow cytometry analysis using ACCUMAX™ (Sigma).

For non-CF cells, $2\times10^5$ cells were seeded onto collagen-coated 6-well plates along with viral vector and POLYBRENE® (2 μg/ml) in BronchiaLife™ Epithelial Basal Medium (1 mL final volume). Media was replaced as needed until cells reached confluency 3-5 days post-transduction and were harvested using TypLE for flow cytometry analysis.

Western Blot Analysis

Adherent cells in a 6-well plate were washed with PBS and 0.5 ml RIPA buffer (Thermo Fisher Scientific/Gibco, Waltham, MA) with protease inhibitor (Roche COMPLETE™ ULTRA Tablets, Mini, EDTA-free, Basel, Switzerland) was added to each well. The plate was placed at −80° C. for 10 minutes, and then allowed to thaw at room temperature. Cell lysate was collected, and cell debris was separated by centrifugation. Protein-containing supernatant was collected, and stored at −20° C. A BCA assay (Pierce BCA Protein Assay Kit, Thermo Fisher Scientific/Gibco, Waltham, MA) was performed prior to each western blot to quantify protein. 20 μg of protein per sample were loaded in a 3-8% CRITERION XT™ Tris-Acetate Gel (Bio-Rad) and ran at 125 V for 90 minutes in Tris/Tricine/SDS Running Buffer (Bio-Rad). Transfer to IMMOBILON™-FL PVDF membrane (Millipore) was performed at 110 ρA, 4° C., overnight in high glycine transfer buffer (120 g glycine, 6 g Tris-base in 2 L water). The membrane was blocked with 0.1% Hammarsten casein in PBS for 1 hour. Primary antibodies (mouse-anti-human CFTR UNC-596, and rabbit-anti-human vinculin Thermo Fisher Scientific/Gibco, Waltham, MA) were diluted 1:2000 and incubated at room temperature for 2 hours. Secondary IRDYE™ antibodies (LI-COR donkey-anti-rabbit 680RD, and donkey-anti-mouse 800CW) were diluted 1:20,000 and incubated for 1 hour at room temperature. Three washes with TBST for 15 minutes were performed between each step. Membrane was imaged and analyzed using LI-COR ODYSSEY™ system.

mRNA Measurements

Adherent cells in a 6-well plate were washed with PBS. Cell contents of each well were collected in 0.5 ml TRIzol (Invitrogen). RNA was isolated following manufacturer instructions for DIRECT-ZOL™ RNA Kit (Zymo Research). cDNA was generated using High-Capacity-RNA-to-cDNA Kit (Applied Biosystems) and qPCR (Applied Biosystems 7900HT) was performed using Power SYBR™ Green PCR Master Mix (Thermo Fisher Scientific/Gibco, Waltham, MA) using primers directed against the polyadenylation sequence of pcDNA3.1 (+) plasmids 5'-CTCGACTGTGCCTTCTAGTTG-3' (SEQ ID NO:6) and 5'-GCACCTTCCAGGGTCAAG-3' (SEQ ID NO: 7). GAPDH was used to normalize gene expression using primers 5'-GGATTTGGTCGTATTGGG-3' (SEQ ID NO:8) and 5'-GGATTTGGTCGTATTGGG-3' (SEQ ID NO:9).

Patch Clamp Experiments

Experiments were performed as previously described (see, Dong et al. (2008). *Biophys J* 95:5178-5185). Excised, inside-out membrane patches from 293T human embryonic kidney cells transiently expressing WT CFTR or coCFTR3 using pcDNA3.1 (+) vectors were used. The pipette (extracellular) solution contained: 140 mM N-methyl-D-glucamine, 3 mM $MgCl_2$, 5 mM $CaCl_2$), 100 mM L-aspartic acid, and 10 mM tricine, pH 7.3 with HCl. The bath (intracellular) solution contained 140 mM N-methyl-D-glucamine, 3 mM $MgCl_2$, 1 mM Cs ethylene glycol bis(2-aminoethyl ether)-N,N,N',N' tetraacetic acid (CsEGTA), and 10 mM tricine, pH 7.3 with HCl. Following patch excision, CFTR channels were activated with 22 nM protein kinase A (PKA) catalytic subunit (from bovine heart, EMD Millipore Corporation, Billerica, MA) and 1 mM ATP (magnesium salt, Sigma-Aldrich, St. Louis, MO). PKA catalytic subunit was present in all cytosolic solutions that contained ATP. Experiments were performed at room temperature (23-26° C.). Recordings from patches containing 2-8 channels were digitized at 5 kHz and prior to analysis low-pass filtered at 500 Hz using an 8-pole Bessel filter (Model 900, Frequency Devices, Inc., Haverhill, MA). Single channel openings and closings were analyzed with a burst delimiter of 20 ms using Clampfit software (version 10.3, Molecular Devices, Sunnyvale, CA) (see, Carson et al. (1995). *J Biol Chem* 270:1711-1717). Events <4 ms duration were ignored. The mean interburst interval (IBI) was calculated using the formula $P_o=(BD \times P_{o,Burst})/(BD+IBI)$, where $P_o$ is the mean open state probability, BD is the mean burst duration and $P_{o,Burst}$ is the mean open state probability within a burst (see, Cotton et al. (1998). *J Biol Chem* 273:31873-31879).

Flow Cytometry

Cells were resuspended in 100 μl PBS containing 2% FBS with LIVE/DEAD™ Fixable Far Red Stain Kit (Invitrogen) and incubated for 30 minutes protected from light. Three washes with 1 ml 2% FBS in PBS were performed before resuspending cells in a final volume of 500 μl for flow cytometry analysis in ATTUNE™ NXT Flow Cytometer (Invitrogen). Doublets, and dead cells were excluded from analysis.

Short-Circuit Measurements

CFTR function was quantified in Ussing chambers by measuring the change in current ($\Delta I_T$ or $\Delta I_{sc}$) generated across an epithelial cell layer in response to cAMP agonists forskolin (F) and 3-isobutyl-1-methylxanthine (IBMX). CFTR channels were isolated by inhibiting sodium and anion exchangers using amiloride and 4,4'-Diisothiocyano-2,2'-stilbenedisulfonic acid (DIDS) respectively. Based on the results from our cell line model, we selected coCFTR3 to compare to WT CFTR in CF primary human airway epithelial cells. Basal progenitor cells were transduced with a lentiviral vector carrying WT CFTR, coCFTR3 or GFP and they were then allowed to differentiate for four weeks before measuring transepithelial $Cl^-$ current.

For transepithelial chloride current measurements epithelial cultures were mounted in Ussing chambers, submerged in a solution containing 135 mM NaCl, 5 mM HEPES, 0.6 mM $KH_2PO_4$, 2.4 mM $K_2HPO_4$, 2.2 mM $MgCl_2$, 1.2 mM $CaCl_2$, and 5 mM dextrose, and bubbled with air. For bicarbonate measurements cultures were submerged in a chloride-free solution composed of 118.9 mM Na gluconate, 25 mM $NaHCO_3$, 5 mM Ca gluconate, 1 mM Mg gluconate, 2.4 mM $K_2HPO_4$, 0.6 mM $KH_2PO_4$, 5 mM dextrose, and bubbled with $CO_2$. Amiloride, ENaC inhibitor, and DIDS, a $Cl^-$ exchanger inhibitor, were sequentially added apically to a final concentration of 100 μM. CFTR was then apically activated with the cyclic AMP agonists forskolin and 3-isobutyl-2-methylxanthine (IBMX) at a final concentration of 10 μM and 100 μM, respectively. Finally, the CFTR inhibitor GlyH-101 (Cystic Fibrosis Foundation) was added apically to a final concentration of 100 μM. Changes in short circuit current ($\Delta I_{sc}$) in response to CFTR activation and inhibition were calculated. For FRT transepithelial current measurements, a $Cl^-$ gradient was used. Prior to forskolin and IBMX stimulation, the apical solution was replaced with one in which NaCl was replaced with $NaC_5H_{11}O_7$, and changes in current were calculated (Alt).

Statistics

All data were analyzed using GraphPad Prism 8 software. Statistical significance was determined using one-way ANOVA with Dunn's multiple comparison test, one-way ANOVA on ranks (Kruskal-Wallis test) with Dunn's multiple comparisons test, or multiple t-tests with Bonferroni-Dunn correction as appropriate. Error bars represent mean±SE.

Results

CFTR is composed of two sets of transmembrane domains (TMD1 and TMD2), two nucleotide binding domains (NBD1 and NBD2), and a regulatory domain (RD) (FIG. 1A). Different approaches for codon optimization were used to generate codon optimized CFTR (coCFTR) genes coCFTR2 (SEQ ID NO: 1), coCFTR3 (SEQ ID NO: 2), and SEQ ID NO:3. These codon-optimized CFTR genes were compared to coCFTR1 (Kim et al., *Science,* 348:6233, 444-448). As shown in FIG. 1B, only transmembrane domain 1 (TMD1) of coCFTR1 was optimized. The remaining domains, including nucleotide binding domains 1 and 2 (NBD1/2), regulatory domain (RD) and transmembrane domain 2 (TMD2) retained the wildtype (WT) sequence. Except for coCFTR1, codon changes did not segregate by CFTR protein domain. The entire gene was optimized for coCFTR2 and coCFTR3 (FIG. 1B). A proprietary algorithm (Genscript) was used for coCFTR2 and a publicly available algorithm (JCat) (see, Grote et al. (2005). *Nucleic Acids Res* 33: W526-531.) for coCFTR3. FIG. 1C shows the percentage of nucleotides in WT CFTR, coCFTR1, coCFTR2 (SEQ ID NO: 1), and coCFTR3 (SEQ ID NO: 2) that are guanine (G), adenine (A), thymine (T), or cytosine (C). The total GC content increased in all codon optimized sequences compared to WT CFTR, but coCFTR3 had the highest increase (from 42% to 64%) (FIG. 1C). An increase in the GC content of SEQ ID NO: 2, compared to the other sequences was apparent, as shown in FIG. 1D, with coCFTR3 having a GC: content of nearly 100%. Codons using a G or C at the third nucleotide position ($GC_3$) were also increased in the single codon optimized domain of coCFTR1, and throughout all domains of coCFTR2 (SEQ ID NO: 1) and coCFTR3 (SEQ ID NO: 2). The divergence of coCFTR sequence from wildtype (WT) CFTR is summarized in Table 1, which shows that coCFTR sequences differ from WT CFTR in their codons by 16-68% and in their nucleotide sequence by 6-35%. The codon adaptive index (CAI) is higher in all coCFTR sequences compared to WT CFTR.

TABLE 1

Summary of codon optimization of CFTR

| Sequence | CAI | Codon Divergence | Sequence Divergence |
|---|---|---|---|
| WT CFTR | 0.74 | — | — |
| coCFTR 1 | 0.76 | 16% (355/1481) | 6% (276/4443) |
| coCFTR 2 (SEQ ID NO: 1) | 0.80 | 65% (961/1481) | 32% (1426/4443) |
| coCFTR 3 (SEQ ID NO: 2) | 0.99 | 68% (1001/1481) | 35% (1561/4443) |

As expected, all strategies increased the CAI compared to WT CFTR, but the amino acid sequence remained the same (Table 2).

TABLE 2

Codon Usage of CFTR Sequences

| | | | | WT CFTR | coCFTR1[a] | coCFTR2[b] | coCFTR[3] |
|---|---|---|---|---|---|---|---|
| Ala | G | C | G | 6 | 3 | 4 | 0 |
| | | | A | 34 | 26 | 20 | 0 |
| | | | T | 27 | 20 | 22 | 0 |
| | | | C | 16 | 34 | 37 | 83 |
| Arg | G | C | G | 16 | 13 | 17 | 0 |
| | | | A | 37 | 24 | 22 | 0 |
| | C | | G | 8 | 4 | 13 | 0 |
| | | | A | 9 | 33 | 7 | 0 |
| | | | T | 3 | 2 | 7 | 0 |
| | | | C | 5 | 2 | 12 | 78 |
| Asn | A | A | T | 25 | 21 | 24 | 0 |
| | | | C | 29 | 33 | 30 | 54 |
| Asp | G | A | T | 38 | 32 | 26 | 0 |
| | | | | 20 | 26 | 32 | 58 |
| Cys | T | G | T | 8 | 6 | 10 | 0 |
| | | | C | 10 | 12 | 8 | 18 |
| Gin | C | A | G | 31 | 37 | 47 | 67 |
| | | | A | 36 | 30 | 20 | 0 |
| Glu | G | A | G | 30 | 45 | 61 | 93 |
| | | | | 63 | 48 | 32 | 0 |
| Gly | G | G | G | 16 | 10 | 21 | 0 |
| | | | A | 38 | 30 | 18 | 0 |
| | | | T | 15 | 14 | 13 | 0 |
| | | | C | 15 | 30 | 32 | 84 |
| His | C | A | T | 11 | 9 | 7 | 0 |
| | | | | 14 | 16 | 18 | 25 |
| Ile | A | T | A | 33 | 26 | 14 | 0 |
| | | | T | 50 | 39 | 46 | 0 |
| | | | C | 36 | 54 | 59 | 119 |
| Leu[b] | T | T | G | 34 | 27 | 29 | 0 |
| | | | A | 37 | 29 | 13 | 0 |
| | C | T | G | 37 | 26 | 72 | 183 |
| | | | A | 19 | 12 | 9 | 0 |
| | | | T | 32 | 20 | 23 | 0 |
| | | | C | 24 | 69 | 38 | 0 |
| Lys | A | A | G | 35 | 47 | 53 | 92 |
| | | | A | 57 | 45 | 39 | 0 |
| Met[a] | A | T | G | 38 | 39 | 38 | 38 |
| Phe[b] | T | T | T | 47 | 35 | 37 | 0 |
| | | | C | 38 | 50 | 47 | 85 |
| | | | | | | ww | |
| Pro | C | C | G | 1 | 0 | 5 | 0 |
| | | | A | 13 | 21 | 12 | 0 |
| | | | T | 20 | 15 | 13 | 0 |
| | | | C | 11 | 9 | 15 | 45 |
| Ser | A | G | T | 19 | 15 | 18 | 0 |
| | | | C | 24 | 20 | 28 | 123 |
| | T | C | G | 4 | 3 | 9 | 0 |
| | | | A | 29 | 22 | 24 | 0 |
| | | | T | 30 | 23 | 26 | 0 |
| | | | C | 17 | 40 | 18 | 0 |
| Thr | A | C | G | 3 | 3 | 6 | 0 |
| | | | A | 33 | 31 | 18 | 0 |
| | | | T | 32 | 29 | 26 | 0 |
| | | | C | 15 | 20 | 33 | 83 |
| Trp | T | G | G | 23 | 23 | 23 | 23 |
| Tyr | T | A | G | 22 | 15 | 15 | 0 |
| | | | C | 18 | 25 | 25 | 40 |
| Val[a] | G | T | G | 36 | 46 | 48 | 89 |
| | | | A | 12 | 11 | 9 | 0 |
| | | | T | 23 | 17 | 12 | 0 |
| | | | C | 18 | 14 | 20 | 0 |

TABLE 2-continued

Codon Usage of CFTR Sequences

| | | | | WT CFTR | coCFTR1[a] | coCFTR2[b] | coCFTR[3] |
|---|---|---|---|---|---|---|---|
| Stop | T | G | A | 0 | 0 | 0 | 0 |
| | | A | G | 1 | 1 | 1 | 0 |
| | | | A | 0 | 0 | 0 | 1 |
| | | | Total | 1481 | 1481 | 1481 | 1481 |
| | | | CAI | 0.74 | 0.76 | 0.80 | 0.99 |

[a]cOCFTR1 substitutes methionine for valine at position 1475.
[b]coCFTR2 substitutes leucine for phenylalanine at position 833.

Figures 2A, 2B, 2C:
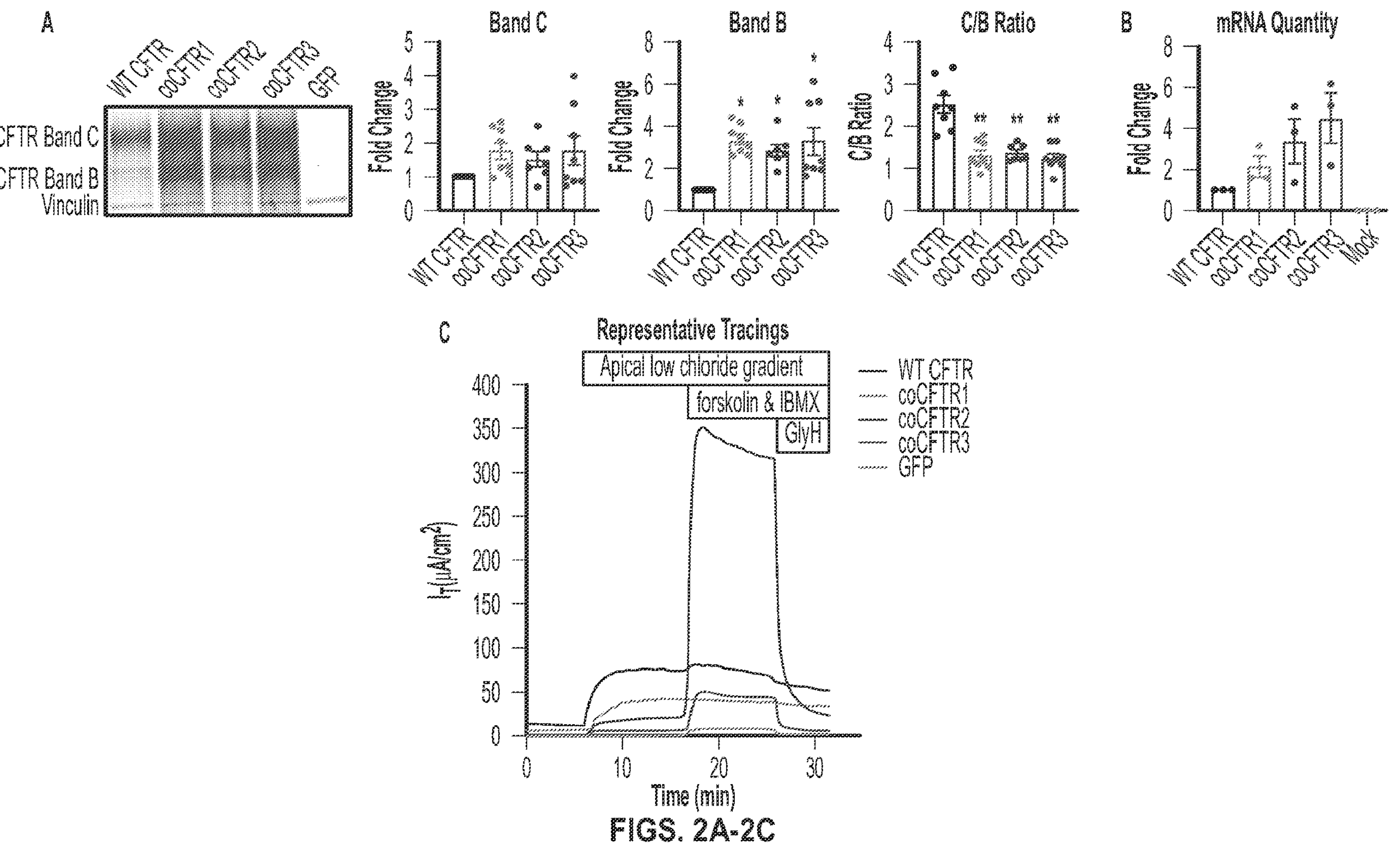
FIG. 2A shows the results of Western Blot analysis of different glycosylated forms, bands B and C, and vinculin, which was used as a loading control for HEK293 cells with pcDNA3.1 (+) plasmids expressing WT CFTR, coCFTR1, coCFTR2 (SEQ ID NO: 1), coCFTR3 (SEQ ID NO: 2), or a GFP control (left panel), and the densitometry analysis of band C, band B, and the C/B ratio for each CFTR (right panel). Densitometry analysis demonstrated no significant increase for CFTR band C, a significant increase in CFTR band B (*$p \leq 0.007$), and a significant decrease in C/B ratio (** $p \leq 0.02$) with coCFTR1, coCFTR2, and coCFTR3 compared to WT CFTR.
FIG. 2B is a graph showing the results of qRT-PCR analysis of CFTR mRNA performed using primers that target a portion of the polyadenylation sequence present in all plasmids.
FIG. 2C shows a representative tracing of the transepithelial current measured when sodium and non-CFTR anion channels were inhibited with sequential addition of amiloride and DIDS, respectively, prior to activation of CFTR channels with cAMP agonists forskolin and 3-isobutyl-1-methylxanthine (IBMX) in Fisher Rat Thyroid (FRT) cells that were transfected with pcDNA3.1 (+) plasmid expressing wildtype WTCFTR, coCFTR1, coCFTR2 (SEQ ID NO: 1), coCFTR3 (SEQ ID NO: 2), or a GFP control. The CFTR-specific current was verified with addition of CFTR inhibitor GlyH.

To test the therapeutic potential of CFTR codon optimization, three different CFTR cDNA sequences were compared in a model cell line. Each codon optimized CFTR (coCFTR) sequence was cloned into the pcDNA3.1 expression vector and electroporated into Fischer rat thyroid (FRT) cells. FRT cells do not express endogenous CFTR and can form a polarized epithelium. One week later the transepithelial CI-transport was measured and found that each codon optimized sequence provided a different degree of improved CFTR expression and function as evidenced by $Cl^-$ transepithelial transport. To confirm this was not a cell line specific effect, mRNA and protein production in transfected HEK293 cells was measured after 72 hours. A GFP expression plasmid served as a control. The protein concentration of WT CFTR, coCFTR1, coCFTR2 (encoded by SEQ ID NO: 1), and coCFTR3 (encoded by SEQ ID NO: 2), was measured by Western Blot as shown in FIG. 2A, with GFP as a control. Different glycosylation patterns, including bands B and C, were detected, and vinculin was used as a loading control. Densitometry analysis demonstrated no significant increase for CFTR band C, a significant increase in CFTR band B (*p≤0.007), and a decrease in C/B ratio (*p≤0.02) with coCFTR1, coCFTR2 (SEQ ID NO: 1), and coCFTR3 (SEQ ID NO: 2) compared to WT CFTR (FIG. 2A). CFTR mRNA was quantified by qRT-PCR using primers that target a portion of the polyadenylation sequence present in all plasmids. While all coCFTR sequences resulted in higher average mRNA content over WT CFTR, the fold increases were not statistically significant for any sequence as shown in FIG. 2B.

Figures 2D, 2E:
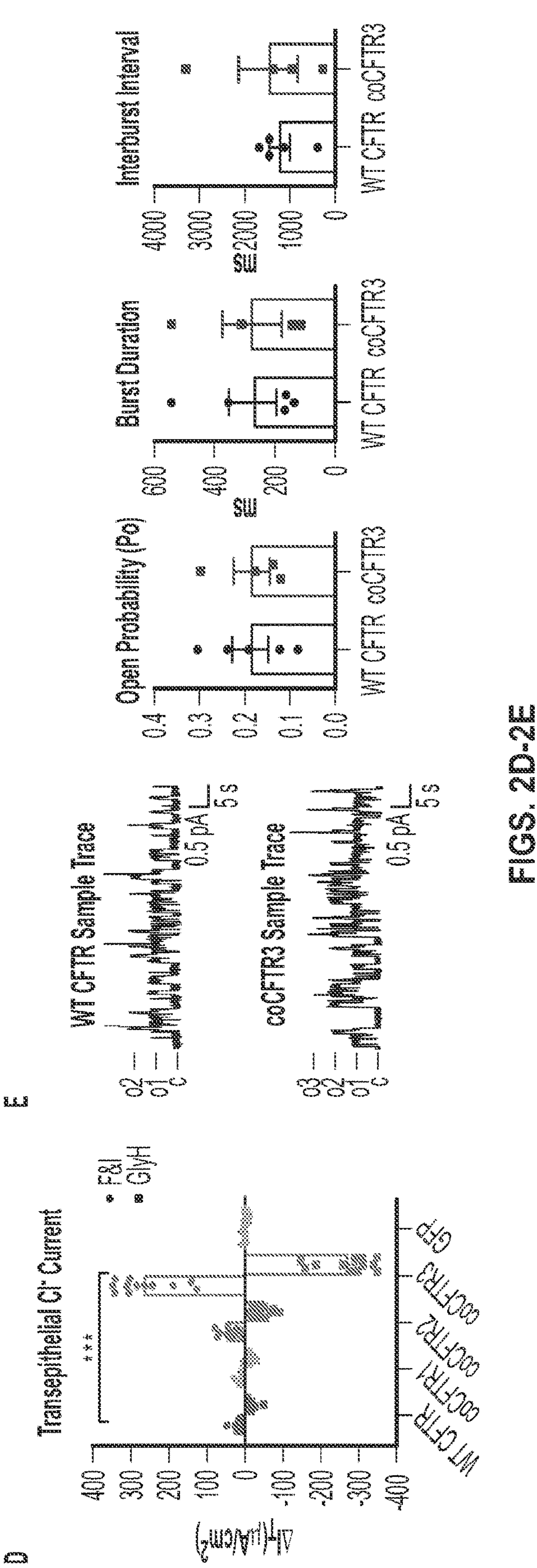
FIG. 2D is a graph showing the change in current ($\Delta I_T$) calculated for transepithelial CH transport in response to the cAMP agonists forskolin and IBMX (F&I) and GlyH for Fisher Rat Thyroid (FRT) cells transfected with a pcDNA3.1 (+) plasmid expressing WT CFTR, coCFTR1, coCFTR2 (SEQ ID NO: 1), coCFTR3 (SEQ ID NO: 2) or GFP in order to analyze protein function. The results were considered statistically significant if *** $p<0.0001$. Mean±SE is shown.
FIG. 2E shows representative tracings from patch clamp studies performed in HEK 293 cells transfected with WT CFTR or coCFTR3 (SEQ ID NO: 2), and the graphs of channel open probability, burst duration, and interburst intervals for coCFTR3 (SEQ ID NO: 2) where the PKA catalytic subunit (22 nM) and ATP (1 mM) were present throughout, and the holding voltage was −70 mV.
Figures 6A, 6B, 6C:
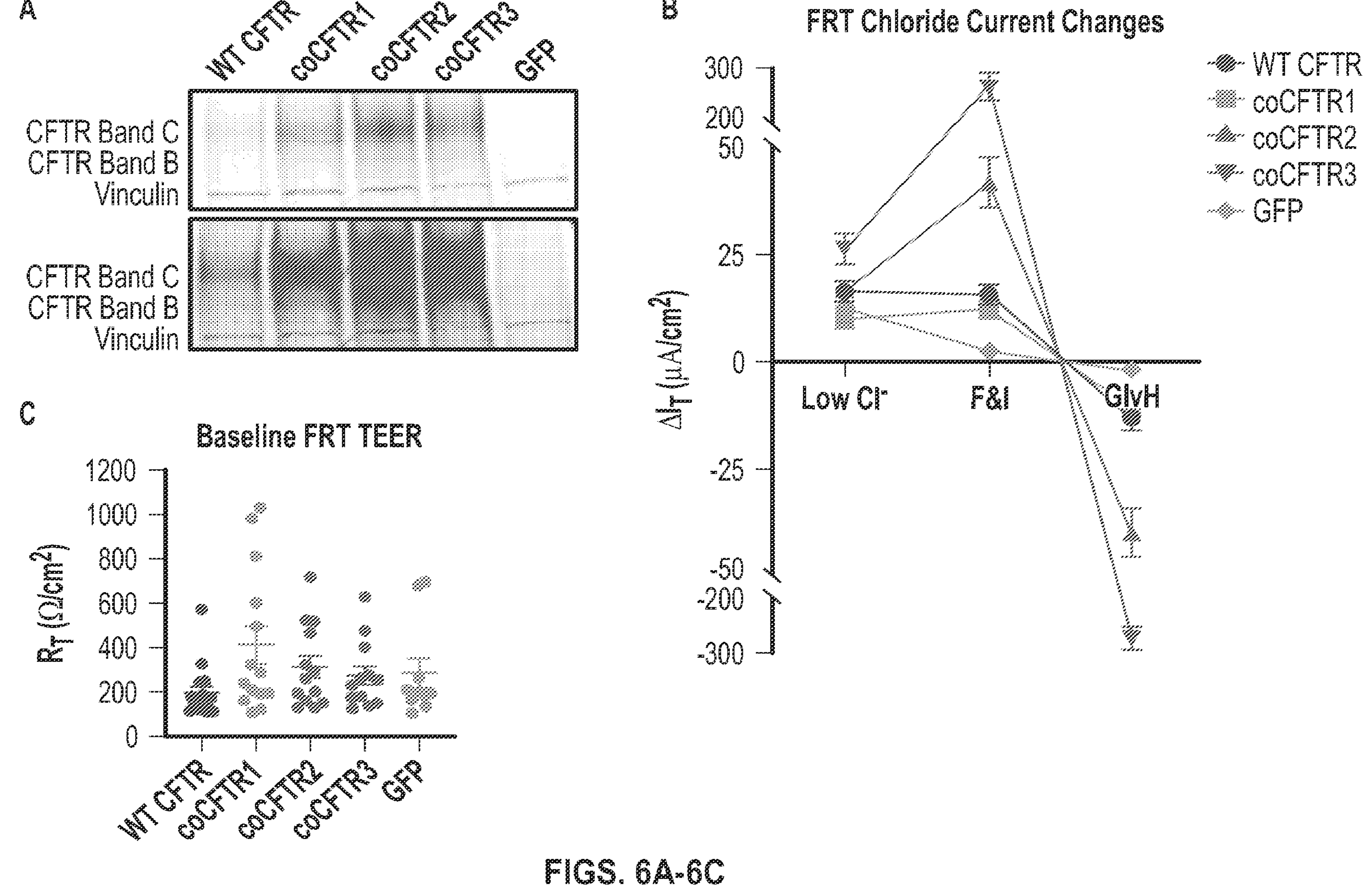
FIGS. 6A-6C are a series of graphs showing that codon optimized CFTR sequences increase protein production and generate unique changes in transepithelial chloride current in FRT cells. FRT cells were transfected with pcDNA3.1 (+) plasmids expressing WT CFTR, coCFTR1, coCFTR2, coCFTR3, or a GFP control.

To test protein function, Fischer rat thyroid (FRT) cells were electroporated with the same plasmids and grown under air-liquid interface conditions. One week later, transepithelial $Cl^-$ current was measured under apical low chloride gradient conditions. FIG. 2D shows the change in current ($\Delta I_T$) in response to the cAMP agonists forskolin and IBMX. Compared to WT CFTR, coCFTR1 did not increase function, while coCFTR2 showed a modest increase. A significant increase with coCFTR3 (SEQ ID NO: 2) was observed compared to WT CFTR (*p<0.0001) (FIGS. 2C-2D). Western blots performed in transfected FRT cells revealed a similar expression pattern as that observed in HEK293 cells, with all coCFTR sequences producing more CFTR compared to WT CFTR (FIGS. 6A-6C).

To confirm that the channel properties were not affected by codon optimization, patch clamp studies were performed in HEK 293 cells transfected with WT CFTR or coCFTR3. Representative tracings are shown in FIG. 2E. The channel open probability, burst duration, and inter-burst intervals were not different between WT CFTR and coCFTR3 (SEQ ID NO: 2), indicating that codon optimization does not change CFTR channel properties (FIG. 2E). These findings indicate that the CFTR channels produced by coCFTR3 have the same properties as those produced by WT CFTR. Furthermore, the increase in CFTR band B associated with coCFTR might be expected since protein processing mechanisms are downstream of those thought to be affected by codon optimization.

Figure 3A:
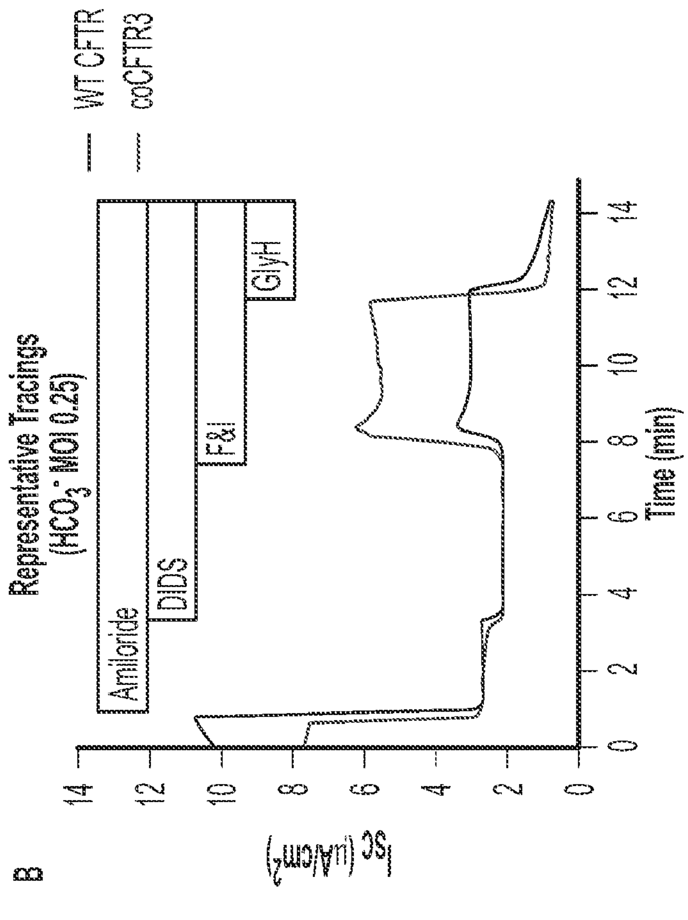
FIG. 3A is a graph showing the estimated transduction efficiency of airway basal progenitor cells from three human CF donors that were isolated and transduced at MOI 0.1, 0.25, 0.5, or 1 with HIV based lentiviral vectors including a PGK promoter and wild-type CFTR transgene, an EF1α promoter and wild-type CFTR transgene, or a PGK promoter and GFP transgene as quantified by flow cytometry after four weeks of differentiation under air-liquid interface conditions. Transduction efficiency was measured by the percent of $GFP^+$ cells.
Figure 3B:
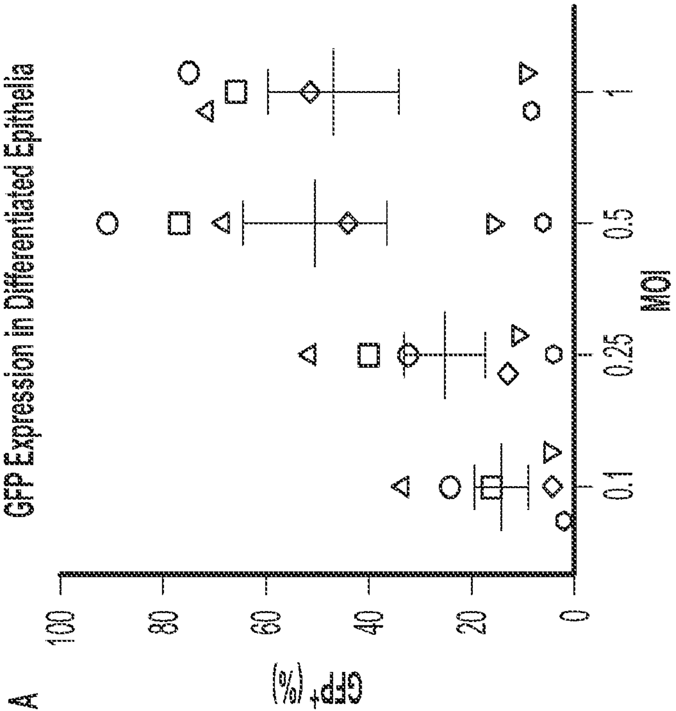
FIG. 3B shows a representative tracings of the current measured when sodium and non-CFTR anion channels were inhibited with amiloride and 4,4'-Diisothiocyano-2,2'-stilbenedisulfonic acid (DIDS) respectively, prior to activation of CFTR channels with cAMP agonists forskolin and IBMX.
Figure 3C:
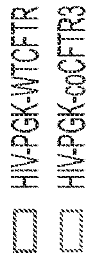
FIGS. 3C and 3D are a series of graphs showing the change in transepithelial CFTR-dependent chloride short circuit current ($\Delta I_{sc}$) in response to F&I (FIG. 3C) or GlyH (FIG. 3D) calculated for transepithelial CI-transport for cells transduced with either the HIV based lentiviral vector including a PGK promoter and wild-type CFTR transgene (on the left side of each MOI) or PGK promoter and coCFTR3 (SEQ ID NO: 2) transgene (on the right side for each MOI). The measurements were made on 2-3 epithelia per condition and each donor is represented by a unique symbol on the graph. HIV-PGK-coCFTR3 resulted in significantly higher chloride current at MOI 0.1 (*$p<0.04$) and higher bicarbonate current at MOI 0.5 and 1 (** $p<0.02$) compared to HIV-PGK-WTCFTR. The results were considered statistically significant if *$p<0.04$. Mean±SE is shown.
Figure 3C:
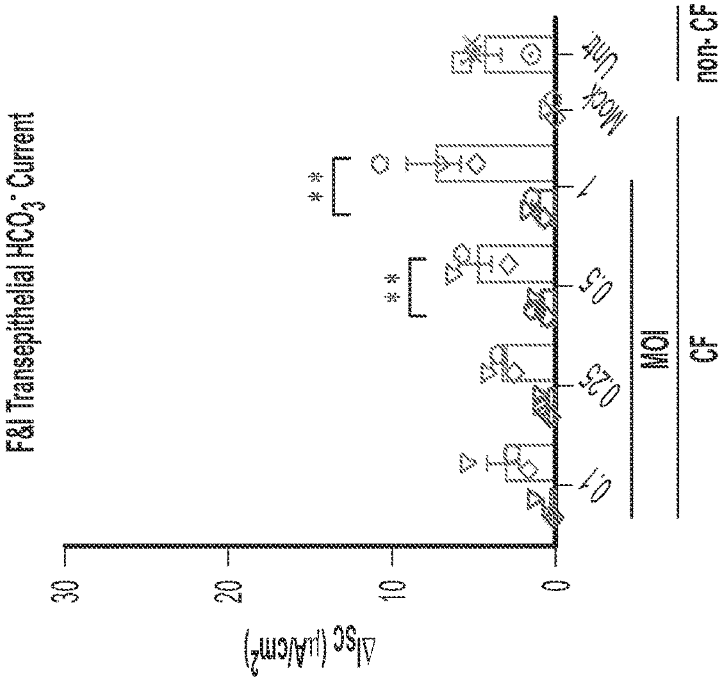
Figure 3C:
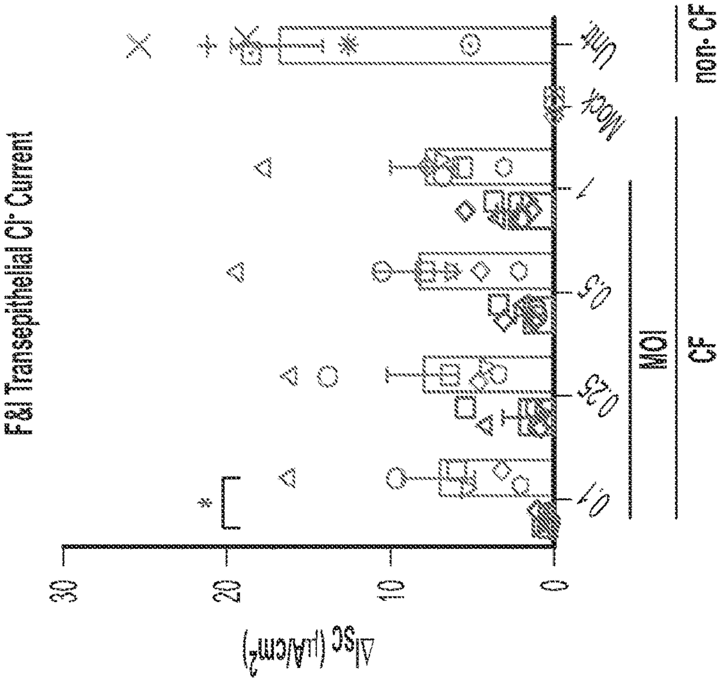
Figure 3D:
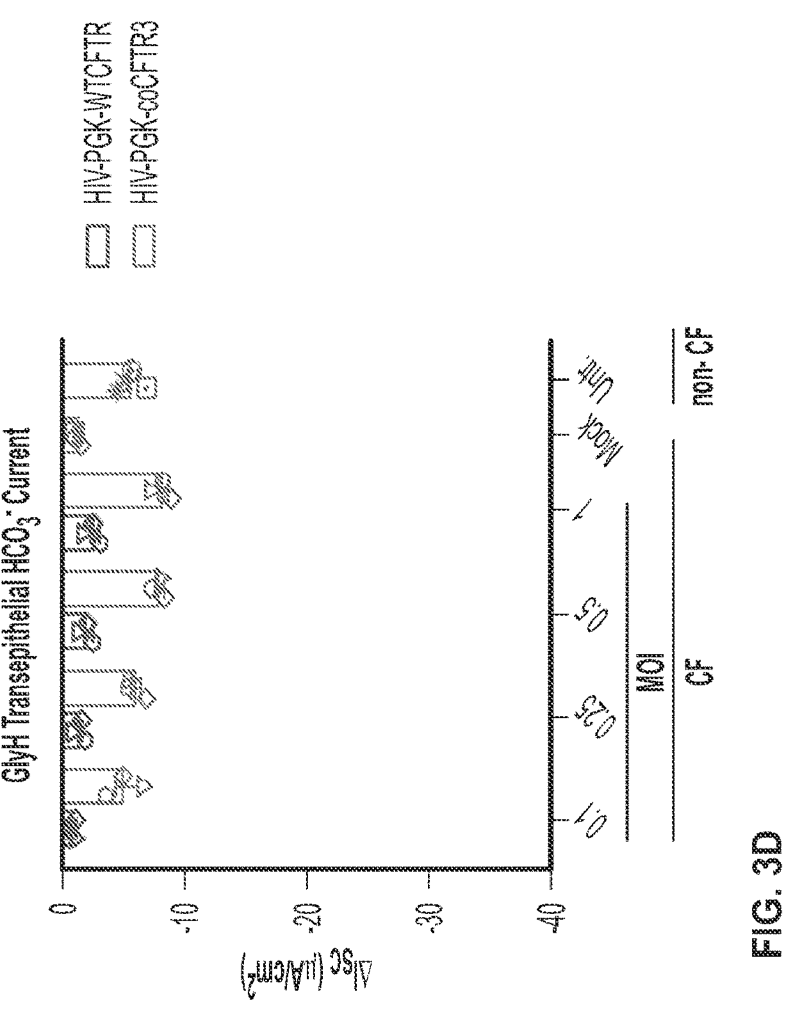
Figure 3D:
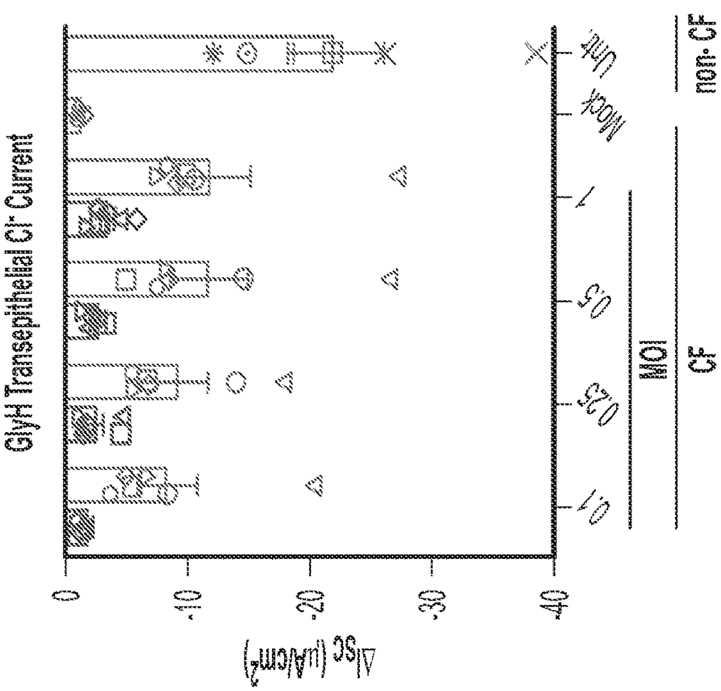
Figures 7A, 7B:
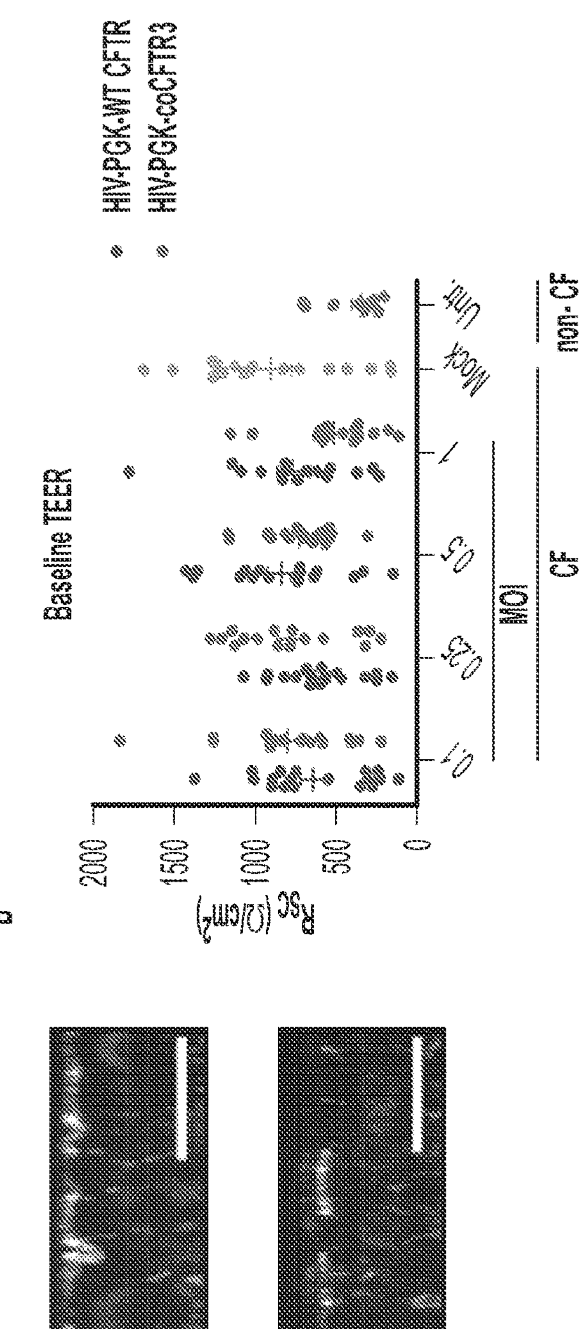
FIGS. 7A and 7B are a series of graphs showing that formation of a differentiated epithelium is not affected by exogenous CFTR expression from a lentiviral vector. CF basal cells were transduced with HIV-PGK-WT CFTR or HIV-PGK-coCFTR3 at MOI 0.1, 0.25, 0.5 or 1 at the time of seeding on semipermeable membranes.

Since expression of coCFTR3 produced the greatest increase in protein function in the FRT cell assay, it was investigated if similar effects would be achieved in primary CF human airway epithelial cells. Given the significant increase in short-circuit current observed with coCFTR3 compared to WT CFTR in FRT cells, PGK was chosen as the promoter since it produced lower currents than EF1α on average (see Example 2) and would allow any effects of codon optimization to be more easily detected. For the same reason, based on the short circuit current dose response observed in the promoter comparison experiments (see Example 2) (FIG. 4E), MOIs≤1 were used. CF progenitor basal cells from five donors were transduced with lentiviral vectors carrying wildtype (WT) CFTR, coCFTR3 (SEQ ID NO: 2), or GFP at MOI 0.1, 0.25, 0.5 and 1 and seeded on polycarbonate membranes. Epithelial cultures were transduced at the time of seeding and allowed to differentiate for four weeks in air-liquid interface culture conditions (see also FIGS. 7A and 7B). These doses were predicted to achieve a range of transduction efficiencies, allowing an optimal MOI to achieve non-CF levels of anion current to be determined. $GFP^+$ cells were quantified by flow cytometry in epithelia transduced with the GFP vector to estimate the number of transduced cells present after differentiation. Donor-dependent differences in transduction permissiveness were observed, resulting in ~2-91% $GFP^+$ cells at the doses tested (FIG. 3A). Epithella transduced with CFTR vectors were mounted in Ussing chambers and transepithelial anion currents were measured. Sodium and anion exchange channels were inhibited with amiloride and DIDS respectively, prior to activation of CFTR channels with cAMP agonists forskolin and IBMX (FIG. 3B). The lentiviral vector encoding coCFTR3 conferred significantly higher transepithelial chloride current at the lowest dose (MOI 0.1, p<0.04) and higher bicarbonate currents at the highest doses (MOI 0.05 and 1, p<0.02) compared to the lentiviral vector encoding WT CFTR (FIGS. 3C and 3D).

The marked increase in chloride current observed with FRT cells (FIG. 2C), combined with the significant increase in the immature (band B) form of CFTR (FIG. 2A), and the increase in CFTR anion currents in primary airway epithelia observed with coCFTR3 (FIG. 2B) raised the possibility that coCFTR3 could have channel properties different from WT CFTR. To study the single channel properties of WT CFTR and coCFTR3, we performed patch-clamp studies in HEK293T cells transfected with WT CFTR or coCFTR3 cDNA (FIG. 2E). No significant differences were found in mean open channel probability, burst duration, or interburst interval (FIG. 2E). These findings indicate that the CFTR channels produced by coCFTR3 have the same properties as those produced by WT CFTR. Furthermore, the increase in CFTR band B associated with coCFTR might be expected since protein processing mechanisms are downstream of those thought to be affected by codon optimization. Together, these results confirmed that coCFTR3 produces more functional CFTR in CF primary human airway epithelial cells, reaching the range of non-CF anion currents at MOIs<1 without changing CFTR channel properties.

Conclusions

Different codon optimization strategies of CFTR described herein increased mRNA and protein production, leading to increased CFTR function as evidenced by increased transepithelial CI transport. Each codon optimization strategy yielded different levels of improved CFTR expression. Lentiviral transduction with coCFTR3 increased transepithelial CI current in primary CF human airway epithelial cells compared to WT CFTR. Codon optimization of CFTR can overcome some of the obstacles of CF gene therapy. Codon optimization of a single protein domain failed to improve expression over WT CFTR. A CFTR codon optimization strategy was identified that significantly increased CFTR-mediated anion transport. Of two different strategies to codon optimize the entire gene, the one that resulted in higher GC and GCs content, coCFTR3, also yielded the highest increase in protein function; without wishing to be bound by theory, these may be characteristics of codon optimization for CFTR.

Example 2: Promoter Selection for CFTR Gene Expression

Figure 4A:
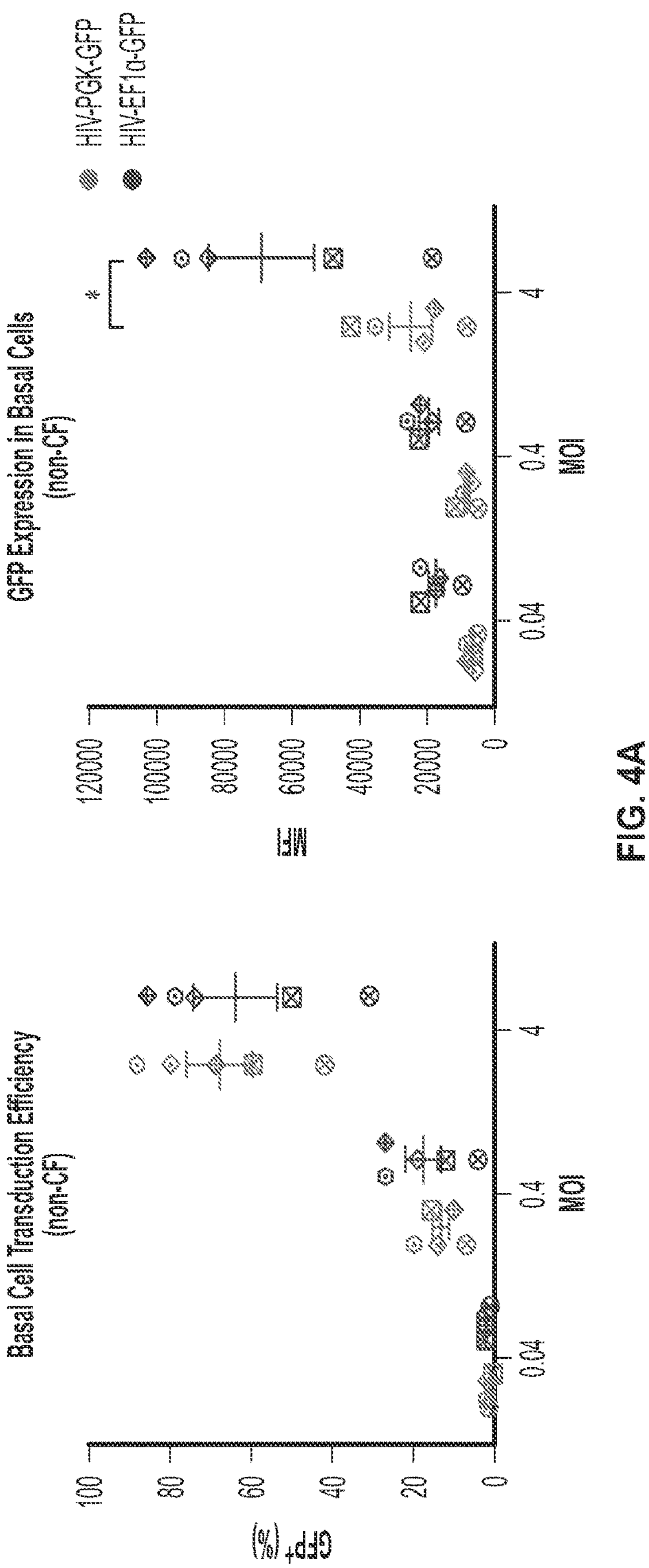
FIG. 4A is a series of graphs showing the estimated transduction efficiency (left panel) and GFP expression (right panel) in basal progenitor cells from five human non-CF donors that were transduced with lentiviral vectors HIV-PGK-GFP or HIV-EF1α-GFP at MOIs of 0.04, 0.4, or 4. $GFP^+$ cells and mean fluorescence intensity (MFI) were quantified by flow cytometry 3-5 days post-transduction. No significant difference was observed in the number of $GFP^+$ cells transduced by either vector at any dose. A significant increase in MFI was observed in cells transduced with HIV-EF1α-GFP compared to HIV-PGK-GFP at MOI 4 (*p<0.0006). Similarly, basal cells from four human CF donors were transduced with lentiviral vectors HIV-PGK-WTCFTR, HIV-EF1α-WTCFTR or HIV-PGK-GFP.
Figure 4B:
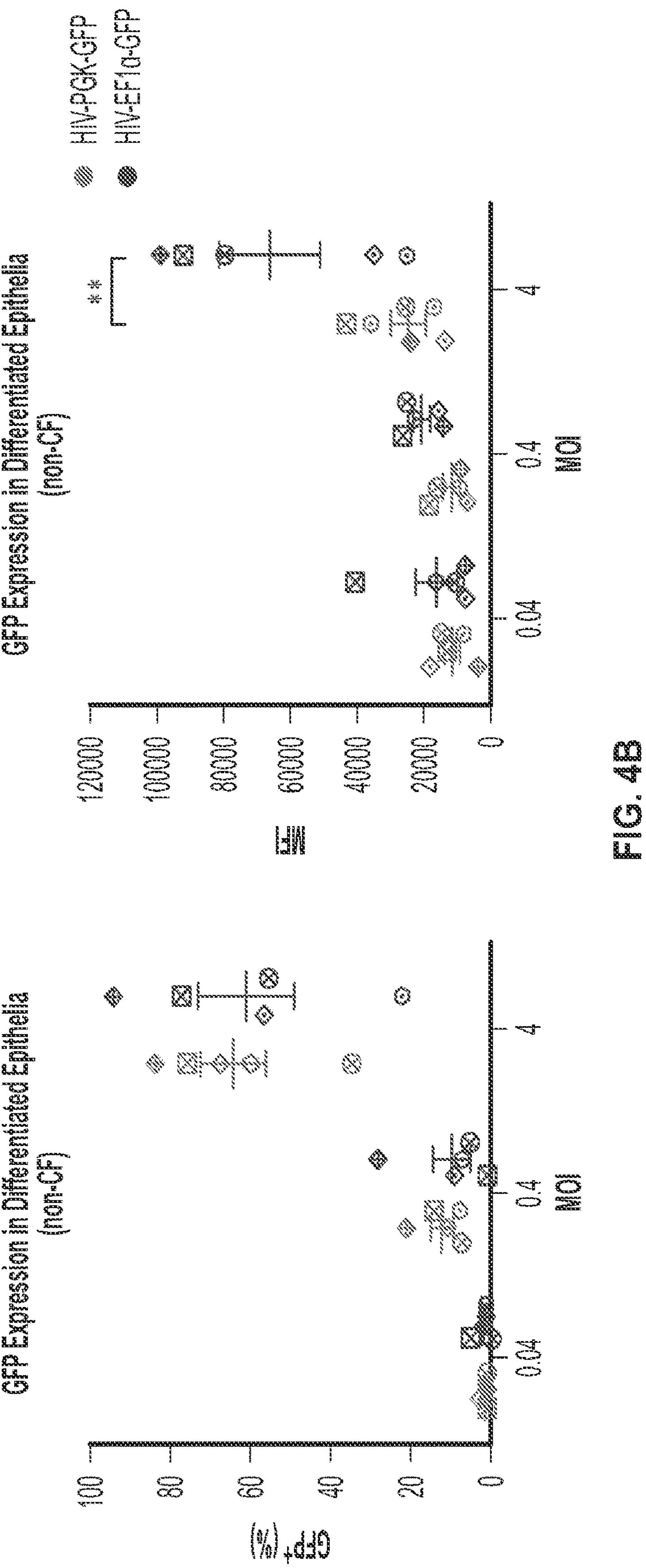
FIG. 4B is a series of graphs showing the percentage of GFP+ cells and MFI from the experiment described in FIG. 4A after 4 weeks of differentiation. No significant difference was observed in the number of GFP+ cells transduced by either vector at any dose. A significant increase in MFI was observed in cells transduced with HIV-EF1α-GFP compared to HIV-PGK-GFP at MOI 4 at both time points (*p<0.0006, ** p<0.002).

To compare the amount of protein produced by vectors with expression of CFTR driven by the PGK or EF1α promoters, GFP was cloned into HIV-based lentiviral vectors that differed only in the promoter (HIV-PGK-GFP and HIV-EF1α-GFP) (FIGS. 5A and 5B), and VSV-G pseudotyped vectors were produced. Basal cells, a progenitor cell type of the conducting airways, from four human cystic fibrosis (CF) donors were transduced with these vectors at MOIs of 0.04, 0.4, and 4 and were analyzed by flow cytometry. Similar numbers of $GFP^+$ cells were observed with both vectors, ranging from <1-88%, among the different MOIs 3-5 days post transduction (FIG. 4A) and after 4 weeks of differentiation in air-liquid interface culture conditions (FIG. 4B). Cells transduced with HIV-EF1α-GFP, however, showed higher mean fluorescence intensity (MFI) at every dose tested compared to cells transduced with HIV-PGK-GFP and this difference was statistically significant at MOI 4 (FIG. 4A, p<0.0006 and FIG. 4B, p<0.002).

Figure 4D:
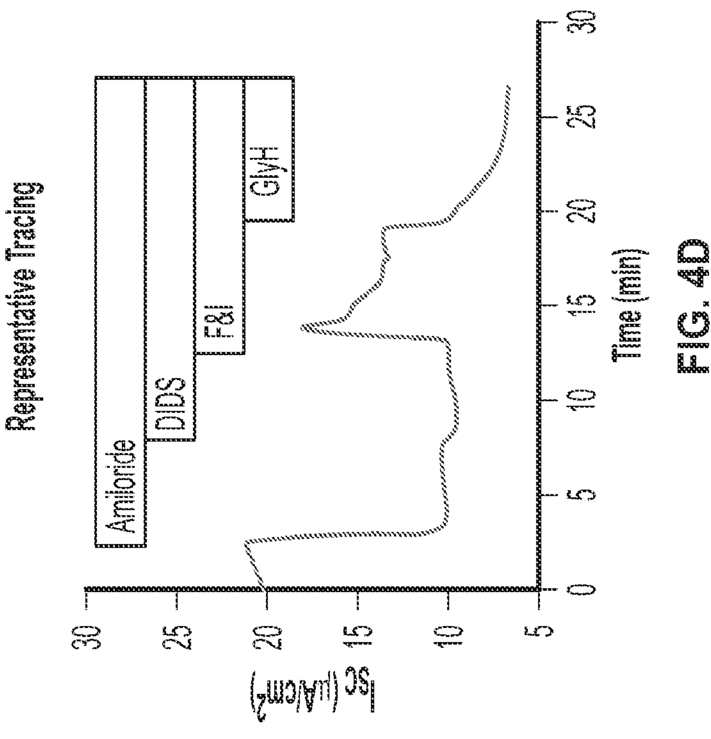
FIG. 4D shows a representative tracing of the transepithelial $Cl^-$ current measured in Ussing chambers where epithelial sodium channels (ENaC) and non-CFTR chloride channels were inhibited with sequential addition of amiloride and 4,4'-Diisothiocyano-2,2'-stilbenedisulfonic acid (DIDS) respectively, prior to activation of CFTR channels with cAMP agonists F&I. The CFTR-specific current was verified by addition of CFTR inhibitor GlyH-101.
Figure 4C:
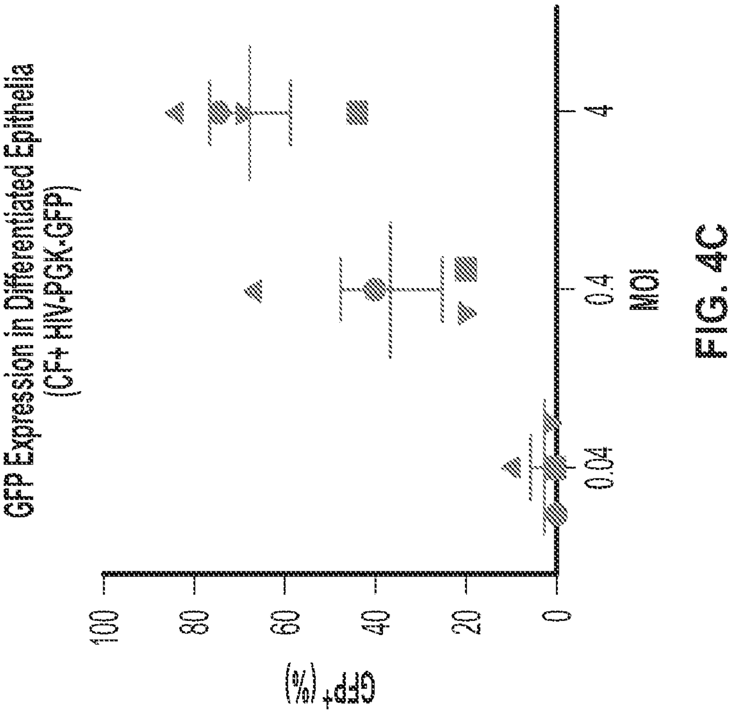
FIG. 4C is a graph showing GFP expression in differentiated epithella after four weeks of differentiation under air-liquid interface conditions; the number of remaining transduced cells was estimated through quantification of $GFP^+$ by flow cytometry. The transduction efficiency was measured by determining the percent of $GFP^+$ cells.

We next transduced basal cells from CF donors with HIV-PGK-WTCFTR, HIV-EF1α-WTCFTR, or HIV-PGK-GFP. In these experiments cells were seeded onto permeable filters at the time of transduction and allowed to differentiate at an air-liquid interface for a minimum of four weeks. The number of transduced cells present after differentiation was estimated by quantifying $GFP^+$ cells by flow cytometry, and ranged from <1-85% (FIG. 4C). CFTR-mediated chloride current was measured in Ussing chambers (FIG. 4D). First, epithelial sodium channels (ENaC) and non-CFTR chloride channels were sequentially inhibited using amiloride and 4,4'-diisothiocyano-2,2'-stilbenedisulfonic acid (DIDS), respectively. CFTR was then stimulated with forskolin and IBMX, and the change in short circuit current was calculated ($\Delta I_{sc}$). Finally, CFTR was inhibited with GlyH 101 (GlyH). At all MOIs tested, HIV-EF1α-WTCFTR produced more CFTR current, on average, compared to HIV-PGK-WTCFTR, but the difference was not statistically significant (FIG. 4E). A condition using HIV-EF1α-GFP was not included in these experiments due to the limited number of primary cells available from each CF donor.

Discussion

Several studies have attempted to approximate the proportion of airway epithelial cells that need to express functional CFTR to correct CF phenotypes, with results ranging from 5-50%. Achieving transduction efficiency as high as 50% in intact airway epithelia using lentiviral vectors is challenging. In vivo studies in the CF pig model demonstrate that some phenotypic tissue correction is achievable, even if transgene expression was below detectable levels by mRNA quantification (see, Cooney et al. (2016). *JCI Insight* 1). Because airway epithelia are electrochemically coupled through gap junctions, supra-physiologic levels of CFTR expression in a small number of cells could be therapeutic.

Promoter choice and codon optimization are two strategies evaluated herein to increase transgene expression. Two constitutive promoters were compared, PGK and EF1α, which are effective at driving expression of mammalian genes and are safely used in clinical trials. In CF airway epithelia, the CFTR currents achieved using the EF1α promoter trended higher than those attained with PGK on average but did not reach statistical significance. When quantifying GFP expression in non-CF cells, similar numbers of $GFP^+$ cells were obtained with PGK or EF1α, and the MFI achieved with the EF1α promoter was higher on average at every dose, reaching statistical significance at the highest dose. The proportion of $GFP^+$ non-CF cells, measured 3-5 days post-transduction, was within expected levels based on a similar transduction protocol. The proportion of CF $GFP^+$ cells, however, represent cells present after the differentiation process and differences in individual cell division rates over that time, which may explain why some values exceed the theoretical maximum for a given MOI.

When comparing WT CFTR and coCFTR3 in primary human CF airway epithelia transduced with a lentiviral vector, HIV-PGK-coCFTR3 significantly increased chloride currents at the lowest vector dose tested (MOI 0.1) (see Example 1). A dose-dependent increase in chloride current with HIV-PGK-WTCFTR was observed, but very similar chloride currents were observed at all doses tested with HIV-PGK-coCFTR3 (see Example 1). This is consistent with previous studies indicating that chloride currents generated by epithelia composed entirely of non-CF cells can be achieved by epithelial sheets consisting of ~50% non-CF and 50% CF cells, and remain stable even when more non-CF cells are added (see, Shah et al. (2016) *Proc Natl Acad Sci USA* 113:5382-5387). This suggests that the maximum chloride current for a given epithelial sheet is achieved at MOI 0.1, explaining why no additional increase is seen at higher MOIs. Likewise, this could also explain why the difference between HIV-PGK-WTCFTR and HIV-EF1α-WTCFTR was not significant at any lowest dose, but GFP expression was significantly higher with EF1α at the highest dose. That is, CFTR-mediated chloride current as a measure of CFTR expression has a lower maximum limit than MFI for GFP expression. CFTR bicarbonate currents, however, continued to increase with CFTR abundance, which is consistent with the dose-dependent increase observed with HIV-PGK-WTCFTR and HIV-PGK-coCFTR3, and the difference between the two was significant at the highest doses (FIG. 3C). Achieving transepithelial anion currents within the range of non-CF at MOI 0.1 with HIV-PGK-coCFTR3 is highly relevant for in vivo studies since likely transducing less than 50% of surface epithelia is anticipated (FIG. 3D).

While EF1α conferred greater WT CFTR-mediated chloride currents and GFP expression, it was noted that its sequence is over twice the length (~1.1 kb) of PGK (~0.5 kb). This is a consideration when coupled with a large cDNA such as CFTR (~4.5 kb) since there is an inverse relationship between lentiviral vector titer and insert length. It is contemplated that the EF1α promoter could be used to drive expression of either wild-type CFTR or codon-optimized CFTR (e.g., coCFTR3). Alternatively, codon-optimized CFTR (e.g., coCFTR3) can be operably linked to other promoters (e.g., PGK). It is anticipated that incorporating EF1α, coCFTR3 or both could lower the proportion of cells that need to be successfully targeted by a lentiviral vector and facilitate sufficient gene delivery to provide clinically relevant CF phenotype correction.

Materials and Methods

Plasmids

HIV-PGK-WTCFTR and HIV-EF1α-GFP were synthesized by Genscript and used to clone HIV-PGK-GFP, HIV-EF1α-coCFTR3 and HIV-EF1α-WTCFTR. The HIV-based vectors used are second generation, self-inactivating (SIN), and contain a human ankyrin 1 element in the reverse orientation within the 3' LTR that improves long-term expression by avoiding silencing.

Viral Vector Production

All viral vectors were produced by the University of Iowa Viral Vector Core. Briefly, a triple transfection (psPAX2, VSV-G, and HIV vector) was performed in HEK293 FT cells using TRANSIT®-Lenti Reagent (Mirus). Cells were cultured in DMEM supplemented with 5% fetal bovine serum (FBS) and 1% penicillin/streptomycin. Vector-containing superatant was collected at 48 and 72 hours. After filtration (0.2 μm) vector was concentrated 750-fold by overnight centrifugation (7000 rpm, 4° C.). The vector pellet was resuspended in 4% D-lactose and stored at −80° C. Vectors were titered in HT1080 cells by flow cytometry for GFP vectors or by TAQMAN® qPCR/digital droplet POR for CFTR vectors using primers: 5'-CGACTGGTGAGTACGCCAAA-3' (SEQ ID NO:10), 5-CGCACCCATCTCTCTCCTTCT-3' (SEQ ID NO:11), and probe 5'-ATTTTGACTAGCGGAGGC-3' (SEQ ID NO: 12).

Transduction and Differentiation of Primary Human Airway Basal Cells

All primary human airway epithelial cells were obtained from the University of Iowa In Vitro Models and Cell Culture Core under approval from the University of Iowa Institutional Review Board. De-identified cells isolated from discarded CF lungs after transplant were provided. $8\times10^5$ freshly isolated primary basal cells from CF donors were seeded on collagen coated 10 cm plates in BRONCHIALIFE® Epithelial Basal Medium (Lifeline). Once cells reached ~80% confluency, cells were dissociated using TRYPLE® (Gibco) and $1\times10^5$ cells were seeded on collagen-coated polycarbonate membrane tissue culture inserts (Corning TRANSWELL®, 6.5 mm, 0.4 μm pore) along with the viral vector and POLYBRENE® (2 μg/ml) in a final volume of 200 μl. 400 μl defined culture media (ULTROSER™ G) was maintained in the basolateral compartment throughout the differentiation process. Cells were maintained under submerged culture conditions for 48-72 hours. Apical media was then removed, and cultures were maintained at air-liquid interface conditions for a minimum of four weeks. Once differentiated, cells were either mounted directly in Ussing chambers for electrophysiology analysis or dissociated for flow cytometry analysis using ACCUMAX® (Sigma).

Transduction of HBE Cells 16HBE14o-cells were cultured in MEM supplemented with 10% FBS, 1% penicillin/streptomycin, and 2 mM L-glutamine. Cells were seeded in 6-well plates and cultured until they reached ~80% confluency. On the day of transduction, cells in one well were counted to calculate vector volume needed for each MOI. The virus was diluted in 1 ml media with POLYBRENE® (2 g/ml) and incubated overnight. Three days post transduction cells were harvested for flow cytometry analysis.

Flow Cytometry

Cells were resuspended in 100 μl PBS containing 2% FBS with LIVE/DEAD™ Fixable Far Red Stain Kit (Invitrogen) and incubated for 30 minutes protected from light. Three washes with 1 ml 2% FBS in PBS were performed before resuspending cells in a final volume of 500 μl for flow cytometry analysis in ATTUNE™ NXT Flow Cytometer (Invitrogen). Doublets, and dead cells were excluded from analysis.

Short-Circuit Measurements

For transepithelial chloride current measurements epithelial cultures were mounted in Ussing chambers, submerged in a solution containing 135 mM NaCl, 5 mM HEPES, 0.6 mM $KH_2PO_4$, 2.4 mM $K_2HPO_4$, 2.2 mM $MgCl_2$, 1.2 mM $CaCl_2$, and 5 mM dextrose, and bubbled with air. For bicarbonate measurements cultures were submerged in a chloride-free solution composed of 118.9 mM Na gluconate, 25 mM $NaHCO_3$, 5 mM Ca gluconate, 1 mM Mg gluconate, 2.4 mM $K_2HPO_4$, 0.6 mM $KH_2PO_4$, 5 mM dextrose, and bubbled with $CO_2$. Amiloride, ENaC inhibitor, and DIDS, a $Cl^-$ exchanger inhibitor, were sequentially added apically to a final concentration of 100 μM. CFTR was then apically activated with the cyclic AMP agonists forskolin and 3-isobutyl-2-methylxanthine (IBMX) at a final concentration of 10 UM and 100 μM, respectively. Finally, the CFTR inhibitor GlyH-101 (Cystic Fibrosis Foundation) was added apically to a final concentration of 100 μM. Changes in short circuit current ($\Delta I_{sc}$) in response to CFTR activation and inhibition were calculated. For FRT transepithelial current measurements, a $Cl^-$ gradient was used. Prior to forskolin and IBMX stimulation, the apical solution was replaced with one in which NaCl was replaced with $NaC_5H_{11}O_7$, and changes in current were calculated ($\Delta I_T$).

Statistics

All data were analyzed using GraphPad Prism 8 software. Statistical significance was determined using one-way ANOVA with Dunn's multiple comparison test, one-way ANOVA on ranks (Kruskal-Wallis test) with Dunn's multiple comparisons test, or multiple t-tests with Bonferroni-Dunn correction as appropriate. Error bars represent mean±SE.

Immunohistochemistry

Epithelia were fixed overnight in 4% paraformaldehyde at 4° C. SuperBlock™ (Thermo Fischer Scientific/Gibco, Waltham, MA) with 0.2% TRITON® X-100 was used to block. Epithella were incubated with an acetylated α-tubulin antibody diluted 1:200 (Cell Signal D20G3 K40, Danvers, MA), before incubating with the secondary antibody ALEXA FLUOR® 568 diluted 1:600 (Invitrogen A11036, Carlsbad, CA). A conjugated phalloidin ALEXA FLUOR® 647 (Invitrogen A22287, Carlsbad, CA) was then used at 1:100 dilution. All incubation steps were done at room temperature for 1 hour, and 3 washes for 10 minutes with TBST were performed between each step. Finally, epithelia were mounted on microscope slides in VECTASHIELD® mounting media with 4',6-diamidino-2-phenylindole (DAPI) (Vector Laboratories, Burlingame, CA).

Sequence Listing

SEQ ID NO: 1

```
ATGCAGCGTAGTCCTCTTGAGAAAGCCAGCGTGGTGAGTAAACTGTTTTTCTCATGGACAAGGC

CCATCCTGCGGAAAGGGTATCGTCAGAGGCTCGAGCTCAGCGACATCTATCAGATACCCTCCGT

TGACTCTGCCGATAACTTGAGTGAAAAACTGGAGCGAGAGTGGGATCGGGAACTGGCATCTAAG

AAGAATCCCAAGCTCATCAACGCCCTGAGAAGATGCTTCTTTTGGAGATTCATGTTTTATGGGATT

TTCCTGTACCTCGGCGAGGTGACCAAGGCAGTGCAGCCTCTTCTTCTGGGCCGGATAATTGCTA

GTTACGACCCAGACAACAAGGAGGAGCGGTCTATAGCCATCTACCTGGGCATTGGGCTCTGTCT

CCTGTTTATCGTGCGTACCCTTCTGCTGCACCCTGCTATTTTCGGCCTGCATCACATCGGGATGC

AGATGCGAATCGCAATGTTCAGCCTAATCTACAAGAAAACACTGAAGCTATCATCCAGAGTGTTG

GATAAGATCAGTATCGGGCAGCTCGTATCCTTGTTGTCTAATAACCTTAATAAGTTCGATGAGGG

CTTAGCACTCGCACACTTTGTATGGATCGCACCACTCCAGGTGGCGCTGCTAATGGGCTTGATAT

GGGAACTTCTCCAGGCTTCAGCATTTTGTGGCCTGGGTTTCTTAATCGTGCTGGCCTTGTTTCAA

GCTGGCTTGGGCAGAATGATGATGAAATACAGAGACCAGAGAGCCGGGAAAATCAGCGAGAGG

CTGGTCATCACATCAGAAATGATCGAAAATATCCAATCGGTAAAGGCCTACTGCTGGGAGGAGG

CTATGGAGAAGATGATTGAGAACCTCAGACAAACCGAACTGAAGCTAACCCGGAAGGCCGCATA

CGTCCGCTATTTCAACTCAAGTGCCTTCTTCTTCTCCGGCTTCTTTGTCGTTTTCCTGTCTGTTCT

TCCTTACGCATTAATCAAAGGTATTATACTCAGGAAGATTTTTACAACCATTTTTTTTGTATTGTC

TTGAGGATGGCCGTAACACGACAATTCCCTTGGGCTGTCCAGACTTGGTACGACTCCCTGGGTG

CCATTAACAAGATCCAGGACTTCCTTCAGAAGCAGGAGTACAAAACCCTGGAATACAATCTTACG

ACCACAGAGGTGGTCATGGAAAATGTTACCGCTTTCTGGGAGGAGGGTTTTGGCGAATTATTTGA

GAAAGCTAAACAGAACAACAATAATCGCAAGACTAGCAATGGCGATGACAGCCTTTTCTTCTCAA

ACTTCTCATTGCTGGGCACTCCGGTCCTGAAGGACATCAACTTTAAGATTGAGCGTGGTCAGCTA
```

-continued

TTGGCCGTTGCCGGAAGCACCGGAGCGGGCAAGACTAGCCTGCTCATGATGATAATGGGCGAG

CTCGAACCCTCAGAGGGAAAAATTAAGCATTCCGGACGCATTAGCTTTTGTTCCCAATTCTCGTG

GATTATGCCCGGCACGATCAAAGAGAACATCATATTCGGAGTCTCTTACGACGAGTACAGGTACC

GGTCTGTAATTAAGGCTTGTCAGCTTGAGGAGGACATTTCTAAATTCGCCGAGAAGGATAATATT

GTGTTAGGAGAÅGGGGGGATAACCCTGAGTGGGGGCCAGAGAGCCAGAATAAGTCTCGCACGC

GCTGTGTACAAAGACGCTGACCTCTACCTGTTAGACTCCCCTTTTGGATACCTGGACGTCTTGAC

CGAAAAGGAGATTTTCGAGTCTTGCGTTTGCAAACTCATGGCCAACAAAACCCGGATACTGGTGA

CTAGCAAAATGGAGCACCTGAAGAAGGCAGATAAGATCCTGATCCTTCACGAGGGCAGCTCTTA

TTTCTACGGCACGTTTTCTGAACTACAGAACCTGCAGCCAGACTTCAGTTCAAAGCTGATGGGTT

GTGATTCCTTTGACCAGTTTTCAGCAGAACGGAGAAACAGTATTCTCACAGAAACTCTCCACAGG

TTCTCCTTAGAGGGGGACGCCCCGGTGAGCTGGACCGAAACTAAAAAACAATCATTCAAGCAGA

CTGGCGAGTTCGGTGAGAAGAGAAAGAACTCCATTCTGAACCCGATCAACTCAATCCGAAAATTC

TCTATTGTGCAGAAGACCCCTTTGCAGATGAACGGCATAGAAGAAGATAGCGATGAGCCATTGG

AGCGCAGACTATCTCTGGTGCCCGATTCCGAGCAGGGTGAAGCTATTTTGCCGAGAATCAGCGT

GATTAGTACCGGTCCAACACTCCAGGCCAGGCGGCGCCAGTCTGTGCTGAATCTGATGACACAC

AGCGTCAATCAGGGTCAAAACATCCACAGAAAGACCACAGCCTCCACTAGAAAGGTTAGTTTAGC

GCCTCAAGCTAACCTCACAGAGCTCGATATCTACTCAAGACGCCTGAGTCAAGAAACGGGATTG

GAGATCAGCGAGGAAATTAATGAGGAGGACTTGAAGGAGTGCCTTTTCGATGACATGGAAAGTA

TCCCCGCCGTGACCACATGGAATACATATCTGCGGTATATCACTGTGCACAAATCTTTGATCTTC

GTGCTGATCTGGTGTCTGGTTATCTTTTTGGCCGAGGTCGCCGCTTCACTGGTGGTTCTTTGGTT

GCTCGGCAATACCCCCCTGCAGGATAAAGGGAACTCAACTCACTCAAGAAACAATAGTTATGCC

GTGATAATTACAAGCACTTCGTCTTATTACGTGTTCTACATCTATGTGGGTGTGGCCGACACTCTA

CTTGCTATGGGATTTTTCCGTGGGCTGCCCCTTGTGCACACATTGATTACCGTAAGCAAAATCCT

CCACCATAAAATGCTGCACTCAGTGCTGCAGGCTCCAATGAGCACTCTCAACACTTTGAAGGCC

GGAGGAATCCTTAATAGGTTTTCTAAGGACATTGCCATTTTGGATGATCTGCTCCCACTGACCATT

TTCGATTTCATTCAACTCCTCCTGATCGTGATTGGCGCAATTGCCGTGGTTGCTGTGTTACAGCC

CTATATTTTCGTGGCGACAGTGCCCGTTATTGTGGCTTTCATCATGCTGCGTGCCTACTTCCTTC

AGACCAGTCAACAACTCAAGCAGCTTGAGTCAGAGGGCCGCTCCCCGATTTTCACCCATCTGGT

CACGTCTCTTAAAGGCCTGTGGACCCTGAGGGCCTTTGGGAGGCAGCCCTATTTTGAAACCCTC

TTTCACAAGGCTCTGAATTTGCACACTGCCAATTGGTTCCTCTACTTGTCAACTCTCAGGTGGTTC

CAGATGAGAATCGAAATGATCTTTGTGATCTTTTTCATCGCAGTCACTTTTATAAGCATCCTGACC

ACCGGCGAAGGGGAGGGGGGGGTCGGAATCATCTTAACTCTGGCCATGAATATTATGAGCACTC

TACAATGGGCCGTGAATAGCTCAATTGATGTGGACTCGCTGATGAGAAGCGTGAGCCGCGTCTT

TAAATTCATTGACATGCCAACTGAAGGCAAGCCAACGAAGAGTACTAAGCCTTATAAAAACGGCC

AACTGTCAAAGGTCATGATTATCGAAAATTCCCATGTGAAGAAAGACGACATTTGGCCCTCTGGA

GGACAGATGACCGTCAAGGATCTCACCGCAAAATATACTGAGGGCGGGAACGCCATTTTGGAAA

ACATCTCGTTTTCTATCAGCCCCGGTCAGAGAGTCGGTCTGCTCGGCAGGACTGGATCTGGGAA

ATCCACTTTGTTATCCGCTTTCCTCCGCCTTCTGAACACCGAGGGGGAGATCCAGATTGATGGAG

TGAGCTGGGATTCGATCACTCTGCAGCAGTGGCGGAAGGCCTTTGGCGTGATCCCTCAGAAAGT

GTTTATCTTTTCCGGGACCTTTCGAAAGAATCTCGATCCTTACGAGCAGTGGTCTGACCAAGAAA

TCTGGAAAGTCGCTGACGAGGTGGGGCTGAGGTCTGTAATCGAGCAGTTCCCTGGGAAACTCG

-continued

ATTTTGTGCTTGTGGACGGCGGATGTGTACTGTCTCATGGACACAAGCAATTGATGTGCCTGGCA

CGCAGCGTGCTCTCGAAGGCTAAGATACTTCTGCTGGACGAACCATCAGCACACTTAGATCCAG

TGACATATCAAATCATCAGGCGAACCCTGAAACAAGCATTCGCAGATTGTACCGTGATCCTGTGT

GAACATCGGATTGAGGCCATGCTGGAGTGCCAGCAGTTTCTGGTCATTGAGGAAAACAAGGTTC

GCCAGTACGATTCGATCCAAAAATTACTGAATGAGAGATCACTGTTTAGGCAGGCCATTTCACCC

AGCGACCGTGTAAAGTTGTTTCCTCACCGAAACTCGAGTAAATGCAAATCTAAGCCACAGATTGC

AGCCCTGAAAGAGGAGACAGAGGAGGAGGTGCAAGACACCAGGTTGTAG

SEQ ID NO: 2

ATGCAGCGCAGCCCCCTGGAGAAGGCCAGCGTGGTGAGCAAGCTGTTCTTCAGCTGGACCCGC

CCCATCCTGCGCAAGGGCTACCGCCAGCGCCTGGAGCTGAGCGACATCTACCAGATCCCCAGC

GTGGACAGCGCCGACAACCTGAGCGAGAAGCTGGAGCGCGAGTGGGACCGCGAGCTGGCCAG

CAAGAAGAACCCCAAGCTGATCAACGCCCTGCGCCGCTGCTTCTTCTGGCGCTTCATGTTCTAC

GGCATCTTCCTGTACCTGGGCGAGGTGACCAAGGCCGTGCAGCCCCTGCTGCTGGGCCGCATC

ATCGCCAGCTACGACCCCGACAACAAGGAGGAGCGCAGCATCGCCATCTACCTGGGCATCGGC

CTGTGCCTGCTGTTCATCGTGCGCACCCTGCTGCTGCACCCCGCCATCTTCGGCCTGCACCACA

TCGGCATGCAGATGCGCATCGCCATGTTCAGCCTGATCTACAAGAAGACCCTGAAGCTGAGCAG

CCGCGTGCTGGACAAGATCAGCATCGGCCAGCTGGTGAGCCTGCTGAGCAACAACCTGAACAA

GTTCGACGAGGGCCTGGCCCTGGCCCACTTCGTGTGGATCGCCCCCCTGCAGGTGGCCCTGCT

GATGGGCCTGATCTGGGAGCTGCTGCAGGCCAGCGCCTTCTGCGGCCTGGGCTTCCTGATCGT

GCTGGCCCTGTTCCAGGCCGGCCTGGGCCGCATGATGATGAAGTACCGCGACCAGCGCGCCG

GCAAGATCAGCGAGCGCCTGGTGATCACCAGCGAGATGATCGAGAACATCCAGAGCGTGAAGG

CCTACTGCTGGGAGGAGGCCATGGAGAAGATGATCGAGAACCTGCGCCAGACCGAGCTGAAGC

TGACCCGCAAGGCCGCCTACGTGCGCTACTTCAACAGCAGCGCCTTCTTCTTCAGCGGCTTCTT

CGTGGTGTTCCTGAGCGTGCTGCCCTACGCCCTGATCAAGGGCATCATCCTGCGCAAGATCTTC

ACCACCATCAGCTTCTGCATCGTGCTGCGCATGGCCGTGACCCGCCAGTTCCCCTGGGCCGTG

CAGACCTGGTACGACAGCCTGGGCGCCATCAACAAGATCCAGGACTTCCTGCAGAAGCAGGAG

TACAAGACCCTGGAGTACAACCTGACCACCACCGAGGTGGTGATGGAGAACGTGACCGCCTTCT

GGGAGGAGGGCTTCGGCGAGCTGTTCGAGAAGGCCAAGCAGAACAACAACAACCGCAAGACCA

GCAACGGCGACGACAGCCTGTTCTTCAGCAACTTCAGCCTGCTGGGCACCCCCGTGCTGAAGG

ACATCAACTTCAAGATCGAGCGCGGCCAGCTGCTGGCCGTGGCCGGCAGCACCGGCGCCGGC

AAGACCAGCCTGCTGATGATGATCATGGGCGAGCTGGAGCCCAGCGAGGGCAAGATCAAGCAC

AGCGGCCGCATCAGCTTCTGCAGCCAGTTCAGCTGGATCATGCCCGGCACCATCAAGGAGAAC

ATCATCTTCGGCGTGAGCTACGACGAGTACCGCTACCGCAGCGTGATCAAGGCCTGCCAGCTG

GAGGAGGACATCAGCAAGTTCGCCGAGAAGGACAACATCGTGCTGGGCGAGGGGGGCATCACC

CTGAGCGGCGGCCAGCGCGCCCGCATCAGCCTGGCCCGCGCCGTGTACAAGGACGCCGACCT

GTACCTGCTGGACAGCCCCTTCGGCTACCTGGACGTGCTGACCGAGAAGGAGATCTTCGAGAG

CTGCGTGTGCAAGCTGATGGCCAACAAGACCCGCATCCTGGTGACCAGCAAGATGGAGCACCT

GAAGAAGGCCGACAAGATCCTGATCCTGCACGAGGGCAGCAGCTACTTCTACGGCACCTTCAGC

GAGCTGCAGAACCTGCAGCCCGACTTCAGCAGCAAGCTGATGGGCTGCGACAGCTTCGACCAG

TTCAGCGCCGAGCGCCGCAACAGCATCCTGACCGAGACCCTGCACCGCTTCAGCCTGGAGGGC

GACGCCCCCGTGAGCTGGACCGAGACCAAGAAGCAGAGCTTCAAGCAGACCGGCGAGTTCGGC

-continued

GAGAAGCGCAAGAACAGCATCCTGAACCCCATCAACAGCATCCGCAAGTTCAGCATCGTGCAGA

AGACCCCCCTGCAGATGAACGGCATCGAGGAGGACAGCGACGAGCCCCTGGAGCGCCGCCTG

AGCCTGGTGCCCGACAGCGAGCAGGGCGAGGCCATCCTGCCCCGCATCAGCGTGATCAGCAC

CGGCCCCACCCTGCAGGCCCGCCGCCGCCAGAGCGTGCTGAACCTGATGACCCACAGCGTGA

ACCAGGGCCAGAACATCCACCGCAAGACCACCGCCAGCACCCGCAAGGTGAGCCTGGCCCCCC

AGGCCAACCTGACCGAGCTGGACATCTACAGCCGCCGCCTGAGCCAGGAGACCGGCCTGGAGA

TCAGCGAGGAGATCAACGAGGAGGACCTGAAGGAGTGCTTCTTCGACGACATGGAGAGCATCC

CCGCCGTGACCACCTGGAACACCTACCTGCGCTACATCACCGTGCACAAGAGCCTGATCTTCGT

GCTGATCTGGTGCCTGGTGATCTTCCTGGCCGAGGTGGCCGCCAGCCTGGTGGTGCTGTGGCT

GCTGGGCAACACCCCCCTGCAGGACAAGGGCAACAGCACCCACAGCCGCAACAACAGCTACGC

CGTGATCATCACCAGCACCAGCAGCTACTACGTGTTCTACATCTACGTGGGCGTGGCCGACACC

CTGCTGGCCATGGGCTTCTTCCGCGGCCTGCCCCTGGTGCACACCCTGATCACCGTGAGCAAG

ATCCTGCACCACAAGATGCTGCACAGCGTGCTGCAGGCCCCCATGAGCACCCTGAACACCCTGA

AGGCCGGGGGCATCCTGAACCGCTTCAGCAAGGACATCGCCATCCTGGACGACCTGCTGCCCC

TGACCATCTTCGACTTCATCCAGCTGCTGCTGATCGTGATCGGCGCCATCGCCGTGGTGGCCGT

GCTGCAGCCCTACATCTTCGTGGCCACCGTGCCCGTGATCGTGGCCTTCATCATGCTGCGCGCC

TACTTCCTGCAGACCAGCCAGCAGCTGAAGCAGCTGGAGAGCGAGGGCCGCAGCCCCATCTTC

ACCCACCTGGTGACCAGCCTGAAGGGCCTGTGGACCCTGCGCGCCTTCGGCCGCCAGCCCTAC

TTCGAGACCCTGTTCCACAAGGCCCTGAACCTGCACACCGCCAACTGGTTCCTGTACCTGAGCA

CCCTGCGCTGGTTCCAGATGCGCATCGAGATGATCTTCGTGATCTTCTTCATCGCCGTGACCTTC

ATCAGCATCCTGACCACCGGCGAGGGCGAGGGCCGCGTGGGCATCATCCTGACCCTGGCCATG

AACATCATGAGCACCCTGCAGTGGGCCGTGAACAGCAGCATCGACGTGGACAGCCTGATGCGC

AGCGTGAGCCGCGTGTTCAAGTTCATCGACATGCCCACCGAGGGCAAGCCCACCAAGAGCACC

AAGCCCTACAAGAACGGCCAGCTGAGCAAGGTGATGATCATCGAGAACAGCCACGTGAAGAAG

GACGACATCTGGCCCAGCGGCGGCCAGATGACCGTGAAGGACCTGACCGCCAAGTACACCGAG

GGCGGCAACGCCATCCTGGAGAACATCAGCTTCAGCATCAGCCCCGGCCAGCGCGTGGGCCTG

CTGGGCCGCACCGGCAGCGGCAAGAGCACCCTGCTGAGCGCCTTCCTGCGCCTGCTGAACACC

GAGGGCGAGATCCAGATCGACGGCGTGAGCTGGGACAGCATCACCCTGCAGCAGTGGCGCAA

GGCCTTCGGCGTGATCCCCCAGAAGGTGTTCATCTTCAGCGGCACCTTCCGCAAGAACCTGGAC

CCCTACGAGCAGTGGAGCGACCAGGAGATCTGGAAGGTGGCCGACGAGGTGGGCCTGCGCAG

CGTGATCGAGCAGTTCCCCGGCAAGCTGGACTTCGTGCTGGTGGACGGCGGCTGCGTGCTGAG

CCACGGCCACAAGCAGCTGATGTGCCTGGCCCGCAGCGTGCTGAGCAAGGCCAAGATCCTGCT

GCTGGACGAGCCCAGCGCCCACCTGGACCCCGTGACCTACCAGATCATCCGCCGCACCCTGAA

GCAGGCCTTCGCCGACTGCACCGTGATCCTGTGCGAGCACCGCATCGAGGCCATGCTGGAGTG

CCAGCAGTTCCTGGTGATCGAGGAGAACAAGGTGCGCCAGTACGACAGCATCCAGAAGCTGCT

GAACGAGCGCAGCCTGTTCCGCCAGGCCATCAGCCCCAGCGACCGCGTGAAGCTGTTCCCCCA

CCGCAACAGCAGCAAGTGCAAGAGCAAGCCCCAGATCGCCGCCCTGAAGGAGGAGACCGAGG

AGGAGGTGCAGGACACCCGCCTGTAA

SEQ ID NO: 3

ATGCAGCGGAGCCCTCTTGAGAAAGCCAGCGTGGTGTCCAAGCTGTTCTTCAGCTGGACCCGG

CCTATCCTGAGAAAGGGCTACAGACAGAGACTGGAACTGAGCGACATCTATCAGATCCCCAGCG

-continued

TGGACAGCGCCGACAATCTGAGCGAGAAGCTGGAAAGAGAGTGGGACAGAGAGCTGGCCTCCA

AGAAGAACCCCAAGCTGATCAACGCCCTGCGGAGATGCTTCTTCTGGCGGTTTATGTTCTACGG

CATCTTCCTGTACCTGGGCGAAGTGACAAAAGCCGTGCAGCCTCTGCTGCTGGGCAGAATCATT

GCCAGCTACGACCCCGACAACAAAGAGGAACGGTCTATCGCCATCTACCTCGGCATCGGCCTGT

GCCTGCTGTTTATTGTCAGAACCCTGCTGCTGCACCCCGCCATCTTTGGACTGCACCACATCGG

CATGCAGATGCGGATCGCCATGTTCAGCCTGATCTACAAGAAAACCCTGAAGCTGTCCAGCCGA

GTGCTGGACAAGATCTCTATCGGACAGCTGGTGTCCCTGCTGAGCAACAACCTGAACAAGTTCG

ACGAAGGCCTGGCTCTGGCCCACTTTGTGTGGATTGCTCCTCTGCAAGTGGCCCTGCTGATGGG

ACTGATTTGGGAACTGCTGCAGGCCAGCGCCTTTTGTGGCCTGGGATTTCTGATCGTGCTGGCC

CTGTTTCAGGCCGGACTGGGAAGAATGATGATGAAGTACAGGGACCAGAGAGCCGGCAAGATC

AGCGAGAGACTGGTCATCACCAGCGAGATGATCGAGAACATCCAGAGCGTGAAGGCCTACTGCT

GGGAAGAGGCCATGGAAAAGATGATTGAGAATCTGCGGCAGACCGAGCTGAAGCTGACAAGAA

AGGCCGCCTACGTGCGGTACTTCAACAGCAGCGCCTTCTTCTTCTCCGGCTTCTTCGTGGTGTT

CCTGAGCGTGCTGCCCTACGCTCTGATCAAGGGCATCATCCTGCGGAAGATCTTTACGACAATC

AGCTTCTGCATTGTGCTGCGGATGGCCGTGACCAGACAGTTTCCTTGGGCTGTGCAGACTTGGT

ACGATAGCCTGGGCGCCATCAACAAGATCCAGGACTTCCTGCAGAAGCAAGAGTACAAGACCCT

CGAGTACAACCTGACCACCACCGAGGTGGTCATGGAAAACGTGACCGCCTTCTGGGAGGAAGG

CTTCGGCGAGCTGTTTGAGAAGGCCAAGCAGAACAACAACAACCGCAAGACCAGCAACGGCGA

CGACAGCCTGTTCTTCTCCAATTTCTCTCTGCTGGGGACCCCTGTGCTGAAGGACATCAACTTCA

AGATCGAGCGGGGACAGCTGCTGGCCGTTGCAGGATCTACAGGCGCCGGAAAGACAAGTCTGC

TGATGATGATCATGGGCGAGCTGGAACCCAGCGAGGGAAAGATCAAGCACAGCGGCCGGATTA

GCTTCTGTAGCCAGTTCTCCTGGATCATGCCCGGCACCATCAAAGAGAACATCATCTTCGGCGT

GTCCTACGACGAGTACAGATACAGAAGCGTGATCAAGGCCTGCCAGCTGGAAGAGGACATCAG

CAAGTTCGCCGAGAAGGACAACATCGTGCTCGGCGAAGGGGGAATCACACTGTCTGGCGGCCA

GAGGGCTAGAATCTCTCTGGCTAGAGCCGTGTACAAGGACGCCGATCTGTACCTGCTGGATAGC

CCCTTTGGCTACCTGGACGTGCTGACCGAGAAAGAGATCTTCGAGAGCTGCGTGTGCAAGCTGA

TGGCCAACAAGACCAGAATCCTCGTGACCAGCAAGATGGAACACCTGAAGAAGGCCGACAAGAT

CCTGATCCTGCACGAGGGCAGCAGCTACTTTTACGGCACCTTCAGCGAACTGCAGAACCTGCAG

CCTGACTTCAGCAGCAAACTGATGGGCTGCGACTCCTTCGATCAGTTCAGCGCCGAGCGGAGAA

ACAGCATCCTGACAGAGACACTGCACAGATTCAGCCTGGAAGGCGACGCCCCTGTGTCTTGGAC

CGAGACAAAGAAGCAGAGCTTCAAGCAGACCGGCGAGTTTGGCGAGAAGAGAAAGAACAGCAT

TCTGAACCCCATCAACTCCATCCGGAAGTTCAGCATCGTGCAGAAAACCCCTCTGCAGATGAAC

GGCATCGAAGAGGATAGCGACGAGCCCCTGGAAAGACGACTGAGCCTGGTGCCTGATTCTGAG

CAGGGCGAAGCCATCCTGCCTAGAATTTCCGTGATCAGCACTGGCCCCACACTGCAGGCTCGAA

GAAGGCAGTCTGTCCTGAACCTGATGACCCACAGCGTGAACCAGGGACAGAATATCCACAGAAA

GACCACCGCCAGCACACGGAAAGTTTCTCTGGCACCTCAGGCCAACCTGACTGAGCTGGACATC

TACAGCAGACGGCTGAGCCAAGAGACAGGCCTGGAAATCAGCGAGGAAATCAACGAAGAGGAC

CTGAAAGAGTGCTTCTTCGACGACATGGAATCTATCCCCGCCGTGACAACCTGGAACACATACCT

GCGGTACATCACCGTGCACAAGTCCCTGATCTTCGTGCTGATCTGGTGCCTCGTGATCTTTCTG

GCCGAAGTGGCTGCTTCTCTGGTGGTTCTGTGGCTGCTCGGAAACACCCCACTGCAGGATAAGG

-continued

GCAACAGCACCCACAGCAGAAACAACAGCTACGCCGTGATCATCACCTCCACCAGCTCCTACTA

CGTGTTCTACATCTACGTCGGCGTGGCCGACACACTGCTGGCCATGGGCTTTTTTAGAGGACTG

CCTCTGGTGCACACCCTGATCACCGTGTCCAAGATTCTGCACCATAAGATGCTGCACAGCGTCC

TGCAGGCCCCTATGAGCACACTGAATACTCTGAAGGCTGGGGGCATCCTGAACAGGTTCAGCAA

GGACATTGCCATCCTGGACGACCTGCTGCCTCTGACCATCTTCGACTTCATCCAGCTGCTGCTG

ATCGTGATCGGAGCCATTGCTGTGGTGGCCGTGCTGCAGCCTTATATCTTTGTGGCCACCGTGC

CTGTGATCGTGGCCTTCATTATGCTGCGGGCCTACTTTCTGCAGACCTCTCAGCAGCTGAAGCA

GCTCGAGTCTGAGGGCAGAAGCCCTATCTTTACCCACCTGGTCACCAGCCTGAAAGGCCTGTGG

ACACTGAGAGCCTTCGGCAGGCAGCCTTACTTCGAGACACTGTTCCACAAGGCCCTGAATCTGC

ACACCGCCAACTGGTTCCTCTACCTGAGCACCCTGCGGTGGTTCCAGATGAGAATCGAGATGAT

TTTCGTCATCTTCTTTATCGCCGTGACCTTCATCTCCATTCTGACCACTGGCGAAGGCGAGGGCA

GAGTGGGAATTATCCTGACACTGGCCATGAACATCATGTCTACCCTCCAGTGGGCCGTGAACÅG

CAGCATCGATGTGGACAGCCTGATGCGGAGCGTGTCCCGGGTGTTCAAGTTCATCGATATGCCC

ACCGAGGGCAAGCCCACCAAGAGCACCAAGCCTTACAAGAATGGCCAGCTGAGCAAAGTGATG

ATTATCGAGAACTCCCACGTGAAGAAGGACGATATCTGGCCCAGCGGCGGACAGATGACCGTGA

AAGATCTGACCGCCAAGTACACCGAAGGCGGCAACGCCATTCTGGAAAACATCAGCTTTAGCAT

CAGCCCTGGCCAGAGAGTCGGACTGCTTGGCAGAACAGGCAGCGGAAAGTCTACCCTGCTGTC

CGCCTTCCTGAGACTGCTGAATACCGAGGGCGAGATCCAGATCGATGGGGTGTCCTGGGATAG

CATCACACTCCAACAGTGGCGGAAGGCCTTTGGCGTGATCCCTCAGAAGGTGTTCATTTTCAGC

GGCACCTTTCGGAAGAATCTGGACCCCTACGAGCAGTGGTCCGACCAAGAGATTTGGAAGGTG

GCCGACGAAGTGGGCCTGAGATCTGTGATCGAGCAGTTTCCCGGCAAGCTGGATTTCGTGCTG

GTGGATGGCGGATGTGTGCTGTCTCACGGACACAAGCAGCTGATGTGCCTGGCTAGAAGCGTG

CTGTCTAAGGCCAAGATCCTCCTGCTGGACGAGCCCTCTGCACATCTGGATCCTGTGACCTACC

AGATCATCCGGCGGACACTGAAGCAGGCCTTTGCCGATTGCACCGTGATCCTGTGCGAGCACA

GAATCGAGGCCATGCTGGAATGCCAGCAGTTTCTCGTGATCGAAGAGAACAAAGTGCGGCAGTA

CGACAGCATCCAGAAGCTGCTGAACGAGCGGAGCCTGTTCAGACAGGCCATCTCTCCCAGCGA

CAGAGTGAAGCTGTTCCCTCACCGGAACAGCTCCAAGTGCAAGAGCAAGCCTCAGATCGCCGCT

CTGAAAGAAGAAACCGAGGAAGAGGTGCAGGACACCAGACTCTGA

SEQ ID NO: 4

TCGAATTCCCACGGGGTTGGGGTTGCGCCTTTTCCAAGGCAGCCCTGGGTTTGCGCAGGGACG

CGGCTGCTCTGGGCGTGGTTCCGGGAAACGCAGCGGCGCCGACCCTGGGTCTCGCACATTCTT

CACGTCCGTTCGCAGCGTCACCCGGATCTTCGCCGCTACCCTTGTGGGCCCCCCGGCGACGCT

TCCTGCTCCGCCCCTAAGTCGGGAAGGTTCCTTGCGGTTCGCGGCGTGCCGGACGTGACAAAC

GGAAGCCGCACGTCTCACTAGTACCCTCGCAGACGGACAGCGCCAGGGAGCAATGGCAGCGC

GCCGACCGCGATGGGCTGTGGCCAATAGCGGCTGCTCAGCGGGGCGCGCCGAGAGCAGCGGC

CGGGAAGGGGCGGTGCGGGAGGCGGGGTGTGGGGCGGTAGTGTGGGCCCTGTTCCTGCCCG

CGCGGTGTTCCGCATTCTGCAAGCCTCCGGAGCGCACGTCGGCAGTCGGCTCCCTCGTTGACC

GAATCACCGACCTCTCTCCCCAG

SEQ ID NO: 5 ataTCGGCTCCGGTGCCCGTCAGTGGGCAGAGCGCACATCGCCCACAGTCCCCGAGAAGTTGGG

GGGAGGGGTCGGCAATTGAACCGGTGCCTAGAGAAGGTGGCGCGGGGTAAACTGGGAAAGTG

ATGTCGTGTACTGGCTCCGCCTTTTTCCCGAGGGTGGGGGAGAACCGTATATAAGTGCAGTAGT

-continued

CGCCGTGAACGTTCTTTTTCGCAACGGGTTTGCCGCCAGAACACAGGTAAGTGCCGTGTGTGGT

TCCCGCGGGCCTGGCCTCTTTACGGGTTATGGCCCTTGCGTGCCTTGAATTACTTCCACGCCCC

TGGCTGCAGTACGTGATTCTTGATCCCGAGCTTCGGGTTGGAAGTGGGTGGGAGAGTTCGAGG

CCTTGCGCTTAAGGAGCCCCTTCGCCTCGTGCTTGAGTTGAGGCCTGGCCTGGGCGCTGGGGC

CGCCGCGTGCGAATCTGGTGGCACCTTCGCGCCTGTCTCGCTGCTTTCGATAAGTCTCTAGCCA

TTTAAAATTTTTGATGACCTGCTGCGACGCTTTTTTTCTGGCAAGATAGTCTTGTAAATGCGGGCC

AAGATCTGCACACTGGTATTTCGGTTTTTGGGGCCGCGGGGGGCGACGGGGCCCGTGCGTCCC

AGCGCACATGTTCGGCGAGGCGGGGCCTGCGAGCGCGGCCACCGAGAATCGGACGGGGGTAG

TCTCAAGCTGGCCGGCCTGCTCTGGTGCCTGGCCTCGCGCCGCCGTGTATCGCCCCGCCCTGG

GCGGCAAGGCTGGCCCGGTCGGCACCAGTTGCGTGAGCGGAAAGATGGCCGCTTCCCGGCCC

TGCTGCAGGGAGCTCAAAATGGAGGACGCGGCGCTCGGGAGAGCGGGGGGGTGAGTCACCCA

CACAAAGGAAAAGGGCCTTTCCGTCCTCAGCCGTCGCTTCATGTGACTCCACGGAGTACCGGGC

GCCGTCCAGGCACCTCGATTAGTTCTCGAGCTTTTGGAGTACGTCGTCTTTAGGTTGGGGGGAG

GGGTTTTATGCGATGGAGTTTCCCCACACTGAGTGGGTGGAGACTGAAGTTAGGCCAGCTTGGC

ACTTGATGTAATTCTCCTTGGAATTTGCCCTTTTTGAGTTTGGATCTTGGTTCATTCTCAAGCCTC

AGACAGTGGTTCAAAGTTTTTTTCTTOCATTTCAGGTGTC

SEQ ID NO: 6

5'-CTCGACTGTGCCTTCTAGTTG-3'

SEQ ID NO: 7

5'-GCACCTTCCAGGGTCAAG-3'

SEQ ID NO:8

5'-GGATTTGGTCGTATTGGG-3'

SEQ ID NO:9

5'-GGATTTGGTCGTATTGGG-3'

SEQ ID NO:10

5'-CGACTGGTGAGTACGCCAAA-3'

SEQ ID NO:11

5'-CGCACCCATCTCTCTCCTTCT-3'

SEQ ID NO:12

5'-ATTTTGACTAGCGGAGGC-3'

SEQ ID NO:13

5' tttaagaccaatgacttacaaggcagctgtagatcttagccactttttaaaagaaaaggggggactg gaagggctaattCACTCCCAACGAAGACAAGATCTGCTTTTTgCTgtgcgggccaggcccccgaggg ccttatcggccccagaggcgcttgctgtcgggccgggcgctcccggcacgggggggggaggggtggcg cccgcctggggACCgcagattacaagagcacctcctcccccaaccccaggaggccccgctccccagg cctcggcCgGcgcggacccctggttgccccggACTGGGTCTCTCTGGTTAGACCAGATCTGagcctg ggagctctctggctaactagggaacccactgcttaagcctcaataaagcttgccttgagtgcttcaa gtagtgtgtgcccgtctgttgtgtgactctggtaactagagatccctcagacccttttagtcagtgt ggaaaatctctagca-3'

OTHER EMBODIMENTS

Various modifications and variations of the described disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure that are obvious to those skilled in the art are intended to be within the scope of the disclosure.

Other embodiments are in the claims.

What is claimed:

1. An isolated polynucleotide comprising a nucleotide sequence of SEQ ID NO: 1 or comprising a nucleotide sequence of SEQ ID NO:3.

2. A lentiviral transfer vector comprising a) a promoter operably linked to an isolated polynucleotide comprising a nucleotide sequence of SEQ ID NO: 1 or comprising a nucleotide sequence of SEQ ID NO: 3.

3. The lentiviral transfer vector of claim 2, wherein the promoter is a human phosphoglycerate kinase promoter (PGK) comprising the nucleotide sequence of SEQ ID NO:4 or an EF1α promoter comprising the nucleotide sequence of SEQ ID NO: 5.

4. The lentiviral vector of claim 2, wherein the lentiviral components of the lentiviral vector originate from HIV-1.

5. The lentiviral vector of claim 2, further comprising one or more of a 5' long terminal repeat (LTR), a 3' LTR, a packaging signal, a Rev response element (RRE), a central polypurine tract (cPPT) sequence, and/or a central termination sequence (CTS).

6. The lentiviral vector of claim 5, wherein the 3' LTR is a self-inactivating 3'LTR.

7. The lentiviral vector of claim 5, wherein the 3' LTR comprises an insertion of a human ankyrin 1 element in the reverse orientation.

8. A virion comprising the lentiviral vector of claim 2.

9. A method of treating cystic fibrosis, the method comprising administering to a subject in need thereof a therapeutically effective amount of the lentiviral vector of claim 2.

10. The method of claim 9, further comprising administering one or more additional therapeutic agents to the subject.

11. The method of claim 10, wherein the one or more additional therapeutic agents includes an antibiotic, a mucus thinner, a CFTR modulator, a mucolytic, normal saline, hypertonic saline, or a combination thereof.

12. The method of claim 9, wherein the administering is by inhalation, nebulization, atomization or via atomizer, aerosolization, intranasally, intratracheally, intrabronchially, orally, intravenously, subcutaneously, or intramuscularly.

13. The method of claim 12, wherein the administering is by inhalation, nebulization, atomization or via atomizer, aerosolization, intranasally, intratracheally, and/or intrabronchially.

14. An atomizer sprayer or nebulizer comprising the isolated polynucleotide of claim 1.

* * * * *